US012806255B2

(12) United States Patent
Cerullo et al.

(10) Patent No.: US 12,806,255 B2
(45) **Date of Patent: *Nov. 24, 2026**

(54) MODIFIED ADENOVIRUSES FOR INFECTIOUS DISEASE VACCINE DEVELOPMENT

(71) Applicant: Valo Therapeutics Oy, Helsinki (FI)

(72) Inventors: Vincenzo Cerullo, Helsinki (FI); Markus Vähä-Koskela, Helsinki (FI); Mari Hirvinen, Helsinki (FI); Cristian Capasso, Helsinki (FI); Sari Pesonen, Helsinki (FI); Leena Ylösmäki, Helsinki (FI); Lukasz Kuryk, Helsinki (FI)

(73) Assignee: Valo Therapeutics Oy, Helsinki (FI)

( * ) Notice: Subject to any disclaimer, the term of this patent is extended or adjusted under 35 U.S.C. 154(b) by 767 days.

This patent is subject to a terminal disclaimer.

(21) Appl. No.: 17/943,838

(22) Filed: Sep. 13, 2022

(65) Prior Publication Data

US 2023/0062122 A1 Mar. 2, 2023

Related U.S. Application Data

(63) Continuation-in-part of application No. 17/009,929, filed on Sep. 2, 2020, now Pat. No. 11,730,798, which (Continued)

(30) Foreign Application Priority Data

May 19, 2014 (FI) ..................................... 20145449

(51) Int. Cl.
*A61K 39/385* (2006.01)
*A61K 39/00* (2006.01)

(52) U.S. Cl.
CPC .. *A61K 39/0011* (2013.01); *A61K 2039/5154* (2013.01); *A61K 2039/522* (2013.01);

(Continued)

(58) Field of Classification Search
None
See application file for complete search history.

(56) References Cited

U.S. PATENT DOCUMENTS

2004/0009939 A1 1/2004 Chada et al.
2004/0102382 A1 5/2004 Schughart et al.

(Continued)

FOREIGN PATENT DOCUMENTS

CN 1314948 9/2001
CN 103221423 7/2013

(Continued)

OTHER PUBLICATIONS

Vinge et al., Targeted Adenovirus Vectors for Delivery of Heterologous Genes, WO 00/12738, Mar. 9, 2000 (PCT application used as English Translation for CN1314948).

(Continued)

*Primary Examiner* — M Franco G Salvoza
(74) *Attorney, Agent, or Firm* — Patrick M. Torre; Stites & Harbison PLLC

(57) ABSTRACT

The present invention relates to adenoviral vectors, wherein the viral capsid has been coated with polypeptides, which are capable of stimulating a peptide-specific immune response in a subject and uses thereof (e.g. infectious disease). Furthermore, the present invention relates to methods of treating diseases, e.g., cancer or an infectious disease, by adenoviral vectors which have been coated by polypeptides causing peptide-specific immune response. Also the present invention relates to a method of coating adenoviral vectors by specific peptides as well as to a method of (Continued)

identifying those peptides suitable for coating the capsid of an adenoviral vector.

36 Claims, 21 Drawing Sheets

Specification includes a Sequence Listing.

Related U.S. Application Data is a continuation of application No. 15/312,388, filed as application No. PCT/EP2015/060903 on May 18, 2015, now Pat. No. 10,799,568.

(52) U.S. Cl.
CPC .... *A61K 2039/525* (2013.01); *A61K 2039/60* (2013.01); *C12N 2710/10042* (2013.01)

(56) References Cited

U.S. PATENT DOCUMENTS

| | | | | |
|---|---|---|---|---|
| 2013/0243731 A1* | 9/2013 | Dias | A61P 37/04 | 435/69.6 |
| 2014/0140962 A1* | 5/2014 | Carrico | A61K 47/549 | 435/235.1 |

FOREIGN PATENT DOCUMENTS

| | | | |
|---|---|---|---|
| EP | 1409012 B1 | 2/2009 | |
| WO | WO2012149160 A2 | 11/2012 | |

OTHER PUBLICATIONS

Diaconu et al., Oncolytic Adenoviral Vectors and Methods and Uses Related Thereto, WO 2012/038607 (PCT application used as English Translation for CN 103221423).

Instituto Nacional Da Propriedade Industrial, Office Action, Sep. 11, 2020.

Wang W et al, "Oncolytic adenovirus armed with human papillomavirus E2 gene in combination with radiation demonstrates synergistic enhancements of antitumor efficacy", Cancer Genetherapy, (Nov. 2011), vol. 18, No. 11, pp. 825-836 DOI: http://dx.doi.org/10.1038/cgt.2011.53.

Cody James J et al, "Expression of osteoprotegerin from a replicating adenovirus inhibits the progression of prostate cancer bone metastases in a murine model.", Laboratory Investigation; a Journal of Technical Methods and Pathology Mar. 2013, (Mar. 2013), vol. 93, No. 3, ISSN 1530-0307, pp. 268-278 DOI: http://dx.doi.org/10.1038/labinvest.2012.179.

Jiang, Z.K., et al. (2013) "Engineering polypeptide coatings to augment gene transduction and in vivo stability of adenoviruses." Journal of controlled release, vol. 166, No. 1, pp. 75-85.

Singh, R. and Kostas, K. (2009) "Designer adenoviruses for nanomedicine and nanodiagnostics." Trends in biotechnology, vol. 27, Issue 4, pp. 220-229.

ACS Chem Biol., vol. 8, No. 6, pp. 1253-1262 (Jun. 21, 2013).

Schneider H et al., "Retargeting of adenoviral vectors to nuerons using the HC fragments of tetanus toxins." Gene Therapy, vol. 7, 1584-, Sep. 25, 2000.

Zabrodskij P.F. et al. Immunotoksikologiya ksenobiotikov. Monografiya, SVIBHB, 2007, 420p.

* cited by examiner

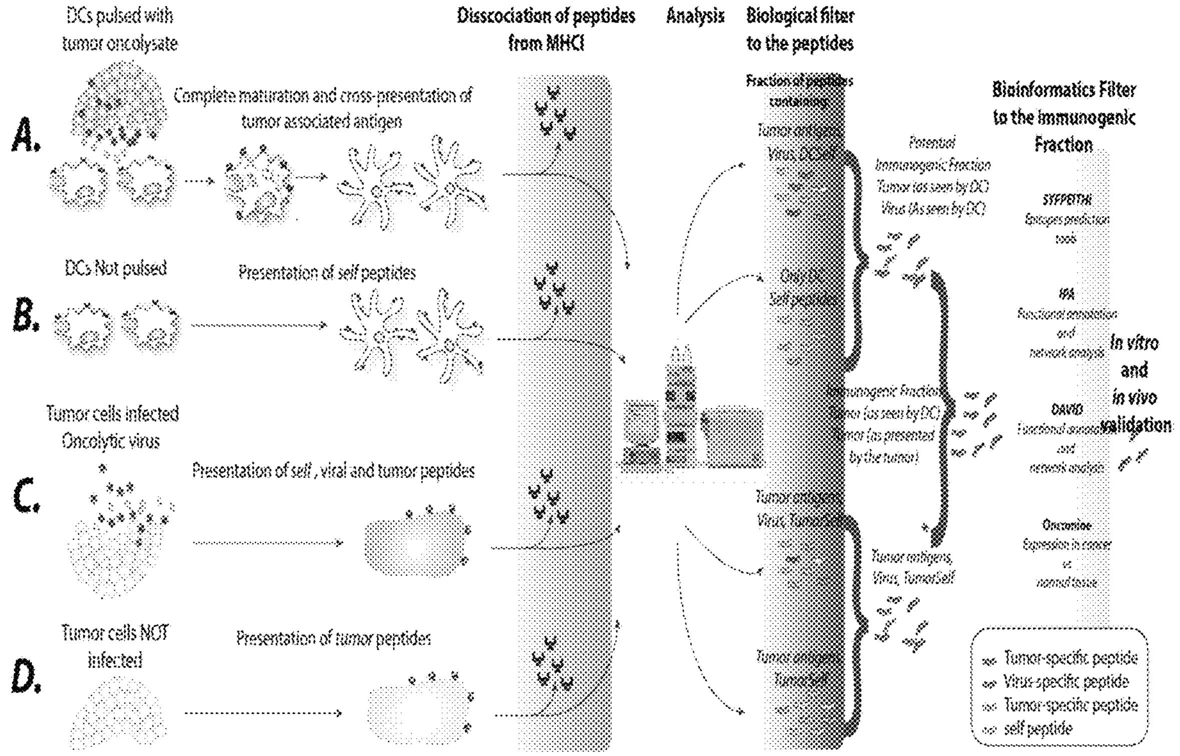
Fig. 5
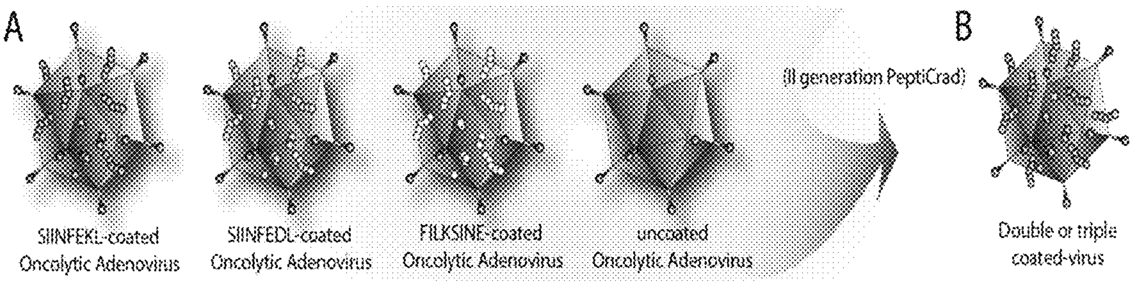
Fig. 6A
Fig. 6B

SEQUENCE LISTING

```
Sequence total quantity: 156
SEQ ID NO: 1            moltype = AA  length = 8
FEATURE                 Location/Qualifiers
REGION                  1..8
                        note = peptide fragment
source                  1..8
                        mol_type = protein
                        organism = synthetic construct
SEQUENCE: 1
SIINFEKL                                                                   8

SEQ ID NO: 2            moltype = AA  length = 7
FEATURE                 Location/Qualifiers
REGION                  1..7
                        note = peptide fragment
source                  1..7
                        mol_type = protein
                        organism = synthetic construct
SEQUENCE: 2
SIINFDL                                                                    7

SEQ ID NO: 3            moltype = AA  length = 8
FEATURE                 Location/Qualifiers
REGION                  1..8
                        note = peptide fragment
source                  1..8
                        mol_type = protein
                        organism = synthetic construct
SEQUENCE: 3
FILKSINE                                                                   8

SEQ ID NO: 4            moltype = AA  length = 9
FEATURE                 Location/Qualifiers
REGION                  1..9
                        note = peptide fragment
source                  1..9
                        mol_type = protein
                        organism = synthetic construct
SEQUENCE: 4
SLFRAVITK                                                                  9

SEQ ID NO: 5            moltype = AA  length = 9
FEATURE                 Location/Qualifiers
REGION                  1..9
                        note = peptide fragment
source                  1..9
                        mol_type = protein
                        organism = synthetic construct
SEQUENCE: 5
SVYDFFVWL                                                                  9

SEQ ID NO: 6            moltype = AA  length = 9
FEATURE                 Location/Qualifiers
REGION                  1..9
                        note = peptide fragment
source                  1..9
                        mol_type = protein
                        organism = synthetic construct
SEQUENCE: 6
KVPRNQDWL                                                                  9

SEQ ID NO: 7            moltype = AA  length = 8
FEATURE                 Location/Qualifiers
REGION                  1..8
                        note = peptide fragment
source                  1..8
                        mol_type = protein
                        organism = synthetic construct
SEQUENCE: 7
SIINFEDL                                                                   8

SEQ ID NO: 8            moltype = AA  length = 15
FEATURE                 Location/Qualifiers
source                  1..15
                        mol_type = protein
                        organism = synthetic construct
SEQUENCE: 8
KKKKKKLLLD RLNQL                                                           15
```

```
SEQ ID NO: 9            moltype = AA  length = 15
FEATURE                 Location/Qualifiers
source                  1..15
                        mol_type = protein
                        organism = synthetic construct
SEQUENCE: 9
KKKKKKFIAG LIAIV                                                  15

SEQ ID NO: 10           moltype = AA  length = 33
FEATURE                 Location/Qualifiers
source                  1..33
                        mol_type = protein
                        organism = synthetic construct
SEQUENCE: 10
KKKKKKKKKI AMACLVGLMW LSYFIASFRL FAR                              33

SEQ ID NO: 11           moltype = AA  length = 32
FEATURE                 Location/Qualifiers
source                  1..32
                        mol_type = protein
                        organism = synthetic construct
SEQUENCE: 11
KKKKKKKKKQ MAPISAMVRM YIFFASFYYV WK                               32

SEQ ID NO: 12           moltype = AA  length = 9
FEATURE                 Location/Qualifiers
source                  1..9
                        mol_type = protein
                        organism = synthetic construct
SEQUENCE: 12
LLLDRLNQL                                                         9

SEQ ID NO: 13           moltype = AA  length = 9
FEATURE                 Location/Qualifiers
source                  1..9
                        mol_type = protein
                        organism = synthetic construct
SEQUENCE: 13
FIAGLIAIV                                                         9

SEQ ID NO: 14           moltype = AA  length = 24
FEATURE                 Location/Qualifiers
source                  1..24
                        mol_type = protein
                        organism = synthetic construct
SEQUENCE: 14
IAMACLVGLM WLSYFIASFR LFAR                                        24

SEQ ID NO: 15           moltype = AA  length = 23
FEATURE                 Location/Qualifiers
source                  1..23
                        mol_type = protein
                        organism = synthetic construct
SEQUENCE: 15
QMAPISAMVR MYIFFASFYY VWK                                         23

SEQ ID NO: 16           moltype = AA  length = 15
FEATURE                 Location/Qualifiers
source                  1..15
                        mol_type = protein
                        organism = synthetic construct
SEQUENCE: 16
KKKKKKATDA LMTGY                                                  15

SEQ ID NO: 17           moltype = AA  length = 15
FEATURE                 Location/Qualifiers
source                  1..15
                        mol_type = protein
                        organism = synthetic construct
SEQUENCE: 17
KKKKKKATDA LMTGF                                                  15

SEQ ID NO: 18           moltype = AA  length = 15
FEATURE                 Location/Qualifiers
source                  1..15
                        mol_type = protein
                        organism = synthetic construct
SEQUENCE: 18
```

```
KKKKKKDLMG YIPAV                                                   15

SEQ ID NO: 19          moltype = AA  length = 15
FEATURE                Location/Qualifiers
source                 1..15
                       mol_type = protein
                       organism = synthetic construct
SEQUENCE: 19
KKKKKKCING VCWTV                                                   15

SEQ ID NO: 20          moltype = AA  length = 9
FEATURE                Location/Qualifiers
source                 1..9
                       mol_type = protein
                       organism = synthetic construct
SEQUENCE: 20
ATDALMTGY                                                          9

SEQ ID NO: 21          moltype = AA  length = 9
FEATURE                Location/Qualifiers
source                 1..9
                       mol_type = protein
                       organism = synthetic construct
SEQUENCE: 21
ATDALMTGF                                                          9

SEQ ID NO: 22          moltype = AA  length = 9
FEATURE                Location/Qualifiers
source                 1..9
                       mol_type = protein
                       organism = synthetic construct
SEQUENCE: 22
DLMGYIPAV                                                          9

SEQ ID NO: 23          moltype = AA  length = 9
FEATURE                Location/Qualifiers
source                 1..9
                       mol_type = protein
                       organism = synthetic construct
SEQUENCE: 23
CINGVCWTV                                                          9

SEQ ID NO: 24          moltype = AA  length = 9
FEATURE                Location/Qualifiers
source                 1..9
                       mol_type = protein
                       organism = synthetic construct
SEQUENCE: 24
CTELKLSDY                                                          9

SEQ ID NO: 25          moltype = AA  length = 9
FEATURE                Location/Qualifiers
source                 1..9
                       mol_type = protein
                       organism = synthetic construct
SEQUENCE: 25
VSDGGPNLY                                                          9

SEQ ID NO: 26          moltype = AA  length = 9
FEATURE                Location/Qualifiers
source                 1..9
                       mol_type = protein
                       organism = synthetic construct
SEQUENCE: 26
SIIPSGPLK                                                          9

SEQ ID NO: 27          moltype = AA  length = 9
FEATURE                Location/Qualifiers
source                 1..9
                       mol_type = protein
                       organism = synthetic construct
SEQUENCE: 27
ASNENMETM                                                          9

SEQ ID NO: 28          moltype = AA  length = 18
FEATURE                Location/Qualifiers
source                 1..18
                       mol_type = protein
                       organism = synthetic construct
```

-continued

```
SEQUENCE: 28
KKKKKKKKKC TELKLSDY                                            18

SEQ ID NO: 29          moltype = AA  length = 18
FEATURE                Location/Qualifiers
source                 1..18
                       mol_type = protein
                       organism = synthetic construct
SEQUENCE: 29
KKKKKKKKKV SDGGPNLY                                            18

SEQ ID NO: 30          moltype = AA  length = 15
FEATURE                Location/Qualifiers
source                 1..15
                       mol_type = protein
                       organism = synthetic construct
SEQUENCE: 30
KKKKKKSIIP SGPLK                                               15

SEQ ID NO: 31          moltype = AA  length = 15
FEATURE                Location/Qualifiers
source                 1..15
                       mol_type = protein
                       organism = synthetic construct
SEQUENCE: 31
KKKKKKASNE NMETM                                               15

SEQ ID NO: 32          moltype = AA  length = 15
FEATURE                Location/Qualifiers
source                 1..15
                       mol_type = protein
                       organism = synthetic construct
SEQUENCE: 32
KKKKKKKLIA NNTRV                                               15

SEQ ID NO: 33          moltype = AA  length = 15
FEATURE                Location/Qualifiers
source                 1..15
                       mol_type = protein
                       organism = synthetic construct
SEQUENCE: 33
KKKKKKGLPV EYLQV                                               15

SEQ ID NO: 34          moltype = AA  length = 16
FEATURE                Location/Qualifiers
source                 1..16
                       mol_type = protein
                       organism = synthetic construct
SEQUENCE: 34
KKKKKKVLTD GNPPEV                                              16

SEQ ID NO: 35          moltype = AA  length = 15
FEATURE                Location/Qualifiers
source                 1..15
                       mol_type = protein
                       organism = synthetic construct
SEQUENCE: 35
KKKKKKAMAS TEGNV                                               15

SEQ ID NO: 36          moltype = AA  length = 9
FEATURE                Location/Qualifiers
source                 1..9
                       mol_type = protein
                       organism = synthetic construct
SEQUENCE: 36
KLIANNTRV                                                      9

SEQ ID NO: 37          moltype = AA  length = 9
FEATURE                Location/Qualifiers
source                 1..9
                       mol_type = protein
                       organism = synthetic construct
SEQUENCE: 37
GLPVEYLQV                                                      9

SEQ ID NO: 38          moltype = AA  length = 10
FEATURE                Location/Qualifiers
source                 1..10
                       mol_type = protein
```

```
                         organism = synthetic construct
SEQUENCE: 38
VLTDGNPPEV                                                          10

SEQ ID NO: 39            moltype = AA  length = 9
FEATURE                  Location/Qualifiers
source                   1..9
                         mol_type = protein
                         organism = synthetic construct
SEQUENCE: 39
AMASTEGNV                                                           9

SEQ ID NO: 40            moltype = AA  length = 11
FEATURE                  Location/Qualifiers
source                   1..11
                         mol_type = protein
                         organism = synthetic construct
SEQUENCE: 40
SIINFEKLKK K                                                        11

SEQ ID NO: 41            moltype = AA  length = 12
FEATURE                  Location/Qualifiers
source                   1..12
                         mol_type = protein
                         organism = synthetic construct
SEQUENCE: 41
SIINFEKLKK KK                                                       12

SEQ ID NO: 42            moltype = AA  length = 13
FEATURE                  Location/Qualifiers
source                   1..13
                         mol_type = protein
                         organism = synthetic construct
SEQUENCE: 42
SIINFEKLKK KKK                                                      13

SEQ ID NO: 43            moltype = AA  length = 14
FEATURE                  Location/Qualifiers
source                   1..14
                         mol_type = protein
                         organism = synthetic construct
SEQUENCE: 43
SIINFEKLKK KKKK                                                     14

SEQ ID NO: 44            moltype = AA  length = 15
FEATURE                  Location/Qualifiers
source                   1..15
                         mol_type = protein
                         organism = synthetic construct
SEQUENCE: 44
SIINFEKLKK KKKKK                                                    15

SEQ ID NO: 45            moltype = AA  length = 16
FEATURE                  Location/Qualifiers
source                   1..16
                         mol_type = protein
                         organism = synthetic construct
SEQUENCE: 45
SIINFEKLKK KKKKKK                                                   16

SEQ ID NO: 46            moltype = AA  length = 16
FEATURE                  Location/Qualifiers
source                   1..16
                         mol_type = protein
                         organism = synthetic construct
SEQUENCE: 46
SIINFEKLKK KKKKKK                                                   16

SEQ ID NO: 47            moltype = AA  length = 18
FEATURE                  Location/Qualifiers
source                   1..18
                         mol_type = protein
                         organism = synthetic construct
SEQUENCE: 47
SIINFEKLKK KKKKKKKK                                                 18

SEQ ID NO: 48            moltype = AA  length = 19
FEATURE                  Location/Qualifiers
source                   1..19
```

```
                        mol_type = protein
                        organism = synthetic construct
SEQUENCE: 48
SIINFEKLKK KKKKKKKKK                                            19

SEQ ID NO: 49           moltype = AA  length = 20
FEATURE                 Location/Qualifiers
source                  1..20
                        mol_type = protein
                        organism = synthetic construct
SEQUENCE: 49
SIINFEKLKK KKKKKKKKKK                                           20

SEQ ID NO: 50           moltype = AA  length = 21
FEATURE                 Location/Qualifiers
source                  1..21
                        mol_type = protein
                        organism = synthetic construct
SEQUENCE: 50
SIINFEKLKK KKKKKKKKKK K                                         21

SEQ ID NO: 51           moltype = AA  length = 22
FEATURE                 Location/Qualifiers
source                  1..22
                        mol_type = protein
                        organism = synthetic construct
SEQUENCE: 51
SIINFEKLKK KKKKKKKKKK KK                                        22

SEQ ID NO: 52           moltype = AA  length = 23
FEATURE                 Location/Qualifiers
source                  1..23
                        mol_type = protein
                        organism = synthetic construct
SEQUENCE: 52
SIINFEKLKK KKKKKKKKKK KKK                                       23

SEQ ID NO: 53           moltype = AA  length = 11
FEATURE                 Location/Qualifiers
source                  1..11
                        mol_type = protein
                        organism = synthetic construct
SEQUENCE: 53
KKKSIINFEK L                                                    11

SEQ ID NO: 54           moltype = AA  length = 12
FEATURE                 Location/Qualifiers
source                  1..12
                        mol_type = protein
                        organism = synthetic construct
SEQUENCE: 54
KKKKSIINFE KL                                                   12

SEQ ID NO: 55           moltype = AA  length = 13
FEATURE                 Location/Qualifiers
source                  1..13
                        mol_type = protein
                        organism = synthetic construct
SEQUENCE: 55
KKKKKSIINF EKL                                                  13

SEQ ID NO: 56           moltype = AA  length = 14
FEATURE                 Location/Qualifiers
source                  1..14
                        mol_type = protein
                        organism = synthetic construct
SEQUENCE: 56
KKKKKKSIIN FEKL                                                 14

SEQ ID NO: 57           moltype = AA  length = 15
FEATURE                 Location/Qualifiers
source                  1..15
                        mol_type = protein
                        organism = synthetic construct
SEQUENCE: 57
KKKKKKKSII NFEKL                                                15

SEQ ID NO: 58           moltype = AA  length = 16
FEATURE                 Location/Qualifiers
```

```
source                1..16
                      mol_type = protein
                      organism = synthetic construct
SEQUENCE: 58
KKKKKKKKSI INFEKL                                                  16

SEQ ID NO: 59         moltype = AA  length = 17
FEATURE               Location/Qualifiers
source                1..17
                      mol_type = protein
                      organism = synthetic construct
SEQUENCE: 59
KKKKKKKKKS IINFEKL                                                 17

SEQ ID NO: 60         moltype = AA  length = 18
FEATURE               Location/Qualifiers
source                1..18
                      mol_type = protein
                      organism = synthetic construct
SEQUENCE: 60
KKKKKKKKKK SIINFEKL                                                18

SEQ ID NO: 61         moltype = AA  length = 19
FEATURE               Location/Qualifiers
source                1..19
                      mol_type = protein
                      organism = synthetic construct
SEQUENCE: 61
KKKKKKKKKK KSIINFEKL                                               19

SEQ ID NO: 62         moltype = AA  length = 20
FEATURE               Location/Qualifiers
source                1..20
                      mol_type = protein
                      organism = synthetic construct
SEQUENCE: 62
KKKKKKKKKK KKSIINFEKL                                              20

SEQ ID NO: 63         moltype = AA  length = 21
FEATURE               Location/Qualifiers
source                1..21
                      mol_type = protein
                      organism = synthetic construct
SEQUENCE: 63
KKKKKKKKKK KKKSIINFEK L                                            21

SEQ ID NO: 64         moltype = AA  length = 22
FEATURE               Location/Qualifiers
source                1..22
                      mol_type = protein
                      organism = synthetic construct
SEQUENCE: 64
KKKKKKKKKK KKKKSIINFE KL                                           22

SEQ ID NO: 65         moltype = AA  length = 23
FEATURE               Location/Qualifiers
source                1..23
                      mol_type = protein
                      organism = synthetic construct
SEQUENCE: 65
KKKKKKKKKK KKKKKSIINF EKL                                          23

SEQ ID NO: 66         moltype = AA  length = 12
FEATURE               Location/Qualifiers
source                1..12
                      mol_type = protein
                      organism = synthetic construct
SEQUENCE: 66
SLFRAVITKK KK                                                      12

SEQ ID NO: 67         moltype = AA  length = 13
FEATURE               Location/Qualifiers
source                1..13
                      mol_type = protein
                      organism = synthetic construct
SEQUENCE: 67
SLFRAVITKK KKK                                                     13

SEQ ID NO: 68         moltype = AA  length = 14
```

-continued

```
FEATURE                  Location/Qualifiers
source                   1..14
                         mol_type = protein
                         organism = synthetic construct
SEQUENCE: 68
SLFRAVITKK KKKK                                                    14

SEQ ID NO: 69            moltype = AA  length = 15
FEATURE                  Location/Qualifiers
source                   1..15
                         mol_type = protein
                         organism = synthetic construct
SEQUENCE: 69
SLFRAVITKK KKKKK                                                   15

SEQ ID NO: 70            moltype = AA  length = 16
FEATURE                  Location/Qualifiers
source                   1..16
                         mol_type = protein
                         organism = synthetic construct
SEQUENCE: 70
SLFRAVITKK KKKKKK                                                  16

SEQ ID NO: 71            moltype = AA  length = 17
FEATURE                  Location/Qualifiers
source                   1..17
                         mol_type = protein
                         organism = synthetic construct
SEQUENCE: 71
SLFRAVITKK KKKKKKK                                                 17

SEQ ID NO: 72            moltype = AA  length = 18
FEATURE                  Location/Qualifiers
source                   1..18
                         mol_type = protein
                         organism = synthetic construct
SEQUENCE: 72
SLFRAVITKK KKKKKKKK                                                18

SEQ ID NO: 73            moltype = AA  length = 19
FEATURE                  Location/Qualifiers
source                   1..19
                         mol_type = protein
                         organism = synthetic construct
SEQUENCE: 73
SLFRAVITKK KKKKKKKKK                                               19

SEQ ID NO: 74            moltype = AA  length = 20
FEATURE                  Location/Qualifiers
source                   1..20
                         mol_type = protein
                         organism = synthetic construct
SEQUENCE: 74
SLFRAVITKK KKKKKKKKKK                                              20

SEQ ID NO: 75            moltype = AA  length = 21
FEATURE                  Location/Qualifiers
source                   1..21
                         mol_type = protein
                         organism = synthetic construct
SEQUENCE: 75
SLFRAVITKK KKKKKKKKKK K                                            21

SEQ ID NO: 76            moltype = AA  length = 22
FEATURE                  Location/Qualifiers
source                   1..22
                         mol_type = protein
                         organism = synthetic construct
SEQUENCE: 76
SLFRAVITKK KKKKKKKKKK KK                                           22

SEQ ID NO: 77            moltype = AA  length = 23
FEATURE                  Location/Qualifiers
source                   1..23
                         mol_type = protein
                         organism = synthetic construct
SEQUENCE: 77
SLFRAVITKK KKKKKKKKKK KKK                                          23
```

```
SEQ ID NO: 78          moltype = AA  length = 24
FEATURE                Location/Qualifiers
source                 1..24
                       mol_type = protein
                       organism = synthetic construct
SEQUENCE: 78
SLFRAVITKK KKKKKKKKKK KKKK                                            24

SEQ ID NO: 79          moltype = AA  length = 12
FEATURE                Location/Qualifiers
source                 1..12
                       mol_type = protein
                       organism = synthetic construct
SEQUENCE: 79
KKKSLFRAVI TK                                                         12

SEQ ID NO: 80          moltype = AA  length = 13
FEATURE                Location/Qualifiers
source                 1..13
                       mol_type = protein
                       organism = synthetic construct
SEQUENCE: 80
KKKKSLFRAV ITK                                                        13

SEQ ID NO: 81          moltype = AA  length = 14
FEATURE                Location/Qualifiers
source                 1..14
                       mol_type = protein
                       organism = synthetic construct
SEQUENCE: 81
KKKKKSLFRA VITK                                                       14

SEQ ID NO: 82          moltype = AA  length = 15
FEATURE                Location/Qualifiers
source                 1..15
                       mol_type = protein
                       organism = synthetic construct
SEQUENCE: 82
KKKKKKSLFR AVITK                                                      15

SEQ ID NO: 83          moltype = AA  length = 16
FEATURE                Location/Qualifiers
source                 1..16
                       mol_type = protein
                       organism = synthetic construct
SEQUENCE: 83
KKKKKKKSLF RAVITK                                                     16

SEQ ID NO: 84          moltype = AA  length = 17
FEATURE                Location/Qualifiers
source                 1..17
                       mol_type = protein
                       organism = synthetic construct
SEQUENCE: 84
KKKKKKKKSL FRAVITK                                                    17

SEQ ID NO: 85          moltype = AA  length = 18
FEATURE                Location/Qualifiers
source                 1..18
                       mol_type = protein
                       organism = synthetic construct
SEQUENCE: 85
KKKKKKKKKS LFRAVITK                                                   18

SEQ ID NO: 86          moltype = AA  length = 19
FEATURE                Location/Qualifiers
source                 1..19
                       mol_type = protein
                       organism = synthetic construct
SEQUENCE: 86
KKKKKKKKKK SLFRAVITK                                                  19

SEQ ID NO: 87          moltype = AA  length = 20
FEATURE                Location/Qualifiers
source                 1..20
                       mol_type = protein
                       organism = synthetic construct
SEQUENCE: 87
KKKKKKKKKK KSLFRAVITK                                                 20
```

```
SEQ ID NO: 88          moltype = AA  length = 21
FEATURE                Location/Qualifiers
source                 1..21
                       mol_type = protein
                       organism = synthetic construct
SEQUENCE: 88
KKKKKKKKKK KKSLFRAVIT K                                            21

SEQ ID NO: 89          moltype = AA  length = 22
FEATURE                Location/Qualifiers
source                 1..22
                       mol_type = protein
                       organism = synthetic construct
SEQUENCE: 89
KKKKKKKKKK KKKSLFRAVI TK                                           22

SEQ ID NO: 90          moltype = AA  length = 23
FEATURE                Location/Qualifiers
source                 1..23
                       mol_type = protein
                       organism = synthetic construct
SEQUENCE: 90
KKKKKKKKKK KKKKSLFRAV ITK                                          23

SEQ ID NO: 91          moltype = AA  length = 24
FEATURE                Location/Qualifiers
source                 1..24
                       mol_type = protein
                       organism = synthetic construct
SEQUENCE: 91
KKKKKKKKKK KKKKKSLFRA VITK                                         24

SEQ ID NO: 92          moltype = AA  length = 12
FEATURE                Location/Qualifiers
source                 1..12
                       mol_type = protein
                       organism = synthetic construct
SEQUENCE: 92
SVYDFFVWLK KK                                                      12

SEQ ID NO: 93          moltype = AA  length = 13
FEATURE                Location/Qualifiers
source                 1..13
                       mol_type = protein
                       organism = synthetic construct
SEQUENCE: 93
SVYDFFVWLK KKK                                                     13

SEQ ID NO: 94          moltype = AA  length = 14
FEATURE                Location/Qualifiers
source                 1..14
                       mol_type = protein
                       organism = synthetic construct
SEQUENCE: 94
SVYDFFVWLK KKKK                                                    14

SEQ ID NO: 95          moltype = AA  length = 15
FEATURE                Location/Qualifiers
source                 1..15
                       mol_type = protein
                       organism = synthetic construct
SEQUENCE: 95
SVYDFFVWLK KKKKK                                                   15

SEQ ID NO: 96          moltype = AA  length = 16
FEATURE                Location/Qualifiers
source                 1..16
                       mol_type = protein
                       organism = synthetic construct
SEQUENCE: 96
SVYDFFVWLK KKKKKK                                                  16

SEQ ID NO: 97          moltype = AA  length = 17
FEATURE                Location/Qualifiers
source                 1..17
                       mol_type = protein
                       organism = synthetic construct
SEQUENCE: 97
```

```
SVYDFFVWLK KKKKKKK                                              17

SEQ ID NO: 98          moltype = AA  length = 18
FEATURE                Location/Qualifiers
source                 1..18
                       mol_type = protein
                       organism = synthetic construct
SEQUENCE: 98
SVYDFFVWLK KKKKKKKK                                             18

SEQ ID NO: 99          moltype = AA  length = 19
FEATURE                Location/Qualifiers
source                 1..19
                       mol_type = protein
                       organism = synthetic construct
SEQUENCE: 99
SVYDFFVWLK KKKKKKKKK                                            19

SEQ ID NO: 100         moltype = AA  length = 20
FEATURE                Location/Qualifiers
source                 1..20
                       mol_type = protein
                       organism = synthetic construct
SEQUENCE: 100
SVYDFFVWLK KKKKKKKKKK                                           20

SEQ ID NO: 101         moltype = AA  length = 21
FEATURE                Location/Qualifiers
source                 1..21
                       mol_type = protein
                       organism = synthetic construct
SEQUENCE: 101
SVYDFFVWLK KKKKKKKKKK K                                         21

SEQ ID NO: 102         moltype = AA  length = 22
FEATURE                Location/Qualifiers
source                 1..22
                       mol_type = protein
                       organism = synthetic construct
SEQUENCE: 102
SVYDFFVWLK KKKKKKKKKK KK                                        22

SEQ ID NO: 103         moltype = AA  length = 23
FEATURE                Location/Qualifiers
source                 1..23
                       mol_type = protein
                       organism = synthetic construct
SEQUENCE: 103
SVYDFFVWLK KKKKKKKKKK KKK                                       23

SEQ ID NO: 104         moltype = AA  length = 24
FEATURE                Location/Qualifiers
source                 1..24
                       mol_type = protein
                       organism = synthetic construct
SEQUENCE: 104
SVYDFFVWLK KKKKKKKKKK KKKK                                      24

SEQ ID NO: 105         moltype = AA  length = 12
FEATURE                Location/Qualifiers
source                 1..12
                       mol_type = protein
                       organism = synthetic construct
SEQUENCE: 105
KKKSVYDFFV WL                                                   12

SEQ ID NO: 106         moltype = AA  length = 13
FEATURE                Location/Qualifiers
source                 1..13
                       mol_type = protein
                       organism = synthetic construct
SEQUENCE: 106
KKKKSVYDFF VWL                                                  13

SEQ ID NO: 107         moltype = AA  length = 14
FEATURE                Location/Qualifiers
source                 1..14
                       mol_type = protein
                       organism = synthetic construct
```

```
SEQUENCE: 107
KKKKKSVYDF FVWL                                                      14

SEQ ID NO: 108          moltype = AA  length = 15
FEATURE                 Location/Qualifiers
source                  1..15
                        mol_type = protein
                        organism = synthetic construct
SEQUENCE: 108
KKKKKKSVYD FFVWL                                                     15

SEQ ID NO: 109          moltype = AA  length = 16
FEATURE                 Location/Qualifiers
source                  1..16
                        mol_type = protein
                        organism = synthetic construct
SEQUENCE: 109
KKKKKKKSVY DFFVWL                                                    16

SEQ ID NO: 110          moltype = AA  length = 17
FEATURE                 Location/Qualifiers
source                  1..17
                        mol_type = protein
                        organism = synthetic construct
SEQUENCE: 110
KKKKKKKKSV YDFFVWL                                                   17

SEQ ID NO: 111          moltype = AA  length = 18
FEATURE                 Location/Qualifiers
source                  1..18
                        mol_type = protein
                        organism = synthetic construct
SEQUENCE: 111
KKKKKKKKKS VYDFFVWL                                                  18

SEQ ID NO: 112          moltype = AA  length = 19
FEATURE                 Location/Qualifiers
source                  1..19
                        mol_type = protein
                        organism = synthetic construct
SEQUENCE: 112
KKKKKKKKKK SVYDFFVWL                                                 19

SEQ ID NO: 113          moltype = AA  length = 20
FEATURE                 Location/Qualifiers
source                  1..20
                        mol_type = protein
                        organism = synthetic construct
SEQUENCE: 113
KKKKKKKKKK KSVYDFFVWL                                                20

SEQ ID NO: 114          moltype = AA  length = 21
FEATURE                 Location/Qualifiers
source                  1..21
                        mol_type = protein
                        organism = synthetic construct
SEQUENCE: 114
KKKKKKKKKK KKSVYDFFVW L                                              21

SEQ ID NO: 115          moltype = AA  length = 22
FEATURE                 Location/Qualifiers
source                  1..22
                        mol_type = protein
                        organism = synthetic construct
SEQUENCE: 115
KKKKKKKKKK KKKSVYDFFV WL                                             22

SEQ ID NO: 116          moltype = AA  length = 23
FEATURE                 Location/Qualifiers
source                  1..23
                        mol_type = protein
                        organism = synthetic construct
SEQUENCE: 116
KKKKKKKKKK KKKKSVYDFF VWL                                            23

SEQ ID NO: 117          moltype = AA  length = 24
FEATURE                 Location/Qualifiers
source                  1..24
                        mol_type = protein
```

```
                      organism = synthetic construct
SEQUENCE: 117
KKKKKKKKKK KKKKKSVYDF FVWL                                              24

SEQ ID NO: 118        moltype = AA  length = 12
FEATURE               Location/Qualifiers
source                1..12
                      mol_type = protein
                      organism = synthetic construct
SEQUENCE: 118
KVPRNQDWLK KK                                                           12

SEQ ID NO: 119        moltype = AA  length = 13
FEATURE               Location/Qualifiers
source                1..13
                      mol_type = protein
                      organism = synthetic construct
SEQUENCE: 119
KVPRNQDWLK KKK                                                          13

SEQ ID NO: 120        moltype = AA  length = 14
FEATURE               Location/Qualifiers
source                1..14
                      mol_type = protein
                      organism = synthetic construct
SEQUENCE: 120
KVPRNQDWLK KKKK                                                         14

SEQ ID NO: 121        moltype = AA  length = 15
FEATURE               Location/Qualifiers
source                1..15
                      mol_type = protein
                      organism = synthetic construct
SEQUENCE: 121
KVPRNQDWLK KKKKK                                                        15

SEQ ID NO: 122        moltype = AA  length = 16
FEATURE               Location/Qualifiers
source                1..16
                      mol_type = protein
                      organism = synthetic construct
SEQUENCE: 122
KVPRNQDWLK KKKKKK                                                       16

SEQ ID NO: 123        moltype = AA  length = 17
FEATURE               Location/Qualifiers
source                1..17
                      mol_type = protein
                      organism = synthetic construct
SEQUENCE: 123
KVPRNQDWLK KKKKKKK                                                      17

SEQ ID NO: 124        moltype = AA  length = 18
FEATURE               Location/Qualifiers
source                1..18
                      mol_type = protein
                      organism = synthetic construct
SEQUENCE: 124
KVPRNQDWLK KKKKKKKK                                                     18

SEQ ID NO: 125        moltype = AA  length = 19
FEATURE               Location/Qualifiers
source                1..19
                      mol_type = protein
                      organism = synthetic construct
SEQUENCE: 125
KVPRNQDWLK KKKKKKKKK                                                    19

SEQ ID NO: 126        moltype = AA  length = 20
FEATURE               Location/Qualifiers
source                1..20
                      mol_type = protein
                      organism = synthetic construct
SEQUENCE: 126
KVPRNQDWLK KKKKKKKKKK                                                   20

SEQ ID NO: 127        moltype = AA  length = 21
FEATURE               Location/Qualifiers
source                1..21
```

```
                        mol_type = protein
                        organism = synthetic construct
SEQUENCE: 127
KVPRNQDWLK KKKKKKKKKK K                                                21

SEQ ID NO: 128          moltype = AA  length = 22
FEATURE                 Location/Qualifiers
source                  1..22
                        mol_type = protein
                        organism = synthetic construct
SEQUENCE: 128
KVPRNQDWLK KKKKKKKKKK KK                                               22

SEQ ID NO: 129          moltype = AA  length = 23
FEATURE                 Location/Qualifiers
source                  1..23
                        mol_type = protein
                        organism = synthetic construct
SEQUENCE: 129
KVPRNQDWLK KKKKKKKKKK KKK                                              23

SEQ ID NO: 130          moltype = AA  length = 24
FEATURE                 Location/Qualifiers
source                  1..24
                        mol_type = protein
                        organism = synthetic construct
SEQUENCE: 130
KVPRNQDWLK KKKKKKKKKK KKKK                                             24

SEQ ID NO: 131          moltype = AA  length = 12
FEATURE                 Location/Qualifiers
source                  1..12
                        mol_type = protein
                        organism = synthetic construct
SEQUENCE: 131
KKKKVPRNQD WL                                                          12

SEQ ID NO: 132          moltype = AA  length = 13
FEATURE                 Location/Qualifiers
source                  1..13
                        mol_type = protein
                        organism = synthetic construct
SEQUENCE: 132
KKKKSVYDFF VWL                                                         13

SEQ ID NO: 133          moltype = AA  length = 14
FEATURE                 Location/Qualifiers
source                  1..14
                        mol_type = protein
                        organism = synthetic construct
SEQUENCE: 133
KKKKKKVPRN QDWL                                                        14

SEQ ID NO: 134          moltype = AA  length = 15
FEATURE                 Location/Qualifiers
source                  1..15
                        mol_type = protein
                        organism = synthetic construct
SEQUENCE: 134
KKKKKKKVPR NQDWL                                                       15

SEQ ID NO: 135          moltype = AA  length = 16
FEATURE                 Location/Qualifiers
source                  1..16
                        mol_type = protein
                        organism = synthetic construct
SEQUENCE: 135
KKKKKKKKVP RNQDWL                                                      16

SEQ ID NO: 136          moltype = AA  length = 17
FEATURE                 Location/Qualifiers
source                  1..17
                        mol_type = protein
                        organism = synthetic construct
SEQUENCE: 136
KKKKKKKKKV PRNQDWL                                                     17

SEQ ID NO: 137          moltype = AA  length = 18
FEATURE                 Location/Qualifiers
```

```
source                  1..18
                        mol_type = protein
                        organism = synthetic construct
SEQUENCE: 137
KKKKKKKKKK VPRNQDWL                                                18

SEQ ID NO: 138          moltype = AA  length = 19
FEATURE                 Location/Qualifiers
source                  1..19
                        mol_type = protein
                        organism = synthetic construct
SEQUENCE: 138
KKKKKKKKKK KVPRNQDWL                                               19

SEQ ID NO: 139          moltype = AA  length = 20
FEATURE                 Location/Qualifiers
source                  1..20
                        mol_type = protein
                        organism = synthetic construct
SEQUENCE: 139
KKKKKKKKKK KKVPRNQDWL                                              20

SEQ ID NO: 140          moltype = AA  length = 21
FEATURE                 Location/Qualifiers
source                  1..21
                        mol_type = protein
                        organism = synthetic construct
SEQUENCE: 140
KKKKKKKKKK KKKVPRNQDW L                                            21

SEQ ID NO: 141          moltype = AA  length = 22
FEATURE                 Location/Qualifiers
source                  1..22
                        mol_type = protein
                        organism = synthetic construct
SEQUENCE: 141
KKKKKKKKKK KKKKVPRNQD WL                                           22

SEQ ID NO: 142          moltype = AA  length = 23
FEATURE                 Location/Qualifiers
source                  1..23
                        mol_type = protein
                        organism = synthetic construct
SEQUENCE: 142
KKKKKKKKKK KKKKKVPRNQ DWL                                          23

SEQ ID NO: 143          moltype = AA  length = 24
FEATURE                 Location/Qualifiers
source                  1..24
                        mol_type = protein
                        organism = synthetic construct
SEQUENCE: 143
KKKKKKKKKK KKKKKKVPRN QDWL                                         24

SEQ ID NO: 144          moltype = AA  length = 12
FEATURE                 Location/Qualifiers
source                  1..12
                        mol_type = protein
                        organism = synthetic construct
MOD_RES                 9
                        note = Acp
SEQUENCE: 144
SIINFEKLXK KK                                                      12

SEQ ID NO: 145          moltype = AA  length = 13
FEATURE                 Location/Qualifiers
source                  1..13
                        mol_type = protein
                        organism = synthetic construct
MOD_RES                 9
                        note = Acp
SEQUENCE: 145
SIINFEKLXK KKK                                                     13

SEQ ID NO: 146          moltype = AA  length = 14
FEATURE                 Location/Qualifiers
source                  1..14
                        mol_type = protein
                        organism = synthetic construct
```

```
MOD_RES                 9
                        note = Acp
SEQUENCE: 146
SIINFEKLXK KKKK                                                  14

SEQ ID NO: 147          moltype = AA  length = 15
FEATURE                 Location/Qualifiers
source                  1..15
                        mol_type = protein
                        organism = synthetic construct
MOD_RES                 9
                        note = Acp
SEQUENCE: 147
SIINFEKLXK KKKKK                                                 15

SEQ ID NO: 148          moltype = AA  length = 16
FEATURE                 Location/Qualifiers
source                  1..16
                        mol_type = protein
                        organism = synthetic construct
MOD_RES                 9
                        note = Acp
SEQUENCE: 148
SIINFEKLXK KKKKKK                                                16

SEQ ID NO: 149          moltype = AA  length = 17
FEATURE                 Location/Qualifiers
source                  1..17
                        mol_type = protein
                        organism = synthetic construct
MOD_RES                 9
                        note = Acp
SEQUENCE: 149
SIINFEKLXK KKKKKKK                                               17

SEQ ID NO: 150          moltype = AA  length = 18
FEATURE                 Location/Qualifiers
source                  1..18
                        mol_type = protein
                        organism = synthetic construct
MOD_RES                 9
                        note = Acp
SEQUENCE: 150
SIINFEKLXK KKKKKKKK                                              18

SEQ ID NO: 151          moltype = AA  length = 19
FEATURE                 Location/Qualifiers
source                  1..19
                        mol_type = protein
                        organism = synthetic construct
MOD_RES                 9
                        note = Acp
SEQUENCE: 151
SIINFEKLXK KKKKKKKKK                                             19

SEQ ID NO: 152          moltype = AA  length = 20
FEATURE                 Location/Qualifiers
source                  1..20
                        mol_type = protein
                        organism = synthetic construct
MOD_RES                 9
                        note = Acp
SEQUENCE: 152
SIINFEKLXK KKKKKKKKKK                                            20

SEQ ID NO: 153          moltype = AA  length = 21
FEATURE                 Location/Qualifiers
source                  1..21
                        mol_type = protein
                        organism = synthetic construct
MOD_RES                 9
                        note = Acp
SEQUENCE: 153
SIINFEKLXK KKKKKKKKKK K                                          21

SEQ ID NO: 154          moltype = AA  length = 22
FEATURE                 Location/Qualifiers
source                  1..22
                        mol_type = protein
```

-continued

```
                        organism = synthetic construct
MOD_RES                 9
                        note = Acp
SEQUENCE: 154
SIINFEKLXK KKKKKKKKKK KK                                            22

SEQ ID NO: 155          moltype = AA  length = 23
FEATURE                 Location/Qualifiers
source                  1..23
                        mol_type = protein
                        organism = synthetic construct
MOD_RES                 9
                        note = Acp
SEQUENCE: 155
SIINFEKLXK KKKKKKKKKK KKK                                           23

SEQ ID NO: 156          moltype = AA  length = 24
FEATURE                 Location/Qualifiers
source                  1..24
                        mol_type = protein
                        organism = synthetic construct
MOD_RES                 9
                        note = Acp
SEQUENCE: 156
SIINFEKLXK KKKKKKKKKK KKKK                                          24
```

MODIFIED ADENOVIRUSES FOR INFECTIOUS DISEASE VACCINE DEVELOPMENT

RELATED APPLICATIONS

This application is a continuation-in-part patent application claiming priority to U.S. patent application Ser. No. 17/009,929 filed on Sep. 2, 2020, which in turn claims priority as a continuation of U.S. patent application Ser. No. 15/312,388, now U.S. Pat. No. 10,799,568, filed on Nov. 18, 2016, which in turn is the national stage of international patent application no. PCT/EP2015/060903 filed on May 18, 2015, which in turn claims priority from Finnish Patent Application No. 20145449 filed on May 19, 2014, the disclosures of which are incorporated herein by reference in their entirety.

A portion of the disclosure of this patent document contains material which is subject to copyright or mask work notice. The copyright owner has no objection to the facsimile reproduction by anyone of the patent document or the patent disclosure, as it appears in the Patent and Trademark Office patent file or records, but otherwise reserves all copyright rights whatsoever.

REFERENCE TO SEQUENCE LISTING SUBMITTED ELECTRONICALLY

A sequence listing electronically submitted with the present application as an XML format file named 4570P-US2 SEQ LIST.xml, created on 09-01-2022 and having a size of 37000 bytes, is incorporated herein by reference in its entirety.

TECHNICAL FIELD

The present invention relates to adenoviral vectors, wherein the viral capsid has been coated with polypeptides, which are capable of stimulating a peptide-specific immune response in a subject and uses thereof (e.g. infectious disease). Furthermore, the present invention relates to methods of treating diseases, e.g. cancer or infectious diseases, by adenoviral vectors which have been coated by polypeptides causing peptide-specific immune response. Also, the present invention relates to a method of coating adenoviral vectors by specific peptides as well as to a method of identifying those peptides suitable for coating the capsid of an adenoviral vector.

BACKGROUND

Cancer is a lethal disease in need of more effective treatments. Also, multidrug-resistant infections are rapidly increasing worldwide. The emergence of infections for which there are limited prophylactic and treatment options represents a critical unmet medical need. Oncolytic viruses are of significant interest since they have the potential to be safer and more effective than any other standard therapy. However, in cancer patients the overall therapeutic effect has been modest. There are many studies on modifying the adenoviral vectors in order to find optimal tools for therapies. One aspect of regulating the function of adenoviruses is to modify the surface of the virus. Both genetic as well as non-genetic modifications of surfaces of adenoviruses are well known.

For example Stevenson M et al. (Cancer Gene Therapy (2007) 14, 335-345) concentrate on enhancing the delivery of adenoviral vectors to target sites. Stevenson et al. describe a study wherein adenoviral vectors are targeted to infect cells via integrins that are selectively expressed on metastatic tumor cells. For this purpose a laminin-derived peptide (-SIKVAV-) was incorporated onto the surface of the polymer-coated viruses.

WO2013/116778 describes an immunologically enhanced adenovirus for cancer. An adenovirus was modified by inserting a tumor antigen transgene into its genome in a way that the tumor antigen is expressed during the virus's replication cycle and presented directly to MHC-I. This method is very slow and too laborious and expensive for personalized therapies, because the generation of a new virus is needed for every different tumor antigen (e.g. one must clone anew virus for every peptide that is wanted to be expressed).

Indeed, a need exists for simple and improved adenoviral tools and methods for therapeutics, especially for personalized therapies. The present invention provides adenoviral applications for directing the immune response in a subject while using the virus as delivery system of peptides but not involving genetic manipulation of the virus.

The present invention relates to the use of oncolytic adenoviruses and non-replicating adenoviruses as platform to deliver patient- and disease-specific peptides and consequently convert the anti-capsid immunity into a peptide specific immune response (e.g. anti-tumor immunity, anti-infection immunity).

SUMMARY

The present invention provides a new and potent customizable immunovirotherapy (e.g. cancer, infectious diseases, immunovirotherapy) platform. An object is to provide an adenoviral vector with modified viral surface, uses thereof and a method for treating a disease by stimulating a peptide-specific (i.e. anti-peptide) immune response to solve the problems of e.g. inefficient, slow, expensive and laborious adenoviral therapies as well as the unsuitability of the adenoviral therapies for personalized medicine. The objects of the invention are achieved by an arrangement and a method, which are characterized by what is stated in the independent claims. The preferred embodiments of the invention are disclosed in the dependent claims.

By the present invention problems of prior art e.g. lack of specificity and the immune dominance of oncolytic and non-replicating adenoviruses can be overcome.

Immune responses generated by adenovirus infection target mainly the virus and not the tumor. Furthermore, the majority of the viral immunity is directed against the proteins of the capsid. The present invention will overcome these problems. Indeed, the present invention is based on the idea that coating the viral capsid with peptides derived from tumor proteins diverts viral immunity to the tumor (FIG. 3). The major histocompatibility complex I (MHC-I) restricted peptides mounted onto the oncolytic adenovirus capsid divert the capsid immunity into anti-tumor immunity.

Simply, when peptide(s) and virus(es) are administered as a single physically linked entity, both danger signal (virus) and tumor-antigen (peptide) will enter the same antigen presenting cell for maximal anti-tumor effect. Clinical experience has already indicated that peptide vaccination alone only leads to a transient and suboptimal immune response incapable of controlling tumor growth[1].

Correspondingly, while oncolytic viruses show promise as monotherapy, the immune response they elicit is mainly targeted against the virus, not the tumor. Even if peptide and virus are injected in the same anatomical location, since they are not joint in a single therapeutic entity, they inefficiently enter the same cell—aspects which are critical for achieving proper and maximal immune activation[2]. The physical conjunction of peptide and adenoviral virus in a single therapeutic entity is a significant improvement over existing virus and peptide cancer and infectious disease vaccine technologies. In contrast to recombinant viruses of the prior art engineered to express one tumor-associated antigen or peptide, the present invention makes it possible to achieve personalized medicines in a much quicker and more cost-effective way than before. Indeed, according to the present invention peptides attached onto a viral capsid are not encoded by the adenoviral vector.

One aspect of the present invention is the technology allowing constant and rapid monitoring of tumor antigen presentation as small peptides (MHC-I restricted). The present invention takes advantage of disease- (e.g. tumor-) and patient-specific peptides, which are presented simultaneously on tumor cells both before and after adenoviral therapy (i.e. which are not masked or edited away after therapy) and on dendritic cells (DCs) following adenoviral therapy. After identification of these specific peptides they can be synthetized and mounted onto the oncolytic adenovirus capsid to achieve high anti-tumor immunity. This way it is possible to ensure that the tumor is effectively targeted by cytotoxic T-cells (CTLs) also after virotherapy so that immunological escape becomes impossible as the immune system targets the virus. Conversely, by comparing peptides appearing on DCs after virus therapy in the presence or absence of tumor, it is possible to eliminate "virus-only" peptides and find those deriving from the tumor cells that induce CTL response.

A personalized coated adenovirus can be obtained in as little as two weeks from biopsy; this is made possible because isolation and sequencing of peptides from MHC's as well as automated synthesis are rapid processes, and the virus (e.g. the same backbone virus for all peptides) can be stockpiled in large quantities to await coating. Coating itself is performed in one hour, after which the coated adenovirus is ready for injection. This is very unique feature of our system as it bypasses any genetic manipulation of the virus that slows down the process making the "personalized-vaccine approach" impossible.

The present invention also makes it possible to discover novel immunogenic tumor-specific peptides.

In addition to cancer therapy, the coated adenovirus of the present invention can be used for treating any other diseases in a situation where a higher and peptide-specific immune response is needed (e.g. infectious diseases).

The present invention relates to a method of stimulating a peptide-specific immune response in a subject in need thereof, wherein the method comprises administration of adenoviral vectors comprising polypeptides attached onto the viral capsid to the subject. The present invention also relates to a method of stimulating a peptide-specific immune response in a subject in need thereof, wherein the method comprises administration of adenoviral vectors comprising polypeptides attached onto the viral capsid to the subject, wherein the polypeptides have not been genetically encoded by said adenoviral vector.

The present invention further relates to an adenoviral vector comprising polypeptides attached onto the viral capsid for use in stimulating a peptide-specific immune response in a subject. The present invention also relates to an adenoviral vector comprising polypeptides attached onto the viral capsid for use in stimulating a peptide-specific immune response in a subject, wherein the polypeptides have not been genetically encoded by said adenoviral vector.

The present invention further relates to a method of treating cancer or infectious disease in a subject in need thereof, wherein the method comprises administration of adenoviral vectors comprising polypeptides, which are capable of stimulating a peptide-specific immune response in the subject and which have been attached onto the viral capsid, to the subject. The present invention also relates to a method of treating cancer or infectious diseases in a subject in need thereof, wherein the method comprises administration of adenoviral vectors comprising polypeptides, which are capable of stimulating a peptide-specific immune response in the subject and have been attached onto the viral capsid, to the subject, wherein the polypeptides have not been genetically encoded by said adenoviral vector. The present invention also relates to a method of prophylaxis in infectious disease prevention.

Also, the present invention relates to an adenoviral vector comprising polypeptides, which are capable of stimulating a peptide-specific immune response in a subject and which have been attached onto the viral capsid, for use in treating cancer or an infectious disease in a subject. The present invention also relates to an adenoviral vector comprising polypeptides, which are capable of stimulating a peptide-specific immune response in a subject and which have been attached onto the viral capsid, for use in treating cancer or an infectious disease in a subject, wherein the polypeptides have not been genetically encoded by said adenoviral vector.

Furthermore, the present invention relates to an adenoviral vector, wherein the viral capsid has been attached with polypeptides and wherein the adenoviral vector attached with polypeptides is capable of stimulating a peptide-specific immune response in a subject.

Furthermore, the present invention relates to a method of coating the capsid of an adenovirus, wherein said method comprises linking polypeptides, which are capable of stimulating a peptide-specific immune response in a subject, to the adenoviral capsid covalently or non-covalently. The present invention also relates to a method of modifying the capsid of an adenovirus, wherein said method comprises linking of polylysine-modified polypeptides to the adenoviral capsid covalently or non-covalently, wherein the modified adenoviral vector is capable of stimulating a peptide-specific immune response in a subject.

Still, the present invention relates to use of polypeptides (e.g. polylysine-modified polypeptides), which are capable of stimulating a peptide-specific immune response in a subject, for coating the capsid of an adenovirus by covalently or non-covalently attaching or linking the polypeptides to the capsid.

The adenoviral vector and methods of the invention are used for converting antiviral immunity into anti-peptide immunity. The modified viral vector of the invention causes anti-peptide response in a subject.

Still, the present invention relates to a pharmaceutical composition comprising the adenoviral vector of the invention.

And still, the present invention relates to a method for identifying tumor-specific and MHC-I-specific polypeptides from a subject, said method comprising i) infecting tumor cells of the subject with adenoviral vectors;
ii) infecting dendritic cells of the subject with adenoviral vectors;

iii) isolating MHC-I molecules from tumor cells of step i) and from dendritic cells of step ii) and identifying the MHC-I-associated polypeptides from both groups;

iv) isolating MHC-I molecules from uninfected tumor cells and identifying the MHC-I-associated polypeptides;

v) identifying those polypeptides which have been presented by the infected and uninfected tumors of steps iii) and iv) and dendritic cells of step iii).

BRIEF DESCRIPTION OF THE DRAWINGS

In the following the invention will be described in greater detail by means of preferred embodiments with reference to the attached drawings, in which

FIG. 5 shows a schematic representing the discovery of novel immunogenic tumor-associated MHCI restricted peptides. Different conditions allow us to match the peptides, which the tumor is expressing, with the peptide of the same tumor that dendritic cells are presenting. This is a key feature in the system to facilitate the identification of immunogenic peptides. A) Dendritic cells were pulsed with tumor oncolysate to allow tumor antigens presentation. B) Unpulsed dendritic cells were matured and analyzed. This serves as a control to subsequently eliminate the self-peptides presented by the DCs. C) Infected tumor cell line (the same as condition A) were infected with oncolytic adenovirus and analyzed before complete lysis (less than 48 h). This condition helps us to discriminate if the adenovirus has a significant impact on the quality of the tumor antigens presented. D) This is uninfected tumor which presents tumor antigens and self-peptides (of course these two can be the same) on MHCI.

FIG. 6A shows a schematic of OVA-specific coated viruses. In this case, as we know all the processed peptide of the chicken ovalbumin (OVA) we coated the virus with OVA specific immunogenic peptide (SIINFEKL) (SEQ ID NO: 1). Then we generated other coated viruses to be used as controls such as SIINFDL (SEQ ID NO: 2) (antagonist) and FILKSINE (SEQ ID NO: 3) (scramble) as well as uncoated viruses.

FIG. 6B schematically illustrates the study of II generation adenoviruses that are coated with different peptides (PeptiCRAd refers to an oncolytic adenovirus coated with peptides).

DETAILED DESCRIPTION

Tumor Immunology and the Immunopeptidome

Dendritic cells (DC) are bone marrow derived professional antigen presenting cells. DCs are optimal antigen presenting cells for presenting tumor antigen epitopes to CD8+ and CD4+ T cells[3]. Exogenous antigens can be loaded onto MHC class I for "cross-presentation" to CD8+ T cell[4]. Cross-presentation is a phenomenon whose outcome is determined by the activation status of the DCs[5]. In cancer cells, the extent of DC maturation that leads to tumor-antigen cross-presentation is usually very low due to the hostile tumor microenvironment and tumor-derived immunosuppression also at local lymph nodes. These obstacles can be overcome by oncolytic virotherapy, as tumor-destroying viruses both provide the necessary "danger signals" to drive DC activation and interfere with tumor immunosuppression to expose hidden immunogenic antigens[6-8].

Oncolytic adenoviruses, also known as Conditionally Replicating adenoviruses (CRAds), are genetically modified to replicate and kill only cancer cells[9,10]. It is known that virus-induced tumor apoptosis and/or necrosis leads to release of large amounts of tumor-associated proteins not normally accessible by antigen-presenting cells, which drives efficient cross-presentation by tumor-associated DCs in the tumor draining lymph nodes[11-13].

Figure 2:
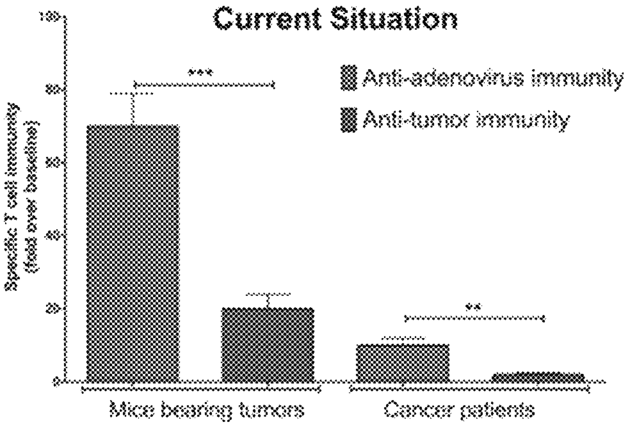
FIG. 2 shows immunodominance of anti-adenovirus response (left bar) vs tumor response (right bar). Mice) C57BL/6 mice bearing B16-OVA tumor were treated with PBS (Mock), Ad5D24 (unmodified oncolytic virus) and (Ad5D24-CpG, a more immunogenic oncolytic virus). T cells from the tumor were harvested and IFNgamma ELISPOT was performed to assess anti-tumor response and anti-adenovirus response. Cancer Patients) IFNgamma ELISPOT was performed on PBMCs from patients treated with an GMCSF-armed oncolytic adenovirus (Ad5D24-GMCSF)[15]. Ad5-derived peptides (anti-viral) and survivin-derived peptides (anti-tumor) were used to stimulate PBMCs before the ELISPOT.

Virus therapy of cancer has generally been found well tolerated, however, the overall treatment efficacy has remained modest; upon scrutiny of the immunological effects of virotherapy a clear dominance of virus over tumor has been observed in both mice and human (FIG. 2). Coating the adenovirus's capsid with synthetic MHC-I-restricted tumor-specific peptides will "trick" antigen presenting cells (APCs) to present these tumor antigens as part of the virus. In other words, the present invention utilizing adenovirus capsid as a scaffold to deliver MHC-I restricted peptides would shift the immune response away from the virus and instead toward the tumor.

As used herein "Major Histocompatibility Complex of class I" molecules refer to one of two primary classes of major histocompatibility complex (MHC) molecules (the other being MHC class II) and are found on nearly every nucleated cell of the body. Their function is to display fragments of proteins from within the cell to T cells; healthy cells will be ignored, while cells containing foreign proteins will be attacked by the immune system. Class I MHC molecules bind peptides generated mainly from degradation of cytosolic proteins by the proteasome. The MHC I:peptide complex is then inserted into the plasma membrane of the cell. The peptide is bound to the extracellular part of the class I MHC molecule. Thus, the function of the class I MHC is to display intracellular proteins to cytotoxic T cells (CTLs). However, class I MHC can also present peptides generated from exogenous proteins, in a process known as cross-presentation. As used herein "MHC-I-specific polypeptides" refer to those peptides, which are bound to MHC-I, i.e. the extracellular part of the class I MHC molecule, and displayed to CTLs.

Figure 3A:
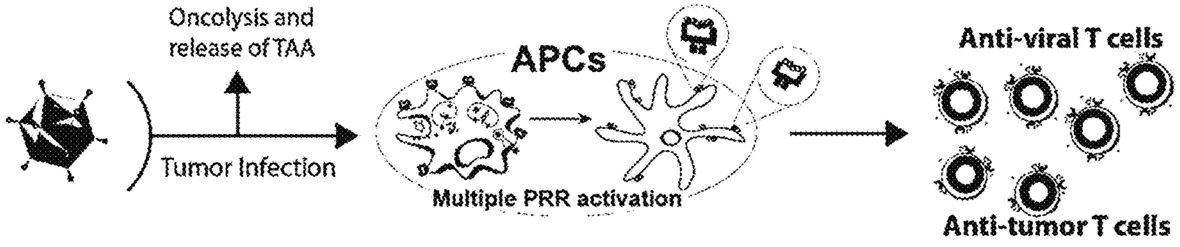
FIG. 3A reveals that oncolytic adenovirus has the ability to trigger APCs to present not only viral antigens (that leads to antiviral response) (another antigen presented on the cell of FIG. 3A) but also, as side effect, tumor antigens (another antigen presented on the cell of FIG. 3A) that leads to antitumor immunity. Anti-tumor T cells are marked as the two lowest cells of the T cell group.
Figure 3B:
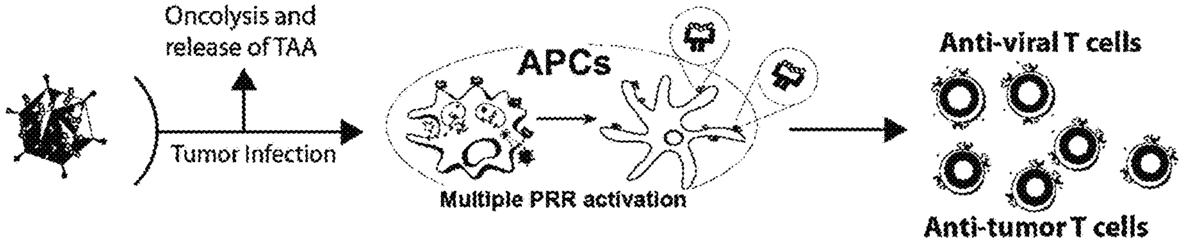
FIG. 3B reveals that the coated adenoviruses of the present invention will favor tumor antigen presentation (marked as both antigens presented on the cell of FIG. 3B) because its capsid is covered by MHC-I ready-to-use tumor-specific antigens (peptides). In this way the anti-capsid immunity can be reverted into anti-tumor immunity. Anti-tumor T cells are marked as the four lowest cells of the T cell group. As used herein APC refers to antigen presenting cells, TAA refers to tumor associated antigen and "PRR activation" refers to pattern recognition receptor activation. PRRs are proteins expressed by cells of the innate immune system to identify pathogen-associated molecular patterns, which are associated for example with microbial pathogens.

All the MHC-I peptides (MIPs) are collectively called the immunopeptidome[14]. Only recently, with the use of advanced technologies there has been the possibility to start looking into the MHC-I immunopeptidome. The crucial difference in the present invention, compared to other strategies attempting to broadly screen the whole immunopeptidome, is that the present invention focuses on specific peptides that are present simultaneously on tumor cells both before and after therapy (i.e. which will not be masked or edited away after therapy) and on DCs following therapy (FIG. 3).

Figure 4:
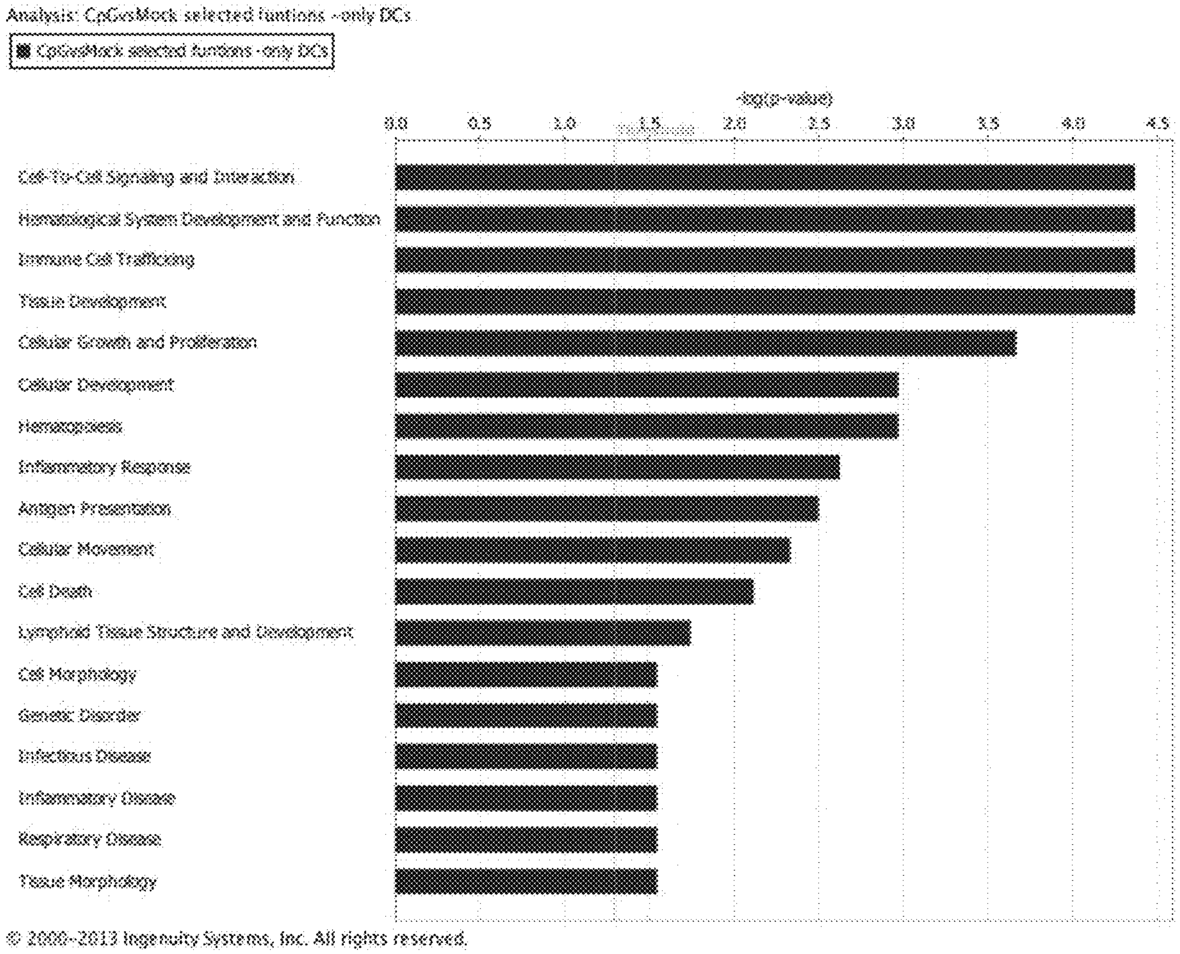
FIG. 4 shows the top upregulated Bio-Function networks of dendritic cells exposed to oncolytic adenovirus. Human primary dendritic cells were harvested and cultured for two weeks with IL4 and GMCSF. The cells were pulsed with an oncolytic adenovirus (Ad5D24) at 10VP/cell. 72 h later total RNA was collected, and analyzed on Agilent SurePrint G3 human 8×60 k (mRNA). Data were then analyzed with Ingenuity Pathway software.

A significant difference between the present invention and the traditional peptide-based immunotherapy is that the present invention takes full advantage of the fact that viruses, and in particular adenoviruses, have a privileged means to interact with DCs (hence there is no obligatory need to target DC). Adenoviruses stimulate several Pattern Recognition Receptors (PRRs), Toll-like Receptors[16,17], NOD-like receptor family[18] and inflammasome[19], predisposing DCs for robust antigen presentation and CTL activation[20]. To this purpose we show that human primary DCs pulsed with oncolytic adenovirus activate pathways involved in cellular adhesion, cell-cell interaction and signaling, maturation and antigen presentation suggesting that the adenovirus is capable of promoting maturation and migration of immature primary dendritic cells (FIG. 4).

As used herein "stimulating a peptide-specific immune response" refers to causing an immune response wherein cells representing the specific peptides will be attacked and destroyed. "Immune response" refers to a system involving lymphocytes (i.e. white blood cells), either T or B lymphocytes or the both. T lymphocytes attack antigens directly and help in controlling the immune response. They also release chemicals, known as cytokines, which control the entire immune response. B lymphocytes become cells that produce antibodies. Antibodies attach to a specific antigen and make it easier for the immune cells to destroy the antigen.

In one embodiment of the invention one or more polypeptides attached onto a viral capsid are selected from the group consisting of fragments of tyrosinase-related protein 2 (TRP-2), fragments of human melanoma antigen gp100 (hgp100), fragments of melanoma-associated antigen A1 (MAGE-A1), SIINFEKL (SEQ ID NO: 1), polyK-SIINFEKL, SIINFEKL-polyK, SLFRAVITK (SEQ ID NO: 4), polyK-SLFRAVITK, SLFRAVITK-polyK, SVYDFFVWL (SEQ ID NO: 5), polyK-SVYDFFVWL, SVYDFFVWL-polyK, KVPRNQDWL (SEQ ID NO: 6), polyK-KVPRNQDWL and KVPRNQDWL-polyK. In one embodiment of the invention one type or more polypeptides attached onto a viral capsid comprise SIINFEKL (SEQ ID NO: 1), SLFRAVITK (SEQ ID NO: 4), SVYDFFVWL (SEQ ID NO: 5) or KVPRNQDWL (SEQ ID NO: 6). In a further embodiment polypeptide fragments of TRP-2 and hgp100 (e.g. SVYDFFVWL or KVPRNQDWL) are attached onto the adenoviral capsid. In one embodiment of the invention the polypeptides used in the present invention are polylysine (polyK) modified. As used herein, polyK may be selected from the group consisting of 3K-15K, 3K-10K, 3K-8K, 5K-8K, 5K-7K and 6K. As used herein "polylysine-modified polypeptide" refers to a polypeptide, wherein a polylysine sequence has been inserted. Addition of a polylysine sequence to a polypeptide causes change in the charge of the peptide and the consequent absorption on the surface of the virus.

Adenoviral Vector

Figure 1:
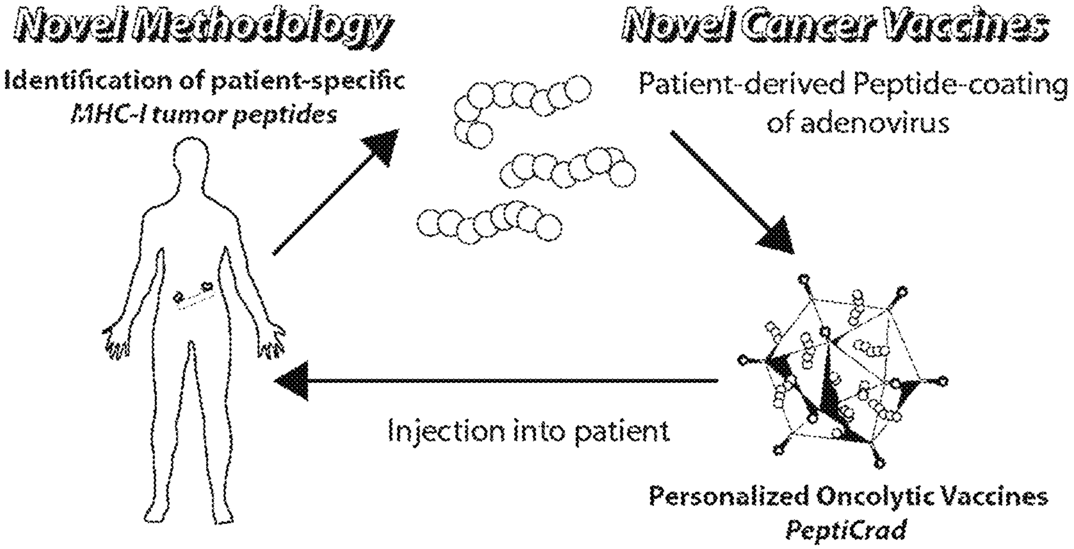
FIG. 1 shows a schematic of the present invention, wherein the modified adenovirus is capable of replicating and killing cancer cells while diverting the anti-viral immune response against the tumor.

Adenoviruses coated with peptides may be of any type and species of adenoviridae (e.g. not limited to human adenovirus). In one embodiment of the invention, the adenoviruses are capable of replicating and killing cancer cells while diverting the anti-viral immune response against the tumor (FIG. 1). The cancer destroying virus of the present invention coated with patient derived tumor-specific immune-activating peptides enhance and divert the anti-viral immunity into anti-tumor immunity.

The adenoviral vectors used in the present invention can be any adenoviral vectors suitable for treating a human or animal. Alternatively, various types of adenoviral vectors can be used according to the present invention. Also, the vectors may be modified in any way known in the art, e.g. by deleting, inserting, mutating or modifying any viral areas. The vectors can be made tumor specific with regard to replication. For example, the adenoviral vector may comprise modifications in E1, E3 and/or E4 such as insertion of tumor specific promoters, deletions of areas and insertion of transgenes.

In one embodiment of the invention, the adenoviral vector is an oncolytic adenoviral vector. As used herein "an oncolytic adenoviral vector" refers to an adenoviral vector capable of infecting and killing cancer cells by selective replication in tumor versus normal cells. In one embodiment of the invention the vectors are replication competent only in cells, which have defects in the Rb-pathway, specifically Rb-p16 pathway. These defective cells include all tumor cells in animals and humans. As used herein "defects in the Rb-pathway" refers to mutations and/or epigenetic changes in any genes or proteins of the pathway. A tumor specific oncolytic adenovirus may be engineered for example by deleting 24 base pairs (D24) of the constant region 2 (CR2) of E1. As used herein "D24" or "24 bp deletion" refers to a deletion of nucleotides corresponding to amino acids 122-129 of the vector according to Heise C. et al. (2000, Nature Med 6, 1134-1139). In one embodiment of the invention the adenoviral vector comprises the 24 bp deletion (oncolytic virus) or E1 gene deletion (second generation virus) or the vector is a Helper-dependent vector. E1 gene deletion may be partial or total deletion of the E1 region. As used herein "a Helper-dependent vector" refers to a vector, which does not include genes encoding the enzymes and/or structural proteins required for replication and therefore is dependent on the assistance of a helper virus in order to replicate.

The backbone of the adenoviral vector may be of any serotype. In one embodiment of the invention the serotype of the adenoviral vector backbone is selected from serotype 3 or 5. As used herein, "adenovirus serotype 5 (Ad5) nucleic acid backbone" refers to the genome of Ad5 and "adenovirus serotype 3 (Ad3) nucleic acid backbone" refers to the genome of Ad3.

Further, the vectors may be chimeric vectors, e.g. Ad5/3, Ad3/5 or Ad5/35 vectors. As an example, "Ad5/3 vector" refers to a chimeric vector having parts of both Ad5 and Ad3 vectors.

In one embodiment of the invention the adenoviral vector comprises a capsid modification (i.e. a modification in nucleotide sequences encoding proteins forming the capsid of the virus). "Capsid" of the adenovirus refers to the protein shell of a virus. The capsid consists of several oligomeric structural subunits made of proteins called protomers.

Furthermore, fiber knob areas of the vector can be modified. In one embodiment of the invention the adenoviral vector is Ad5/3 or Ad5/35 comprising an Ad5 nucleic acid backbone and a fiber knob selected from the group consisting of Ad3 fiber knob, Ad35 fiber knob, Ad5/3 chimeric fiber knob and Ad5/35 chimeric fiber knob.

In a specific embodiment of the invention the oncolytic adenoviral vector is based on an adenovirus serotype 5 (Ad5) nucleic acid backbone and comprises the D24 deletion, optionally a transgene and optionally a CpG site. In another embodiment, the oncolytic adenoviral vector is based on an adenovirus serotype 5 (Ad5) nucleic acid backbone and comprises modification of the capsid (e.g. Ad3 fiber knob), optionally the D24 deletion and optionally a transgene.

Insertion of exogenous elements may enhance effects of vectors in target cells. The use of exogenous tissue or tumor-specific promoters is common in recombinant vectors and they can also be utilized in the present invention. Suitable promoters are well known to a person skilled in the art and they include, but are not limited to, hTERT, CMV, E2F.

The adenoviral vector may also cause expression of any transgene(s) (e.g. granulocyte macrophage colony stimulating factor (GM-CSF)). In one embodiment of the invention, the adenoviral vector comprises one or more transgenes. One example of suitable transgenes is cytokines, which manipulate increased trafficking of immune cells at the site affected by the disease, e.g. tumor site. Cytokines used in the present invention can be selected from any known cytokines in the art. In one embodiment of the invention the transgene is selected from the group consisting of chemokines and cytokines and signal peptides for the recruitment or manipulation of the immunological stroma at the tumor site especially for what concerns T cells, dendritic cells, macrophages, natural killer cells. The viral vectors of the invention may code for either one or several transgenes, e.g. cytokines (e.g. two, three, four, five or more). The adenoviral vector may for example express monoclonal antibodies to specifically block immunological checkpoints (e.g. CTLA4, PD1, PDL1).

A transgene(s) may be placed to different positions of the adenoviral vector. The transgene may be placed for example into a partly or totally deleted E3 region, either under the E3 promoter or an exogenous promoter, or into a partly or totally deleted E1 region, either under the E1 promoter or an exogenous promoter.

In one embodiment of the invention the adenoviral vector for coating is Ad5D24, Ad5D24CpG or Ad5D24-GMCSF. In Ad5D24-GMCSF GM-CSF transgene is in the place of deleted E3 region (i.e. deleted 6.7K/gp19K) under the control of E3 promoter (Cerullo V et al. 2010, Cancer Research 70: 4297-4309). As used herein, CpG refers to CpG moieties added into the adenovirus genome to make the virus more immunostimulatory. The insertion of CpG-rich regions in the adenovirus backbone increase the capability of adenovirus to stimulate TLR9 in antigen presenting cells hence increasing T cell stimulation and maturation as well as NK activation (Nayak S, Herzog R W. Gene Ther. 2010 March; 17(3):295-304).

The viral vectors utilized in the present inventions may also comprise other modifications than described above. Any additional components or modifications may optionally be used but are not obligatory for the present invention.

Coating the Adenoviral Vector

According to the present invention the capsid of an adenovirus is coated with synthetic polypeptides or peptides, which are capable of stimulating a peptide-specific immune response in a subject. The polypeptides used for coating the adenoviral vectors have not been genetically encoded by said adenoviral vectors. Herein, the terms "polypeptide" and "peptide" are used interchangeably to refer to polymers of amino acids of any length.

The polypeptides can be attached to the capsid by any known suitable chemical or biochemical method. In one embodiment of the invention the peptides have been attached covalently or non-covalently onto the viral capsid. In another embodiment of the invention the polypeptides have been attached to the capsid by electrostatic, disulfide or amide bond linkage or co-delivered and attached to the capsid in a single nanoparticle. The nanoparticle(s) may also be attached covalently or non-covalently, e.g. by electrostatic, disulfide or amide bond linkage, to the capsid. As used herein, "nanoparticles" refer to any particles, which are between 1 and 100 nanometers in size. The electrostatic linkage strategy takes advantage of the fact that the adenovirus capsid has a negative net total charge, it implies a synthesis of positively charged peptides consisting of polylysine attached to a small linker that is attached to the peptide of interest. The first strategy has two potential advantages: 1) It is rapid (for example about 15-30 minutes at room temperature or about 20 min at room temperature), which can be a key feature in personalized drugs and 2) transduction of adenovirus complexed with cation polymers is significantly increased[26,29].

The polypeptides attached onto the viral capsid may be all the same peptides or different peptides selected from two or more types of different tumor antigens. In one embodiment of the invention the adenoviruses are coated with more than one type of peptides. The peptides can be for example different MHC-I specific polypeptides of the same antigen, MHC-I polypeptides from different antigens or a combination of MHC-I and MHC-II restricted peptides. In one embodiment of the invention the polypeptides attached onto the viral capsid are selected from the group consisting of Major Histocompatibility Complex of class I (MHC-I)-specific polypeptides (polypeptides binding MHC-I), Major Histocompatibility Complex of class II (MHC-II)-specific polypeptides (polypeptides binding MHC-II), disease specific polypeptides (polypeptides associated with a disease), tumor specific polypeptides (polypeptides associated with tumors or a specific tumor) and DC specific polypeptides (polypeptides binding DC). In a specific embodiment of the invention the polypeptides attached onto the viral capsid are tumor-specific MHC-I restricted peptides. These peptides may be isolated directly from the tumor of patients with a process depicted in FIG. 5. By utilizing the method of FIG.

5 the polypeptides to be attached onto the viral capsid may be simultaneously presented on the MHC-I of the tumor and from the DCs that have been fed with tumor oncolysate. As used herein "tumor specific polypeptides" refers to polypeptides that are presented by tumor cells. As used herein "DC specific polypeptides" refers to polypeptides that are presented by DCs. As used herein "disease 1 specific polypeptides" refers to polypeptides that are presented by cells having a disease phenotype or infected by the disease.

The polypeptides to be attached to the capsid of an adenoviral vector include any polypeptides which are at the same time presented by disease or tumor cells and dendritic cells of one patient (e.g. tumor antigens or peptides derived from them). Examples of suitable peptides include, but are not limited to gp100.

The concentration of polypeptides on the capsid may vary and in one embodiment of the invention, the polypeptides are at a concentration of at least 500 nM.

According to the present invention in the production of the patient-tailored polypeptide coated adenoviruses disease cell-derived or tumor-derived MHC-I-loaded peptides can be isolated and identified, synthesized and admixed on to the capsid of a DC-stimulating oncolytic adenovirus. However, the method comprises at least two steps. First, the most immunogenic polypeptides loaded on MHC-I are identified, and secondly, these polypeptides are loaded on the oncolytic adenovirus capsid.

Pharmaceutical Compositions

The present invention provides not only therapeutic methods and uses for treating disorders but also pharmaceutical compositions for use in said methods and therapeutic uses. Such pharmaceutical compositions comprise coated adenoviruses, either alone or in combination with other agents such as a therapeutically effective agent or agents and/or a pharmaceutically acceptable vehicle or vehicles.

A pharmaceutically acceptable vehicle may for example be selected from the group consisting of a pharmaceutically acceptable solvent, diluent, adjuvant, excipient, buffer, carrier, antiseptic, filling, stabilising agent and thickening agent. Optionally, any other components normally found in corresponding products may be included. In one embodiment of the invention the pharmaceutical composition comprises polypeptide coated adenoviruses and a pharmaceutically acceptable vehicle.

The pharmaceutical composition may be in any form, such as solid, semisolid or liquid form, suitable for administration. A formulation can be selected from the group consisting of, but not limited to, for example solutions, emulsions or suspensions. Means and methods for formulating the present pharmaceutical preparations are known to persons skilled in the art, and may be manufactured in a manner which is in itself known.

Therapies

Any disease or disorder, which can be treated, which progress can be slowed down or wherein the symptoms can be ameliorated by stimulating the peptide-specific immune response against the abnormal cells caused by the disease, is included within the scope of the present invention. In one embodiment of the invention peptide-specific immune response is selected from the group consisting of anti-tumor (against primary and/or secondary tumors), anti-cancer (against primary and/or secondary malignant neoplasia), anti-infection and anti-virus immune response. In these cases the immune response is directed against a tumor (including both malignant and benign tumors as well as primary and secondary tumors), cancer (i.e. either primary or secondary malignant neoplasia), infectious disease (e.g. malaria), viruses (in case of viral infection e.g. influenza, SARS-CoV or HIV) etc. correspondingly. For example any cancer can be a target of the coated adenovirus of the present invention. In one embodiment of the invention, the cancer is selected from the group consisting of nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

As used herein, the term "treatment" or "treating" refers to administration of at least coated adenoviral vectors or a pharmaceutical composition comprising coated adenoviral vectors to a subject. The term "treating", as well as words stemming therefrom, as used herein, do not necessarily imply 100% or complete treatment or increase. Rather, there are varying degrees of which one of ordinary skill in the art recognizes as having a potential benefit or therapeutic effect. In this respect, the present inventive methods and uses can provide any degree of treatment or prevention of a disease. Therefore, "treating" includes not only complete cure but also for example prophylaxis, amelioration, or alleviation of disorders or symptoms related to a disease in question, such as cancer, tumor, infectious disease or viral infection. Therapeutic effect may be assessed by any method known to a person skilled in the art, for example by monitoring the symptoms of a patient or disease markers in blood.

As used herein, the term "subject" refers to a subject, which is selected from the group consisting of an animal, a mammal or a human. In one embodiment of the invention, the subject is a human or an animal.

The adenovirus coated with polypeptides is administered to a subject in a therapeutically effective amount, which causes the peptide-specific immune response. As used herein, the term "therapeutically effective amount" refers to an amount of coated adenovirus with which the harmful effects of a disease or disorder (e.g. cancer) are, at a minimum, ameliorated. The harmful effects include any detectable or noticeable effects of a subject such as pain, dizziness or swelling.

Only one administration of coated adenoviral vectors or pharmaceutical composition of the invention may have therapeutic effects. On the other hand the treatment may contain several administrations. Adenoviral vectors or pharmaceutical composition may be administered for example from 1 to 10 times during 2, 3, 4, or 8 weeks, or during the treatment period. The length of the treatment period may vary, and for example may last from two to 12 months or more. In some cases it is also possible to use several treatment periods for one patient.

The effective dose of vectors depends on at least the subject in need of the treatment, type of the disease and stage of the disease. The dose may vary for example from about $1\times10^8$ viral particles (VP) to about $1\times10^{14}$ VP, specifically from about $1\times10^9$ VP to about $1\times10^{13}$ VP and more specifically from about $5\times10^9$ VP to about $1\times10^{12}$ VP.

Administration of the coated adenovirus can be conducted through any suitable method known to a person skilled in the art. In one embodiment of the invention, the administration of the adenoviral vectors is conducted through an intratumoral, intra-arterial, intravenous, intrapleural, intravesicular, intracavitary or peritoneal injection, or an oral administration. It is also possible to combine different routes of administration.

The coated adenoviruses may also be used together (simultaneously or sequentially) with other therapeutic agents or therapeutic methods or a combination of treatments. For example the method or use of the invention may further comprise radiotherapy, chemotherapy, administration of other drugs or any clinical operations.

Before classifying a human or animal patient as suitable for the therapy of the present invention, the clinician may examine a patient. Based on the results deviating from the normal and revealing a disease, such as cancer, the clinician may suggest methods or treatment of the present invention for a patient.

Identification of Specific Peptides for Coating

The present invention reveals a method for identifying at least tumor-specific and MHC-I-specific polypeptides from a subject. The method utilizes qualitative and quantitative study on MHC-I immunopeptidome of tumors and DCs exposed to tumor lysate, specifically in vitro. The methodology in short, summarized in FIG. 5, involves isolation of MHC I molecules from both tumor cells and DCs pulsed with oncolysate in vitro (virus infected tumor cells) and sequencing of the MHC-associated polypeptides by mass-spectrometry based technology. Immunologically relevant peptides will be presented by both, tumors and dendritic cells pulsed with tumor lysate. For example, the use of the OVA-expressing mouse model may facilitate the validation of the system, in fact well known immunogenic OVA derived peptides (e.g. SIINFEKL; SEQ ID NO: 1) result from the mouse experiments and may serve as positive control.

Tumor cells of a subject before and after in vitro adenoviral infection are used in the method in order to block those polypeptides which are displayed by the cell due to the viral infection. DCs pulsed with tumor oncolysate in vitro are also used in the method in order to allow presentation of tumor antigen. The advantage of using not only tumor but also DC pulsed with tumor oncolysate for the isolation of tumor specific peptides is to better identification of the immunological active peptides (only if a peptide is presented on both tumor and DC there will be an efficient immune response). Isolation of MHC-I molecules from the tumor cells and dendritic cells may be conducted by any suitable isolation method of the art. Thereafter, sequencing of the polypeptides can be carried out by any suitable mass-spectrometry based technology (e.g. LC-MS/MS) for identifying the MHC-associated peptides. The polypeptides presented both by tumors and dendritic cells can be identified by comparing the polypeptides presented by these cells. Common polypeptides in two groups i.e. polypeptides presented by DCs pulsed with lysate minus DCs not pulsed (to eliminate DC-self peptides) and polypeptides presented by virus-infected tumors and non-infected tumors (to eliminate virus-specific peptides) are suitable for coating the adenoviruses. Comparison of polypeptides can be carried out manually or by any bioinformatics method known to a person skilled in the art. Optionally, in vitro, ex vivo and/or in vivo validation can be performed for any specific polypeptide or a combination thereof. In one embodiment of the invention, in addition to isolating MHC-I molecules from infected and uninfected tumor cells as well as infected dendritic cells, the method further comprises isolating MHC-I molecules from uninfected dendritic cells and identifying the MHC-I-associated polypeptides; and identifying those polypeptides which have been presented by the infected and uninfected tumors of steps iii) and iv) and by the infected dendritic cells of step iii) but not by the uninfected dendritic cells. In a specific embodiment of the invention infection of tumor cells and DCs with adenoviral vectors takes place in vitro. Adenoviral vectors used for the method of the present invention can be any adenoviral vector, for example any one of these vectors described in the earlier chapters.

In one embodiment of the invention the method for identifying tumor-specific and MHC-I-specific polypeptides from a subject is used for selecting one or more tumor-specific and MHC-I-specific polypeptides for coating the adenoviral capsid. Any of these tumor-specific and MHC-I-specific polypeptides or a combination thereof can be used for coating.

It will be obvious to a person skilled in the art that, as the technology advances, the inventive concept can be implemented in various ways. The invention and its embodiments are not limited to the examples described above but may vary within the scope of the claims.

EXAMPLES

The following examples demonstrate at least analysis of the tumor MHC-I immunopeptidome for isolating and selecting tumor-specific polypeptides, generation and physical characterization of tumor-specific polypeptide-coated oncolytic adenoviruses, and characterization of the coated adenoviruses in animal models (e.g. i) therapeutic efficacy, ii) capacity to divert the anti-virus immunity into anti-tumor immunity and iii) capacity to recruit cells of the immune system and to promote T cell responses).

Oncolytic Adenovirus Preparation

All oncolytic adenoviruses (OAd) were generated and propagated using standard protocols, as previously described (8). Briefly, viruses were amplified by infecting 10 T175 flasks with 70-80% confluent A549 cells at a multiplicity of infection (MOI) of 30. Three days post-infection, the cells were collected and lysed through four freeze (−80 °C) and thaw (37 °C) cycles. Adenoviral particles were then separated from the cell debris and impurities by two ultracentrifugations (22,000 and 27,000 rpm) on CsCl gradients. The recovered bands were purified by overnight dialysis at 4 °C against A195 buffer with continuous stirring. Specifically, dialysis cassettes with a molecular weight cutoff of 10,000 kDa (Pierce, Life Technologies) were used. The purified viruses were recovered from the cassettes, aliquoted and stored at −80 °C.

The integrity of the adenoviral genome was assessed by PCR using primers specific for the E3 gene and the D24 deletion in the E1A gene.

The viral particle titer was determined using the spectrophotometric method, whereas the infectious titer was determined by immunocytochemical staining, as described elsewhere in this section. The protein concentration of the viral preparation was determined by the Bradford assay using Bio-Rad Protein Assay Dye Reagent Concentrate (Bio-Rad Laboratories, Hercules, CA, USA). All spectrophotometric readings were performed with a SPECTROstar Nano spectrophotometer (BMG Labtech, Ortenber, Germany).

All viruses used in this study have been previously reported: Ad5D24 is an adenovirus that features a 24-base-pair deletion (D24) in the E1A gene (9), Ad5D24-CpG is an OAd bearing a CpG-enriched genome in the E3 gene (30), and Ad5D24-GM-CSF is an OAd expressing GM-CSF under the control of the viral E3 promoter (8).

Analysis of the Tumor MHC-I Immunopeptidome to Isolate and Select Tumor-Specific Peptides Method 1a:

Mouse CD11c+-sorted bone morrow dendritic cells were harvested from C57BL/6 mice and cultured for 1 week[23]. Cells were then exposed to:

A) PBS as control,

B) Oncolysate from B16-OVA cells (the oncolysate comes from B16-OVA cells infected with oncolytic adenovirus Ad5D24 until their complete lysis), C) B16-OVA cell lysate obtained by freezing and thawing of the cells.

At different time points MHC-I loaded with peptides were isolated from viable DCs using mild acid elution[25]. At the time of the analysis, peptides were dissolved in aqueous solution and analyzed by nano LC-MS/MS on a LTQ-Orbitrap Elite mass spectrometer (Thermo Fisher Scientific). Database searches were performed against the international protein Index mouse database version 3.23 containing 51536 sequences and 24497860 residues, www.ebi.ac.uk/IPI/IPI-help.html). Relevant peptides were in the group formed by the peptides that are commonly present in both the groups. DC-pulsed with lysate minus DC-not pulsed (to eliminate DC-self peptides) and B16-OVA virus-infected minus B16-OVA-non infected (to eliminate virus-specific peptides).

Method 1b:

We first reduced the complexity of the immunopeptidome of Method 1a in silico. Prediction of MHC-I class peptides (www.syfpeithi.de/home.htm). Functional annotation of the proteins (david.abcc.ncifcrf.gov) and (www.ingenuity.com) were used.

Oncomine analysis (www.oncomine.org) was used to suggest the level of expression of a given protein in different human cancers and cell lines. Most importantly, we validated our peptides using an epitope tool predictor ([17]).

Experimentally, to select the most immunogenic peptides we used a mouse IFN-gamma ELISPOT (Mabtech AB, Sweden) on splenocytes, tumors and lymph nodes harvested from C57BL/6 mice and pulsed with all the different peptides isolated from method 1a.

Briefly, C57BL/6 mice bearing B16-OVA tumors were treated with oncolytic adenovirus (Ad5D24). One to two weeks after treatment, mice were euthanized and organs and tumors were harvested and reduced to a single cell suspension for the IFN-gamma ELISPOT analysis (Mabtech, Palo Alto CA). Subsequently, once we had identified a pool of a few of the most immunogenic peptides we generated custom tetramer or Pentamer (Proimmune, UK) for flow cytometer-based detection of specific CD8 T cells recognizing these peptides on MHC-I molecules.

Generation and Physical Characterization of Tumor-Specific Peptide-Coated Oncolytic Adenoviruses Because OVA-derived peptides are very well known, as proof-of-concept we first generated an OVA-specific coated virus (FIG. 6). More specifically, we generated a SIINFEKL-coated adenovirus (SIINFEKL (SEQ ID NO: 1) is the most immunogenic OVA derived peptide); a SIINFEDL-coated virus (SIINFEDL (SEQ ID NO: 7) is an antagonist of SIINFEKL peptide); a FILKSINE-coated virus (FILKSINE (SEQ ID NO: 3) is a scramble peptide of SIINFEKL).

Figure 7:
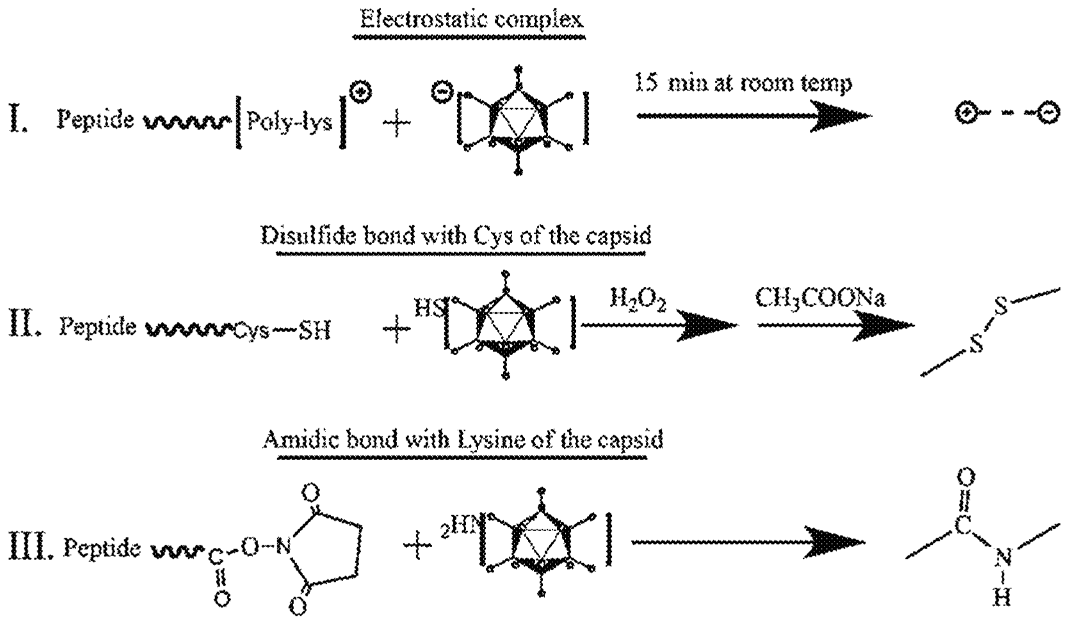
FIG. 7 shows a schematic representing three different strategies to generate the peptide-coated oncolytic adenovirus.

Method 2a:

In order to generate a peptide-coated oncolytic adenovirus different strategies were taken into account (FIG. 7).

One will use electrostatic binding between the virus and the peptides and two others will involve covalent bonds between virus and peptides.

I. Electrostatic interaction. Positively charged peptides complexed with negative virus capsid[26].

II. Covalent bond. Disulphide bond with the cysteine of the protein of the capsid[27,28].

III. Covalent bond. Amidic bond. Succinimidyl ester reaction with amine groups of Lysine of capsid[28].

The methods of linking are described in the corresponding reference documents.

In one embodiment of the invention peptide-coated oncolytic adenoviruses were prepared as follows:

PeptiCRAd Complex Formation

All PeptiCRAd complexes described in this work were prepared by mixing oncolytic viruses (as described under the title "Oncolytic adenovirus preparation") and polyK-epitopes at a 1:500 ratio (see FIGS. 8A and 12) according to the following protocol: i) for each microliter of viral preparation used, the corresponding number of micrograms of protein present was calculated; ii) then, for each microgram of viral protein, 500 μg of peptide was added; iii) after vortexing, the mixture was incubated at room temperature (RT) for 15 min; and iv) the solution was vortexed and used for assays or animal injections. New PeptiCRAds were prepared before each experiment using fresh reagents. All dilutions of virus and peptides required before incubation were performed in sterile Milli-Q water adjusted to pH 7.4. The PeptiCRAds were then diluted with the buffer required by the assay.

Method 2b:

Infectivity of this peptide coated virus from Method 2a was assessed in vitro by luciferase assay and by qPCR in different cell lines (human and murine)[30]. To assess infectivity, a panel of different tumor cell lines with different levels of expression of CAR were infected with different concentrations of coated virus expressing luciferase (Ad5D24-Luc) (1, 10, 100, 1000 VP/cell); uncoated virus was always used as control. At different time points luciferase expression was quantified. Simultaneously, total DNA was harvested and viral DNA replication was quantified by qPCR. Oncolytic activity in vitro was tested by TCID50 and MTS assays[31].

In one embodiment of the invention, the infectivity was studied by ICC as follows:

Infectivity Assay by ICC

Tumor cells were seeded at $2.0\times10^5$ cells per well on 24-well plates in 3 or 5 replicates. The following day, the cells were infected with 100 μl of viral dilutions. The plates were then centrifuged for 90 min at 1,000 rcf at 37 °C, followed by incubation for 48 h. After the incubation period, the culture media were removed, and the cells were fixed by incubation with 250 μl of ice-cold methanol for 15 min. Once the methanol was removed, the cells were washed 3 times with 300 μl of PBS supplemented with 1% bovine serum albumin (BSA). The cells were then stained with 250 μl of mouse monoclonal anti-hexon antibody (Novus Biologicals, Littleton, CO, USA), diluted 1:2,000, for 1 h at RT in the dark. The cells were then washed and stained with 250 μl of biotin-streptavidin-conjugated goat anti-mouse antibody, diluted 1:500 with PBS/1% BSA, for 1 h at RT in the dark. The cells were subsequently incubated with 250 μl of extravidin-peroxidase (Sigma-Aldrich, St. Louis, MO, USA), diluted 1:200, for 30 min at RT. The cells were washed extensively, and DAB staining solution (Sigma-Aldrich, St. Louis, MO, USA) was prepared according to the manufacturer's instructions. A total of 250 μl of DAB staining solution was then applied to each well, and the cells were monitored under a microscope for the appearance of dark spots. When the optimal signal-to-noise ratio was reached, the reaction was quenched by the addition of PBS/1% BSA (500 μl per well). For each replicate (i.e., well), 5 images of non-overlapping fields were acquired using an AMG EVOS XL microscope (AMG group, Life Technologies). The following formula was used to determine the infectious titer:

$$\text{Infectious titer} = x * \frac{\text{well area}}{\text{field area}} * \frac{1}{\text{dilution factor}} * \frac{1\text{ ml}}{\text{Volume of dilution applied}}$$

For the infectivity comparisons, the data are presented as the average number of spots in each field.

Figure 8A:
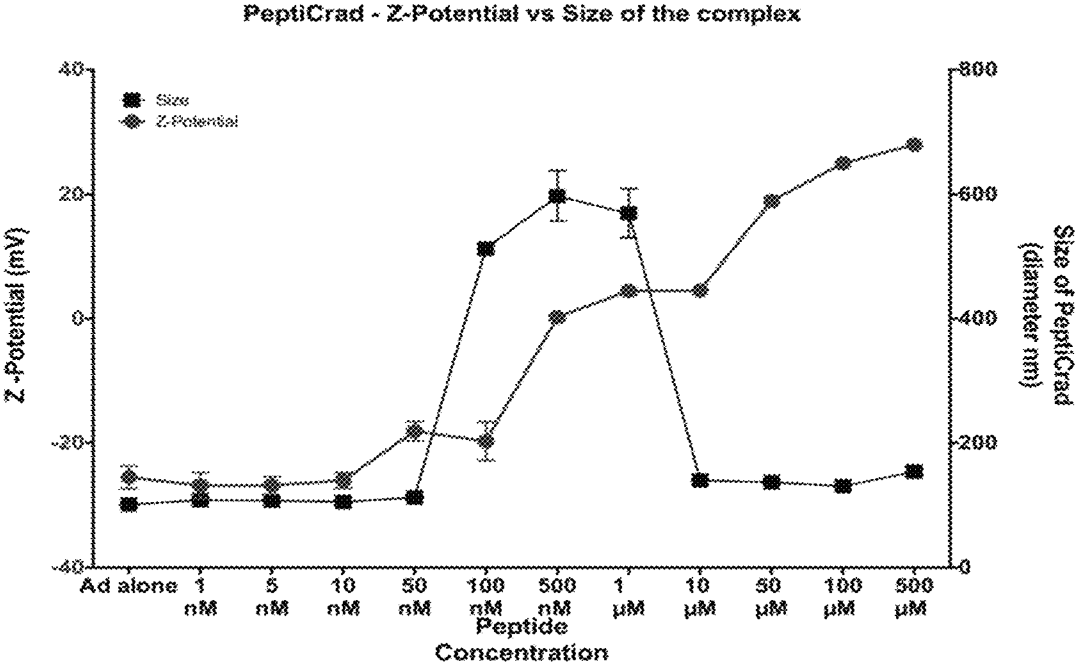
FIG. 8A shows a complex formation between Ad5D24 oncolytic adenovirus and tumor-specific peptides ("Z-potential" line). $1\times10^{10}$ viral particles were conjugated with different concentration of positively charged tumor-specific peptide. After the reaction Z-potential of the single particles was measured ("Size" line). $1\times10^{10}$ viral particles were conjugated with different concentration of positively charged tumor-specific peptide. After, the size of the single particles was measured and reported in function of the peptide concentration. When the Z-potential is between −20 mV and +20 mV there is a drastic change in size of the complex showing high degree of polydispersity (likely virus aggregation), but this state returned to normality at higher concentration of peptides suggesting that the complex (PeptiCRAd) is completed coated with no possibility to form dipole that promotes the formation of the aggregates (high polydispersity).
Figure 12:
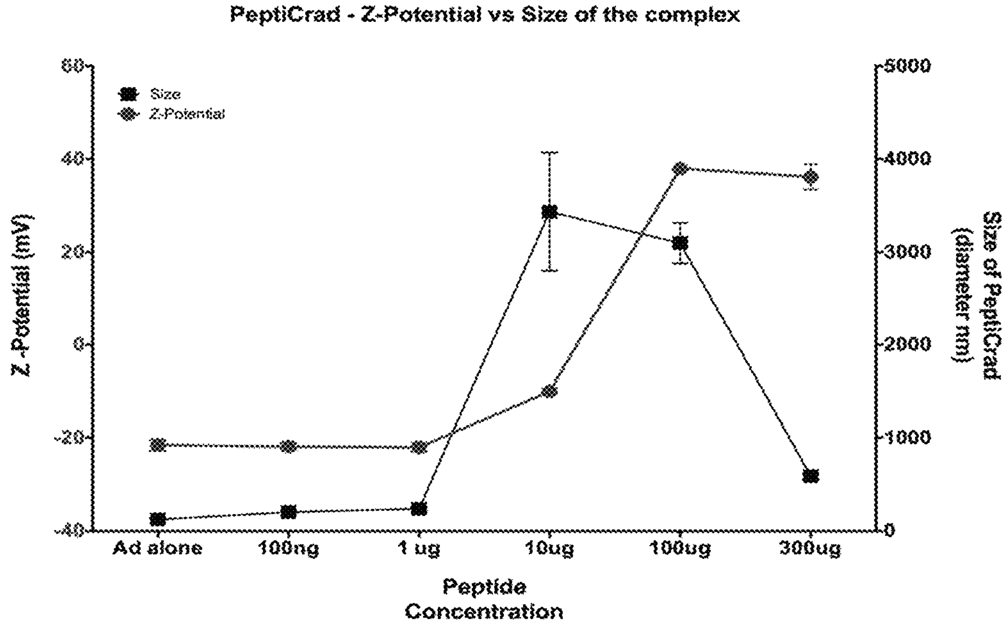
FIG. 12 shows the correlation between net charge of PeptiCRAd and its size. In this example we started with a naked virus (net charge about −25-30 mV) and then adding increasing concentration of peptides to form the complex we call PeptiCRAd. It shows that the more peptides we added the more the net charge of the virus changed from negative to positive values, at the end, when the complex PeptiCRAd was formed the net charge of the virus coated with the peptide was about +30-35 mV.

In Support of Methods 2:

The negatively charged adenovirus capsid was coated electrostatically with tumor specific peptide. This complex had a variation in Z-potential that is proportional to the amount of peptides. This change of Z-potential showed that positively charged peptides were binding the viral capsid determining the inversion of charge (FIG. 8A line with dots). Once all the negative charges of the capsid had been saturated, the Z-potential seemed to rich a plateau (FIG. 12 line with circle). Uniform monodispersed complex can be formed with concentration of polypeptides more than 500 nM for proceeding to in vitro and in vivo efficacy.

Figure 9:
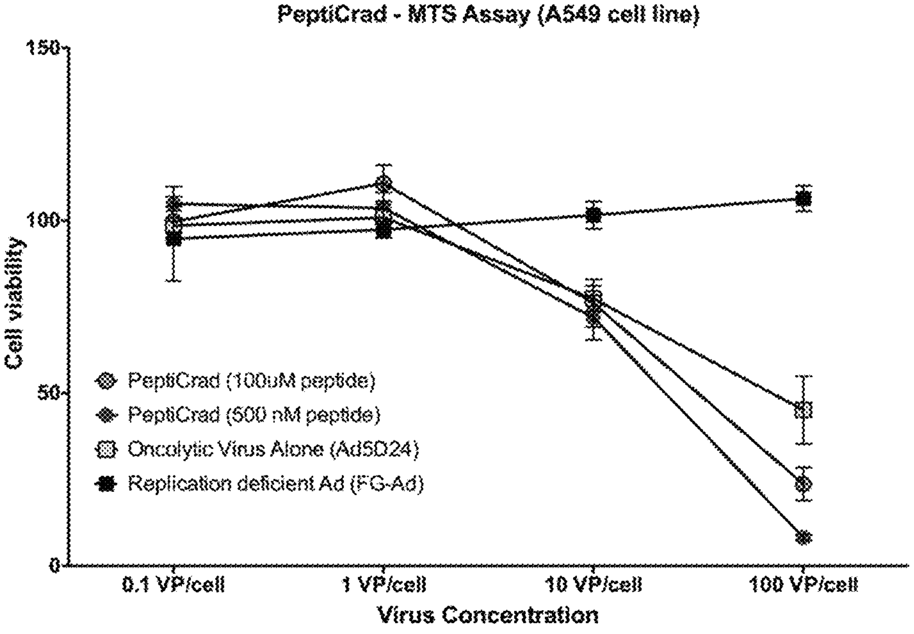
FIG. 9 shows that the coated adenovirus Ad5D24 of the present invention (PeptiCRAd) displays an enhanced cell killing activity compared to uncoated oncolytic virus. Representative cell viability assay (MTS assay) performed on lung cancer adenocarcinoma cell line (A549). Cells were seeded on day 0, infected at indicated multiplicity of infection on day 1 and the test was stopped and analyzed on day 3.

To further characterize the peptide coated adenovirus complex we performed several viability assays (MTS assay) comparing the efficacy of cell killing of PeptiCRAd with uncoated oncolytic virus (FIG. 9). The results indicate that the coating of the virus constantly result in unaltered or better cell killing activity compared with uncoated oncolytic viruses.

In one embodiment of the invention the viability assay was carried out as follows:

Viability Assay

Tumor cells were seeded at $1.0\times10^4$ cells per well on 96-well plates in growth media with 5% FBS. The next day, the media were removed, and 50 μl of virus, diluted in growth media with 2% FBS, was used to infect the cells for 2 h at 37 °C. Afterwards, 100 μl of growth media with 5% FBS was added, and the cells were again incubated at 37 °C. The growth media were changed every other day. When the most infective conditions (100 vp/cell) showed an extensive cytopathic effect (>90%), cell viability was determined by MTS assay according to the manufacturer's protocol (Cell-Titer 96 AQueous One Solution Cell Proliferation Assay; Promega, Nacka, Sweden). Spectrophotometric data were acquired with Varioskan Flash Multimode Reader (Thermo Scientific, Carlsbad, CA, USA).

Study Design

The sample size was determined using the following equation:

$$n = 1 + 2C\left(\frac{s}{d}\right)^2$$

where C is a constant based on α and β values, s is the estimated variability and d is the effect to be observed (34). For all of the animal experiments, a power (1-β) of at least 80% and a significance (α) of 0.05 were considered. The rules for stopping the data collection were i) death of more than 60% of the mice in one or more groups and ii) total clearance of the tumors. All of the mice that died before the end of the experiment were excluded from the growth curves to preserve the statistical integrity of the analysis.

The objective of the research was to use melanoma models to test whether OAds could represent a valid adjuvant for a peptide cancer-vaccine approach. Additionally, two specific questions were posed: i) Can PeptiCRAd limit the growth of distant, untreated tumors?ii) Can the efficacy of PeptiCRAd be enhanced by targeting multiple tumor antigens instead of a single one? To answer these questions, we utilized immunocompetent or humanized mice bearing melanoma tumors. The mice were randomly assigned to each experimental group, and no blinding was adopted.

Cell Lines, Reagents and Human Samples

The human lung carcinoma cell line A549, the human colorectal adenocarcinoma cell line CACO-2, the human malignant melanoma cell line SK-MEL-2, the human melanoma cell line HS294T and the mouse melanoma cell line B16-F10 were purchased from the American Type Culture Collection (ATCC; Manassas, VA, USA). The cell line B16-OVA (35), a mouse melanoma cell line expressing chicken OVA, was kindly provided by Prof Richard Vile (Mayo Clinic, Rochester, MN, USA).

The A549, CACO-2 and B16-OVA cell lines were cultured in low-glucose DMEM (Lonza, Basel, Switzerland), the HS294T cell line was cultured in high-glucose DMEM (Gibco, Life Technologies, Carlsbad, CA, USA), the SK-MEL-2 cell line was cultured in EMEM (ATCC), and the B16-F10 cell line was cultured in RPMI-1640 (Gibco, Life Technologies). All media were supplemented with 10% fetal bovine serum (FBS; Gibco, Life Technologies), 2 mM GlutaMAX (Gibco, Life Technologies), and 100 U/ml penicillin and 0.1 mg/ml streptomycin (Gibco, Life Technologies). The B16-OVA cell line was also cultured in the presence of 5 mg/ml Geneticin (Gibco, Life Technologies) to ensure the selection of OVA-expressing cells. During the culture period or when needed for assays, the cells were washed with 1× phosphate-buffered saline (PBS) and detached by incubation with 1× TrypLE Express (Gibco, Life Technologies) for 3 min at 37 °C.

SIINFEKL ($OVA_{257-264}$), polyK-SIINFEKL, SIINFEKL-polyK, polyK-AHX-SIINFEKL, polyK-SVYDFFVWL ($TRP\text{-}2_{180-188}$), polyK-KVPRNQDWL ($hgp100_{25-33}$) and polyK-SLFRAVITK ($MAGE\text{-}A1_{96-104}$) peptides were purchased from Zhejiang Ontores Biotechnologies Co. (Zhejiang, China). The purity of all peptides was estimated to be >80%, and they were analyzed by mass spectral analysis.

In the examples chapter polyK refers to 6K.

The net charge of peptides was calculated by the Peptide Property Calculator Ver. 3.1 online tool (biosyn.com/PeptidePropertyCalculator/PeptidePropertyCalculator.aspx).

The genotype of the SK-MEL-2 cell line was HLA-A*03-*26; B*35-*38; C*04-*12. Buffy coat from a healthy donor was also obtained from the Finnish Red Cross service, and the genotype was determined as HLA-A*03-*03; B*07-*27; C*01-*07

Characterization of Coated Adenoviruses in Animal Models

Method 3a:

We tested in vivo the efficacy, immunogenicity, toxicity, biodistribution of the coated-viruses vs uncoated regular oncolytic viruses. Efficacy and immunogenicity were tested in C57BL/6 mice bearing B16-OVA tumors. The SIINFEKL-coated virus presented a more robust anti-OVA response that translated into a more prominent tumor control (efficacy), compared with other coated viruses (antagonist, scramble and uncoated). Simultaneously, through adaptive transfer of radiolabeled cells (DCs and T cells) the trafficking of these cells to the tumor microenvironment was also assessed. Finally, toxicity and biodistribution of the modified adenoviral vector was also studied.

To study the efficacy of the coated viruses, different groups of C57BL/6 mice (N=15 per group) bearing syngeneic B16-OVA tumors (two tumors per mouse) were treated as follows: a) SIINFEKL-coated virus b) SIINFEDL-coated virus c) FILKSINE-coated virus and d) uncoated virus as control. At different time points starting from 3 days after the administration of the virus, two mice per group was euthanized and spleen, lymph nodes and tumor were harvested into a single cell suspension for ELISPOT, co-culture and flow cytometry analysis. Simultaneously tumor growth was measured with standard caliper over time. Flow cytometry analysis revealed directly the quantity of SIINFEKL-specific T cells in the tumor, in the spleen and in the lymph nodes (tumor draining and not). For this analysis we used SIINFEKL-specific pentamers (e.g. 31). Mouse IFN-gamma ELISPOT also gave us quantitative indication of anti-OVA (anti-SIINFEKL) T cell activation. In the co-culture experiment we tested in vitro the capability of T cells (harvested from experimental mice) to kill B16 and B16-OVA. Cells were co-cultured at different cell:target ratios and B16 and B16-OVA viability was assessed by MTS or MTT assay. In all this experiment T cell harvested from OT-I mice was used as control. CMT64-OVA model, which is a murine tumor expressing OVA where the human adenovirus is semi-permissive[33], was also used.

Method 3b:

The anti-tumor activity and immunogenicity of a virus coated with: i) OVA-peptide (SIINFEKL (SEQ ID NO: 1)), ii) B16 peptide TRP2 (SVYDFFVWL (SEQ ID NO: 5)), iii) hgp100 peptide (KVPRNQDWL (SEQ ID NO: 6)) or iv) new peptides identified in method 1 were compared.

These viruses were tested for their efficacy and capacity to induce an anti-tumor immune response. Anti-viral response was compared with the anti-tumor response (ELISPOT and Pentamer analysis). The capacity to induce an immune response to a different epitope (e.g. OVA-virus trigger a TRP2 response, epitope spreading) was also assessed. Methods used in this method have already been described in method 3a.

Figure 10A:
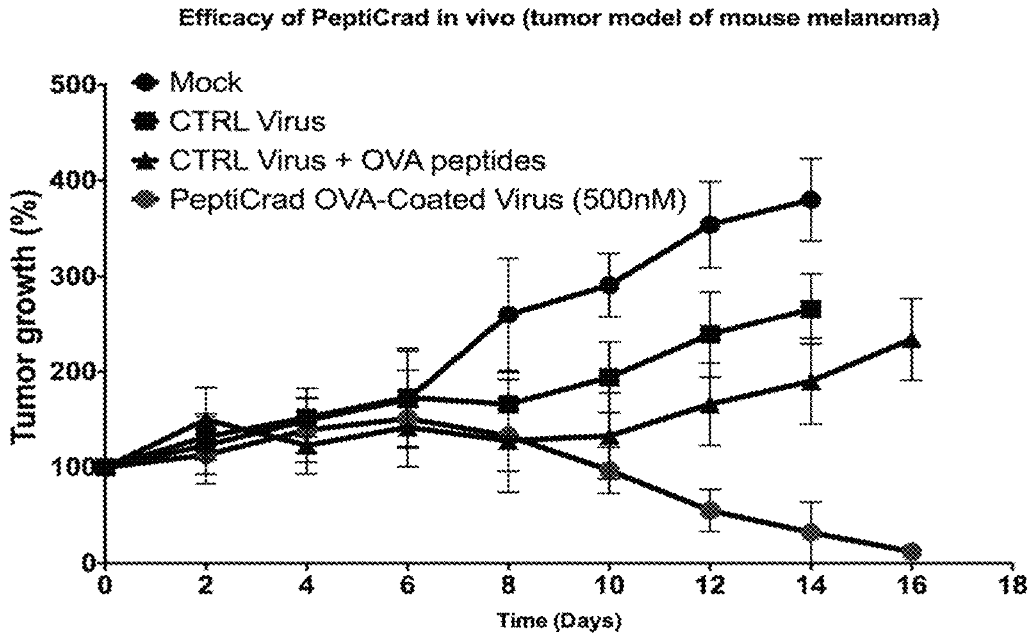
FIG. 10A shows that OVA-specific adenovirus enhances the OVA-specific immunity. Mice bearing subcutaneous B16-OVA tumors were intratumorally injected with: PBS, Oncolytic virus (Ad5D24), Oncolytic virus+SIINFEKL (SEQ ID NO: 1) peptides (Not complexed), Oncolytic virus+SIINFEKL (SEQ ID NO: 1; Complexed as single entity, PeptiCRAd). Tumor growth was measured and reported at shown time points.
Figure 10B:
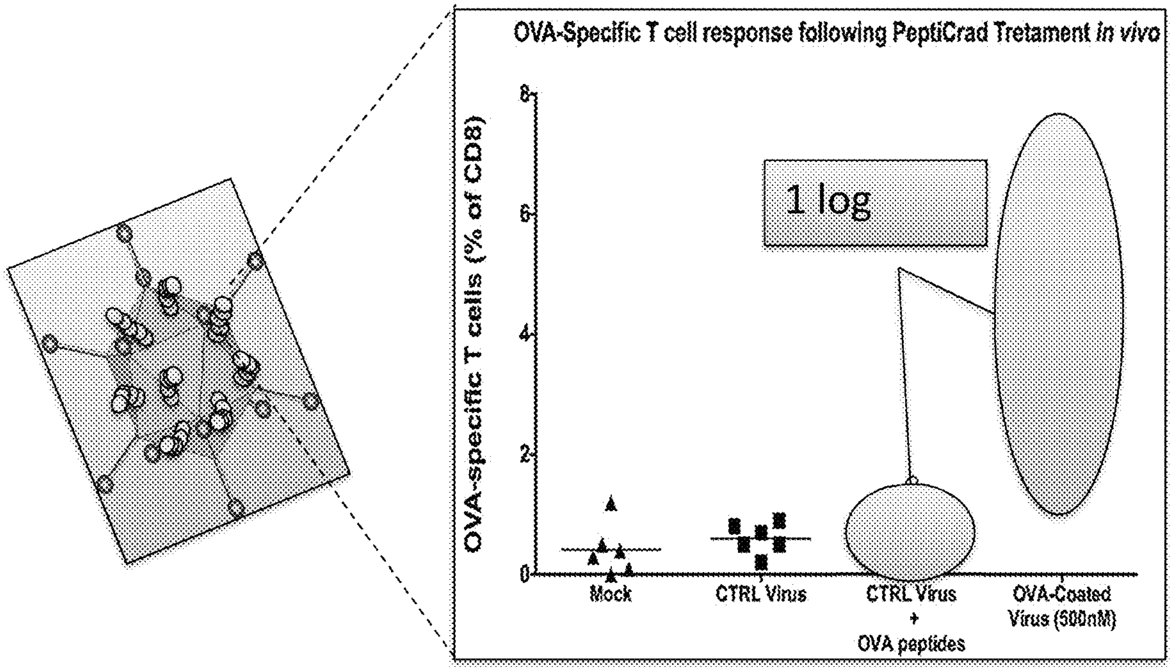
FIG. 10B illustrates SIINFEKL (SEQ ID NO: 1) specific immunity, assessed by flow cytometry (pentamer analysis).

Studies Based on Methods 2 and 3:

We generated an OVA-specific PeptiCRAd (SIINFEKL-coated oncolytic adenovirus) as described in FIG. 7 strategy I. Briefly, synthetic SIINFEKL peptides were synthesized and attached to a poly-lysine linker (polyK-SIINFEKL) to confer to the peptides a positive net charge and complexed with naked virus that has a negative net charge, 30 minutes prior injection. The complex was then intratumorally administered to mice bearing subcutaneous B16-OVA tumors. Tumor growth was monitored and at the end of the experiment mice were euthanized, tumors were collected and OVA-specific T cells were quantified by flow cytometry (FIG. 10).

This experiment demonstrates the superiority of the modified adenoviral vector of the present invention compared to virus alone and to virus and peptides administered separately. It also shows the importance of the correct formulation of the coated virus, as with higher concentrations of peptides it seems to induce less tumor specific T cells (data not shown).

Second Generation Coated Adenoviruses

Method 4:

Second Generation PeptiCRAd were generated by coating oncolytic viruses with more than a single peptide to elicit a more robust and polyvalent immune response. These new viruses were characterized as in Method 2 and the efficacy was assessed as described in method 3. Subsequently, we coated a cytokine-armed oncolytic adenovirus with several types of polypeptides. The polypeptides can either be different MHC-I specific peptides of the same antigen, or MHC-I peptides from different antigens, or a combination of MHC-I and MHC-II restricted peptides.

Methods Used for Analyzing Coated Oncolytic Viruses

Zeta Potential and Dynamic Light Scattering (DLS) Analysis

Coated oncolytic virus samples were prepared as described under the title "PeptiCRAdcomplex formation". Each sample was then vortexed and diluted to a final volume of 700 μl with sterile Milli-Q water adjusted to pH 7.4, after which the sample was transferred to a polystyrene disposable cuvette to determine the size of the complexes. The sample was then recovered from the cuvette and transferred to a DTS1070 disposable capillary cell (Malvern, Worcestershire, UK) for zeta potential measurements. All measurements were performed at 25 °C with a Zetasizer Nano ZS (Malvern).

SPR

The interaction of polyK-SIINFEKL or SIINFEKL with OAds was evaluated using SPR. Measurements were performed using a multi-parametric SPR Navi™ 220A instrument (Bionavis Ltd, Tampere, Finland). This instrument comprises a temperature-controlled dual flow channel with an integrated fluidic system and an auto-sampler for buffer and sample handling. Milli-Q water with its pH adjusted to 7.4 was used as a running buffer. Additionally, a constant flow rate of 30 μl/min was used throughout the experiments, and temperature was set to +20 °C. Laser light with a wavelength of 670 nm was used for surface plasmon excitation.

Prior to the SPR experiment; a sensor slide with a silicon dioxide surface was activated by 3 min of plasma treatment followed by coating with APTES ((3-aminopropyl)triethoxysilane) by incubating the sensor in 50 mM APTES in toluene solution for 1 h. The sensor was then placed into the SPR device, and the OAds were immobilized in situ on the sensor surface of the test channel by injecting 50 μg/ml OAds in Milli-Q water (pH 7.4) for approximately 12 min, followed by a 3 min wash with 20 mM CHAPS (3-[(3-cholamidopropyl)dimethylammonio]-1-propanesulfonate). The second flow channel was used as a reference and was injected with Milli-Q water (pH 7.4), followed by washing with CHAPS. The baseline was observed for at least 10 min before sample injections. PolyK-SIINFEKL or SIINFEKL was then injected into both flow channels of the flow cell in parallel, with increasing concentrations.

Cross-Presentation Experiment

Fresh spleens were collected from naïve C57BL/6 mice and forced through a 70-μm cell strainer (Fisher Scientific, Waltham, MA, USA). Red blood cells were lysed by incubating the samples with 5 ml of ACK lysis buffer (Life Technologies) for 5 min at RT. Afterwards, splenocytes were washed and prepared for the assay ($2\times10^6$ cells in 800 μl of 10% RPMI-1640 culture media for each condition tested). A total of 200 μl of SIINFEKL, polyK-SIINFEKL, SIINFEKL-polyK or SIINFEKL-AHX-polyK peptide dilution (0.19 μg/μl) was added to the splenocytes. To test OVA-PeptiCRAd, an infectious condition of 100 vp/cell was used (a total of $7.9\times10^9$ vp mixed with 37.5 μg of polyK-SIINFEKL in 200 μl of 10% RPMI-1640). The PeptiCRAd complex was prepared as described under Method 2. The splenocytes were then incubated for 2 h at 37 °C. Afterwards, the cells were extensively washed and stained with either APC anti-mouse H-2K$^b$ bound to SIINFEKL or APC Mouse IgG1, κ Isotype Ctrl (BioLegend, San Diego, CA, USA). After a 30-min incubation on ice, the samples were washed and analyzed by flow cytometry.

Flow Cytometry Analysis

The tumors, spleens and lymph nodes of treated mice were collected, forced through a 70-μm cell strainer and cultured overnight in 10% RPMI-1640 media. When necessary, the samples were frozen in RPMI-1640 (with 10% FBS and 10% DMSO) and stored at −80 °C. Single-cell suspensions were stained with fluorochrome-conjugated monoclonal antibodies and analyzed using a BD LSR II (BD Biosciences) or a Gallios (Beckman Coulter) flow cytometer and FlowJo software (Tree Star, Ashland, OR, USA). Sterile PBS was used as the staining buffer. Epitope-specific T cells were studied using MHC Class I Pentamers (ProImmune, Oxford, UK). Other antibodies used included the following: murine and human Fc block CD16/32 (BD Pharmingen); FITC anti-mouse CD8 and FITC anti-human CD8 (ProImmune); PE/Cy7 anti-mouse CD38, PE/Cy7 anti-mouse CD19, FITC anti-mouse CD11c, PerCp/Cy5.5 anti-mouse CD86, APC anti-mouse H-2K$^b$ bound to SIINFEKL and APC Mouse IgG1, κ Isotype Ctrl (BioLegend). All staining procedures were performed according to the manufacturer's recommendations.

Statistical Analyses

Statistical significance was determined using GraphPad Prism 6 (GraphPad Software, Inc., La Jolla, CA, USA). A detailed description of the statistical methods used to analyze the data from each experiment can be found in each Brief Description of the Drawing.

Animal Experiments and Ethical Issues

Animal experiments were done under the Finnish and European law and legislation. The animal permit (ESAVI/5924/04.10.03/2012) has been revised and accepted by the Finnish authorities (the Experimental Animal Committee of the University of Helsinki and the Provincial Government of Southern Finland). Fully immunocompetent C57BL/6 mice were obtained from Scanbur (Karlslunde, Denmark), and immunodeficient triple-knockout NOD.Cg-Prkdc$^{scid}$-IL2rg$^{tmlWjl}$/SzJ mice were obtained from Jackson Laboratories (Bar Harbor, ME, USA). All mice were purchased at 4-6 weeks of age and were quarantined for 2 weeks before the study. The mice were kept in cages with isolated and controlled airflow, and they had unlimited access to food during the entire study period. The health status of the mice was frequently monitored, and the animals were sacrificed at the first signs of pain or distress. All procedures were performed in a biosafety level 2 cabinet under sterile conditions.

For the efficacy experiments, tumor cells were collected at 60-70% confluence (logarithmic phase of growth) and were injected subcutaneously (s.c.) into the flanks of mice. The number of tumor cells injected into each flank varied according to the cell line type: $3\times10^5$ B16-OVA, $1\times10^5$ B16-F10, and $2\times10^6$ SK-MEL-2. In all experiments, three treatment injections were given. The tumor growth was then followed, and the tumor volume was determined using the formula.

According to our license, the humane endpoints were as follows: i) weight loss of 25%, ii) a tumor diameter>15 mm, and iii) evident signs of pain (reduced mobility or ulceration of the tumor). Euthanasia was performed by carbon dioxide inhalation followed by cervical dislocation.

High-Throughput Protocol

The high-throughput protocol was used to expand antigen-specific T cells from human peripheral blood mononuclear cells in vitro followed by peptide stimulation and detection of antigen-specific effector cytokine formation by IFN-gamma ELISpot.

Figure 18:
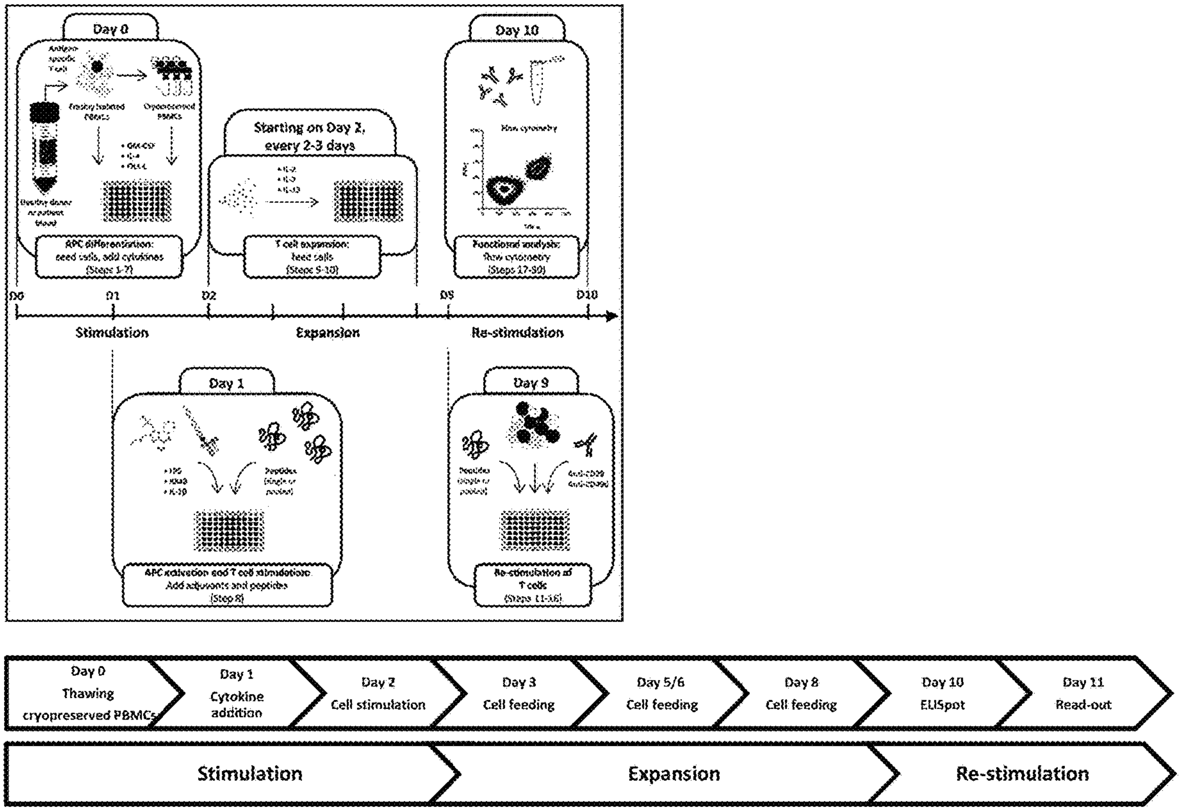
FIG. 18 shows the use of the technology to trigger the in vitro development of T cells that can recognize several infectious disease antigens. A sensitive, and high-throughput protocol was used to expand antigen-specific T cells from human peripheral blood mononuclear cells in vitro followed by peptide stimulation and detection of antigen-specific effector cytokine formation by IFN-gamma ELISpot. Briefly, PBMCs collected from healthy donors (HLA specific) were stimulated with: i) PeptiCRAd technology (non-replicating adenovirus, serotype 5, Ad5 complexed with polyK peptides), ii) virus alone (Ad5), iii)polyK peptides, and iv) peptides w/o polyK, to trigger the in vitro development of T cells that can recognize several infectious disease antigens. Four very different infectious diseases, so representing a broad range of infectious diseases (both viral and bacterial infections) were selected: COVID-19 (SARS-CoV-2, Coronaviridae), Hepatitis C (Hepatitis C virus (HCV), Flaviviridae), Tuberculosis (*Mycobacterium tuberculosis*, Mycobacteriaceae), Influenza (Influenza A, Orthomyxoviridae) (See Table 1). The presence and frequency of infectious disease antigen-specific T cells were assessed by IFN-gamma ELISpot in vitro. See also Methods section under the heading High-Throughput Protocol.
Figure 19:
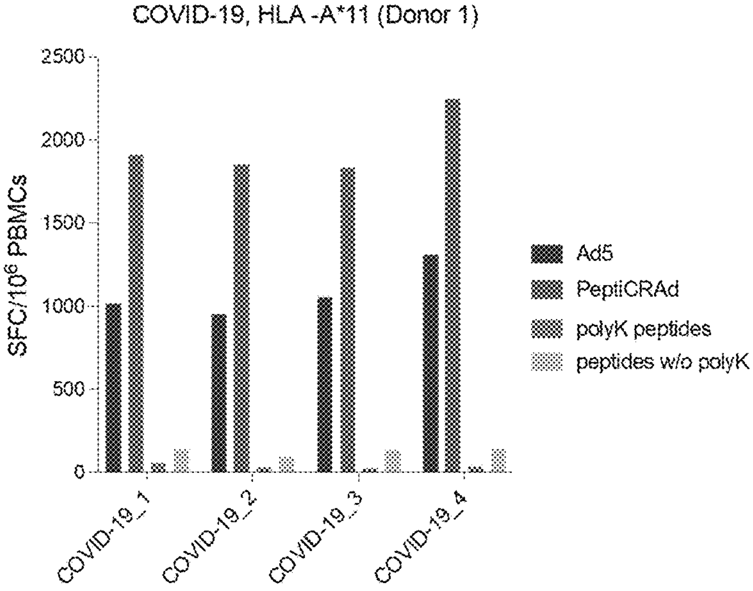
FIG. 19 shows the evaluation of SARS-CoV-2-specific T cell responses following their expansion from human PBMCs, Donor 1. PBMCs collected from a healthy donor (HLA-A*11) were stimulated with four SARS-Cov-2 (COVID-19) specific peptides, Table 1. The presence and frequency of antigen-specific T cells were assessed by IFN-gamma ELISpot in vitro based on the protocol described earlier.
Figure 20:
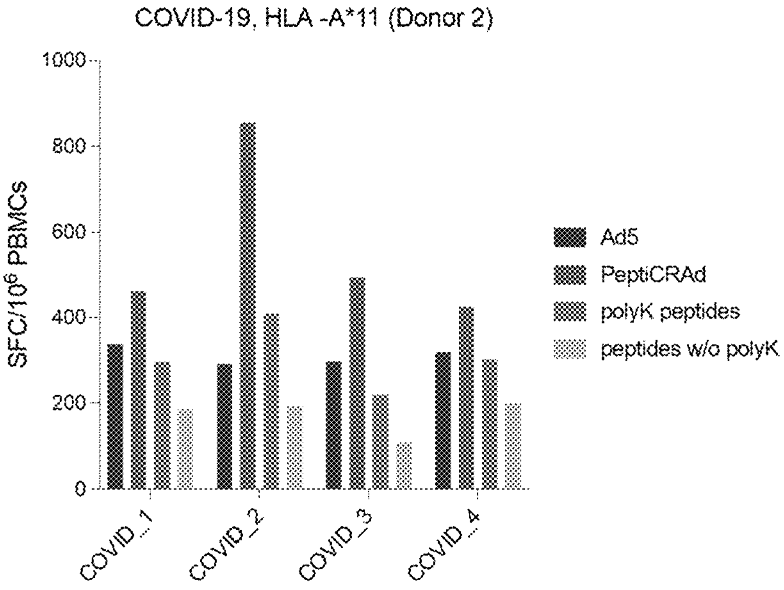
FIG. 20 shows the evaluation of SARS-CoV-2-specific T cell responses following their expansion from human PBMCs, Donor 2. PBMCs collected from a healthy donor (HLA-A*11) were stimulated with four SARS-CoV-2 (COVID-19) specific peptides, Table 1. The presence and frequency of antigen-specific T cells were assessed by IFN-gamma ELISpot in vitro based on the protocol described earlier.
Figure 21:
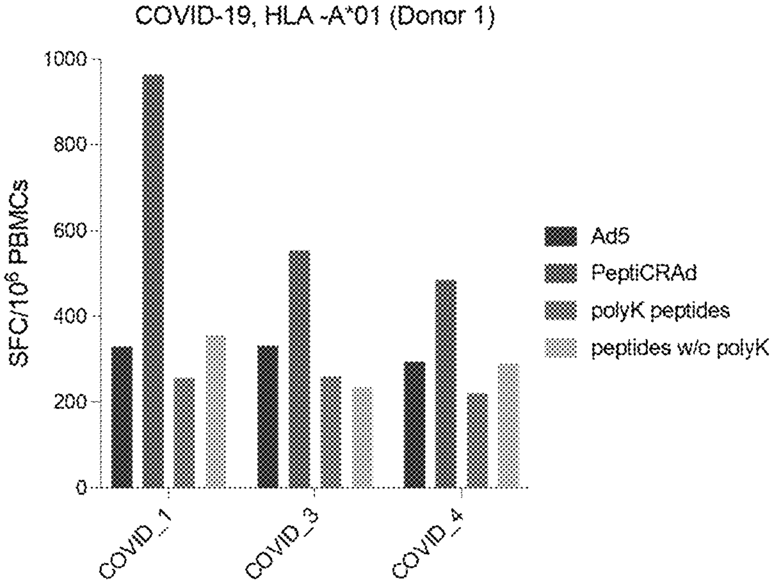
FIG. 21 shows the evaluation of SARS-CoV-2-specific T cell responses following their expansion from human PBMCs, Donor 1. PBMCs collected from a healthy donor (HLA-A*01) were stimulated with three SARS-CoV-2 (COVID-19) specific peptides. The presence and frequency of antigen-specific T cells were assessed by IFN-gamma ELISpot in vitro based on the protocol described earlier.
Figure 22:
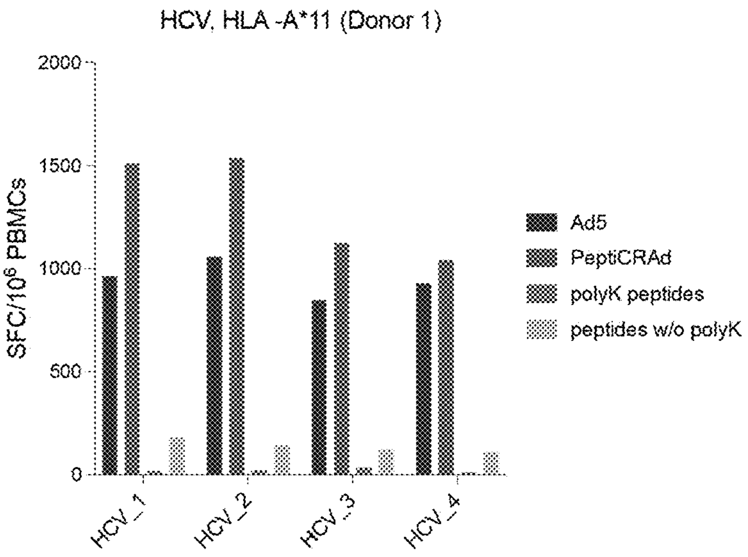
FIG. 22 shows the evaluation of HCV-specific T cell responses following their expansion from human PBMCs, Donor 1. PBMCs collected from a healthy donor (HLA-A*11) were stimulated with four HCV-specific peptides, Table 1. The presence and frequency of antigen-specific T cells were assessed by IFN-gamma ELISpot in vitro based on the protocol described earlier.
Figure 23:
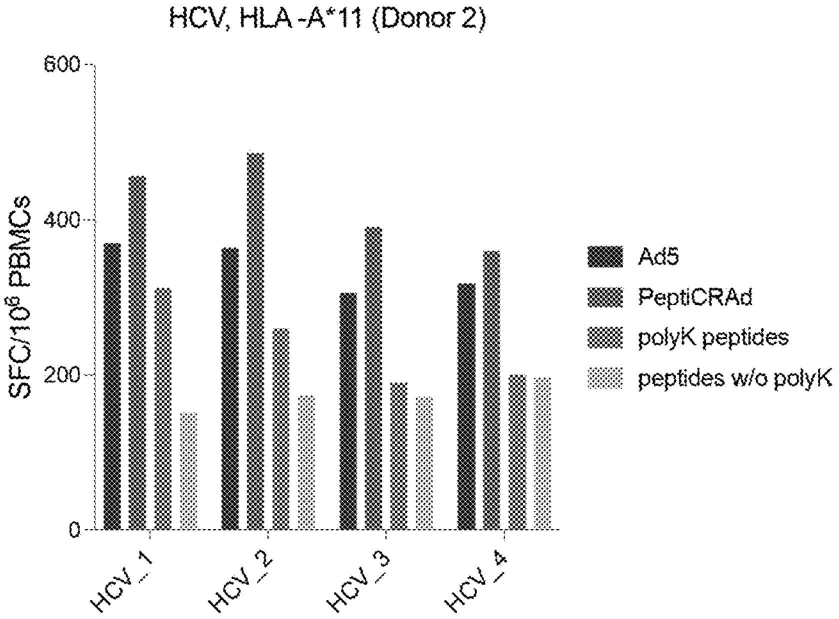
FIG. 23 shows the evaluation of HCV-specific T cell responses following their expansion from human PBMCs, Donor 2. PBMCs collected from a healthy donor (HLA-A*11) were stimulated with four HCV-specific peptides, Table 1. The presence and frequency of antigen-specific T cells were assessed by IFN-gamma ELISpot in vitro based on the protocol described earlier.
Figure 24:
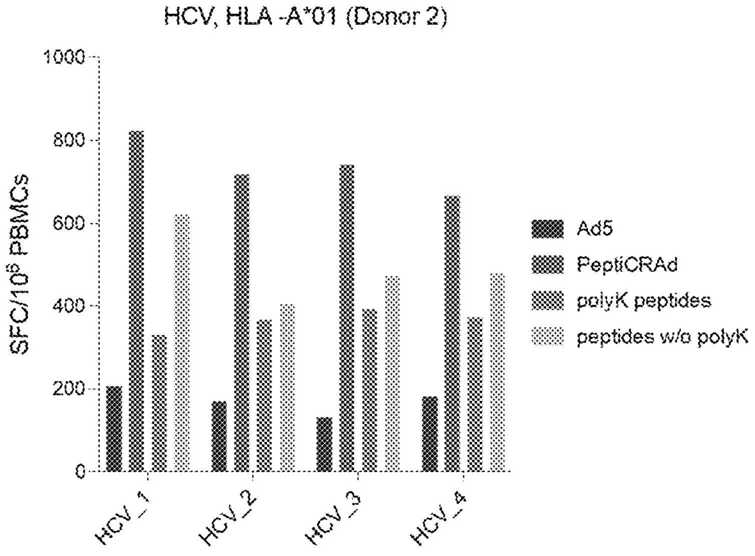
FIG. 24 shows the evaluation of HCV antigen-specific T cell responses following their expansion from human PBMCs, Donor 2. PBMCs collected from healthy donor (HLA-A*01) were stimulated with four HCV specific peptides, Table 1. Presence and frequency of infectious-disease specific T cells were assessed by IFN-gamma ELISpot in vitro based on the protocol described earlier.
Figure 25:
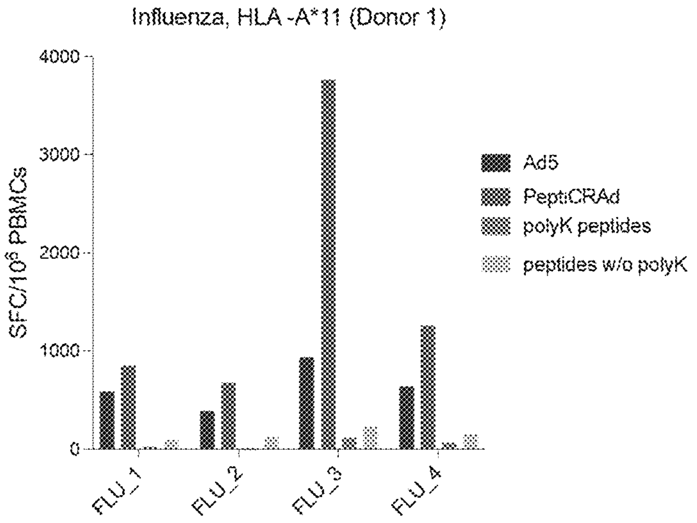
FIG. 25 shows the evaluation of Influenza A-specific T cell responses following their expansion from human PBMCs, Donor 1. PBMCs collected from a healthy donor (HLA-A*11) were stimulated with four Influenza specific peptides, Table 1. The presence and frequency of infectious-disease specific T cells were assessed by IFN-gamma ELISpot in vitro based on the protocol described earlier.
Figure 26:
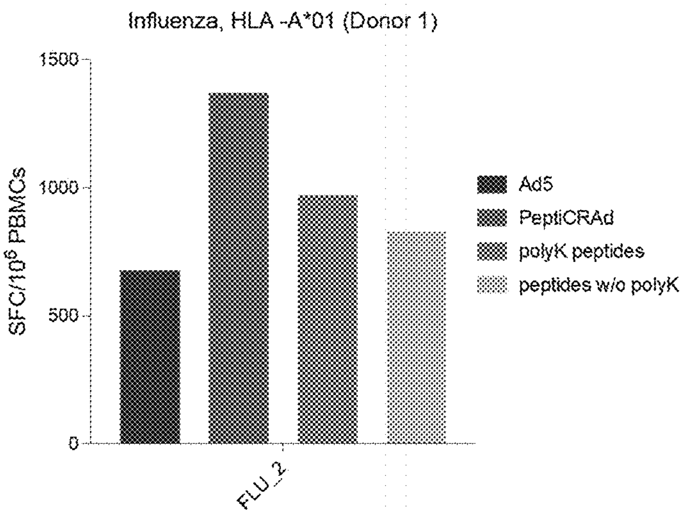
FIG. 26 shows the evaluation of Influenza A-specific T cell responses following their expansion from human PBMCs, Donor 1. PBMCs collected from healthy donor (HLA-A*01) were stimulated with Influenza specific peptides, Table 1. Presence and frequency of infectious-disease specific T cells were assessed by IFN-gamma ELISpot in vitro based on the protocol described earlier.
Figure 27:
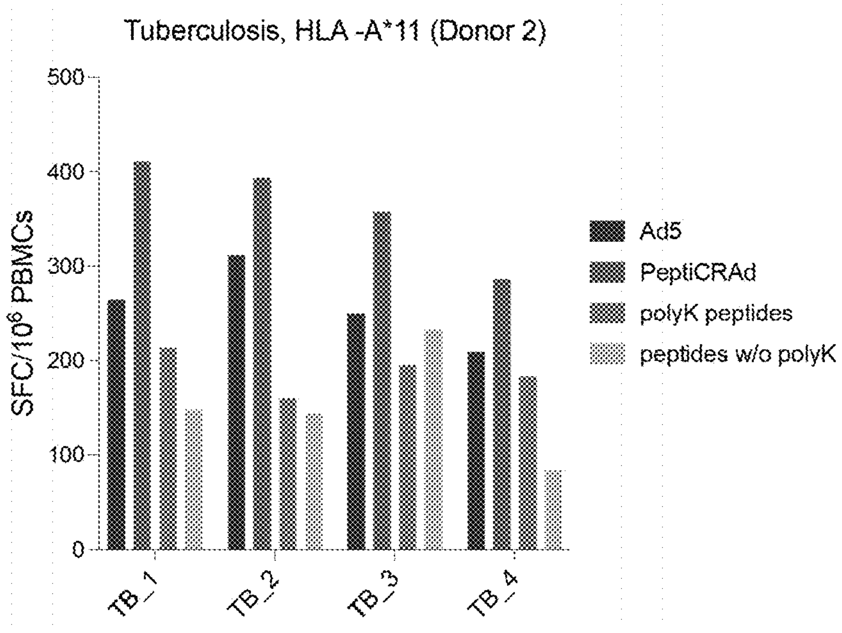
FIG. 27 shows the evaluation of *Mycobacterium Tuberculosis*-specific T cell responses following their expansion from human PBMCs, Donor 2. PBMCs collected from a healthy donor (HLA-A*11) were stimulated with four Tuberculosis specific peptides, Table 1. The presence and frequency of infectious-disease specific T cells were assessed by IFN-gamma ELISpot in vitro based on the protocol described earlier.
Figure 28:
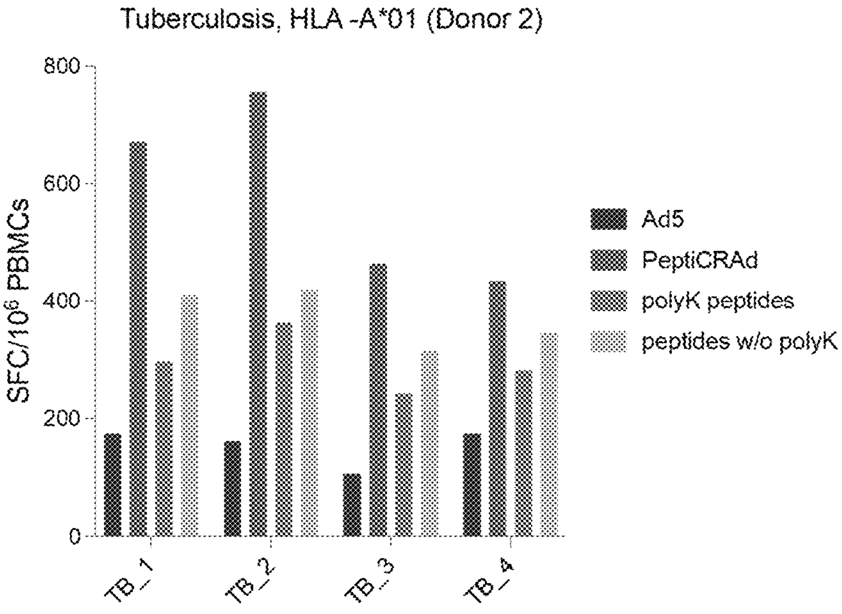
FIG. 28 shows the evaluation of Tuberculosis antigen-specific T cell responses following their expansion from human PBMCs, Donor 2. PBMCs collected from healthy donor (HLA-A*11) were stimulated with four Tuberculosis specific peptides, Table 1. Presence and frequency of infectious-disease specific T cells were assessed by IFN-gamma ELISpot in vitro based on the protocol described earlier.

PBMCs collected from healthy donors (HLA specific) were stimulated with:

i) PeptiCRAd technology (non-replicating adenovirus, serotype 5, Ad5 complexed with polyK peptides),
ii) virus alone (Ad5),
iii) polyK peptides, and
iv) peptides w/o polyK, to trigger the in vitro development of T cells that can recognize several infectious disease antigens. Four different infectious diseases representing a broad range of infectious diseases (both viral and bacterial infections) were selected: COVID-19 (SARS-CoV-2, Coronaviridae), Hepatitis C (Hepatitis C virus (HCV), Flaviviridae), Tuberculosis (*Mycobacterium tuberculosis*, Mycobacteriaceae), Influenza (Influenza A, Orthomyxoviridae) (Table 1). The presence and frequency of infectious disease antigen-specific T cells were assessed by IFN-gamma ELISpot in vitro based on the protocol described earlier (Cimen Bozkus et al. 2021, 42) (FIG. 18).

Methodology

HLA specific PBMCs were thawed in a water bath at 37 °C as described earlier (Cimen Bozkus et al. 2021, 42). Briefly, cells were seeded at a concentration of 5×106 cells/2 mL in 6-well plates in CTL-test medium. Cells were incubated at 37 °C, 5% CO2. After resting of the cells for 24 hours, the different compounds (PeptiCRAd; virus alone (Ad5); polyK peptides, and peptides w/o polyK specific for i) Influenza A, ii) Hepatitis C virus, iii) *Mycobacterium tuberculosis*, iv) SARS-CoV-2 peptide pool (each at concentration of 5.3 μg/well; 14VP/cell) were added and remained with the cells for the rest of the culture period. On day 3, 6, 8 approx. 50% of the medium was replaced with fresh medium containing cytokines, and the cells were cultured for an additional 2 days according to the protocol described earlier (Cimen Bozkus et al. 2021) (FIG. 18). Pre-sensitized T cells were tested on day 10 by IFN-γ ELISpot assay for recognition of specific antigens. Briefly, 3E+5 cells were plated per well and stimulated with the peptides or adenovirus for 24 hours on ELISPOT plate and incubated at 37 °C, 5% CO2. Plates were stained according to the protocol provided with ELISPOT plates (CTL Immunospot). The number of cytokine-producing, antigen-specific T cells was evaluated using ELISpot Reader.

Results

The Negative Charge of the Adenovirus Capsid can be Used to Complex Positively Charged Immunogenic Peptides, Forming PeptiCRfAd.

Adenovirus capsids bear a highly negative net charge (36); hence, we hypothesized that a positively charged MHC-I-restricted peptide would bind to the capsid by electrostatic interaction, covering the virus with immunologically relevant peptides (i.e., tumor-specific MHC-I-restricted peptides). To test our hypothesis, we used the B16-OVA tumor model (37). This cell line expresses chicken ovalbumin (OVA) and presents the OVA-derived peptide SIINFEKL (SEQ ID NO: 1), which we used as a model epitope, on MHC-I.

Figure 8B:
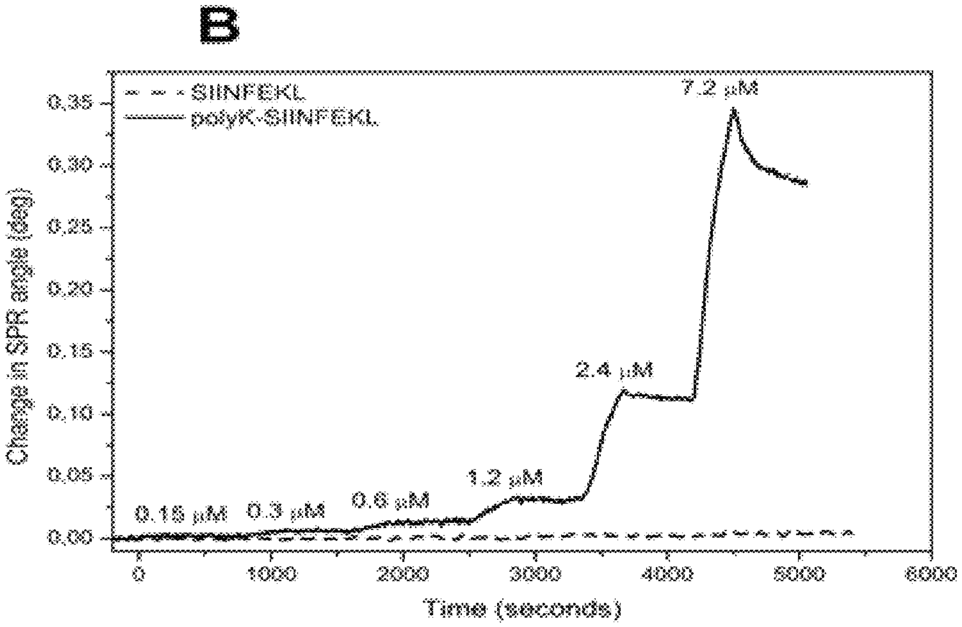
FIG. 8B reveals the interaction between the modified MHC-I epitope SIINFEKL (SEQ ID NO: 1) and oncolytic adenoviruses. The virus/peptide interaction was measured by SPR. An APTES silica $SiO_2$ sensor was coated with Ad5D24, and increasing concentrations (0.15, 0.3, 0.6, 1.2, 2.4 and 7.2 μM) of either SIINFEKL (SEQ ID NO: 1) (dashed line) or polyK-SIINFEKL (SEQ ID NO: 1; solid line) were injected into the flowing system. The SPR signal response is shown in relation to the duration of the experiment.

To allow for electrostatic interaction between the neutral, hydrophobic SIINFEKL peptide and the negative viral surface, we added a poly-lysine (polyK) chain to the peptide sequence. This chemical modification increased the net charge of the peptide from 0 to +6 mV under physiological conditions. Next, we investigated the interaction between the viral capsid and modified peptides by surface plasmon resonance (SPR). In particular, we coated an APTES silica $SiO_2$ sensor with OAds and injected increasing concentrations of SIINFEKL or polyK-SIIN into the flowing system (FIG. 8B). No increase in the signal was observed with the unmodified peptide (FIG. 8B, dashed line), whereas a concentration-dependent increase in the signal was observed with the modified peptide (FIG. 8B, solid line), demonstrating that the modification of the peptide significantly increased the interaction with the adenovirus capsid.

Next, we investigated the optimal concentration of peptide required to efficiently cover the viral surface. To this end, we evaluated the net charge and hydrodynamic diameter of the virus-peptide complexes resulting from different OAd:peptide ratios (1:5, 1:50, 1:100 and 1:500). We observed a clear relationship between the amount of positive peptide in the reaction and the net charge of the complexes (FIG. 8A). The lowest ratio (1:5) was able to increase the charge of the viral particles from −29.7±0.5 to +6.3±0.06 mV, although under these conditions, heavy aggregation was observed, as indicated by an increase in the size of the complexes (800±13.5 nm). Above 1:5, the net charge increased, reaching plateau-like kinetics; in fact, we measured zeta potentials of +17.5±0.2, +18.4±0.1 and +18±0.8 mV for the 1:50, 1:100 and 1:500 ratios, respectively. However, only at a ratio of 1:500 did the diameter of the complex decrease below 120 nm, which represents the normal diameter of adenoviral particles. (FIG. 8A) The same experiment has also been repeated with concentration of the peptides and not ratio to facilitate repeatability (FIG. 12).

Modified MHC-I Epitopes Adsorbed onto PeptiCRAd are Efficiently Cross-Presented.

To induce an effective cytotoxic T-lymphocyte-mediated immune response, peptides must be cross-presented to naïve $CD8^+$ T lymphocytes via MHC-I on APCs. Therefore, we investigated whether the presence and the position of the polyK chain could affect the efficiency of cross-presentation. For this purpose, we pulsed ex vivo-cultured splenocytes (from C57BL/6 mice) with either natural SIINFEKL or two different lysine-extended versions: polyK-SIINFEKL (N-terminus extended) and SIINFEKL-polyK (C-terminus extended). As a negative control, we included extended SIINFEKL containing an amino caproic (AHX) residue, which is a well-known analog of lysine that can inhibit the proteolytic activity of the proteasome. We then assessed the cross-presentation of SIINFEKL with the use of an antibody that specifically recognizes MHC-I loaded with SIINFEKL (38).

Figure 13A:
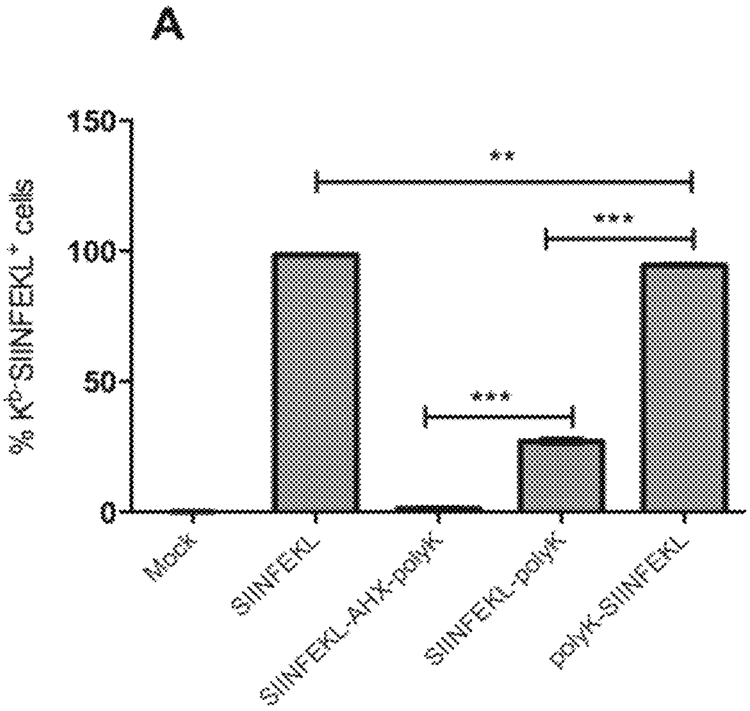
FIG. 13A shows cross-presentation of modified SIINFEKL (SEQ ID NO: 1) analogs on MHC-I adsorbed or not adsorbed onto the viral capsid. Spleens were collected from C57BL/6 mice (H-2$K^b$), and a single-cell suspension was prepared in RPMI-1640 growth media with 10% FBS. A total of $2\times10^6$ splenocytes were incubated with 200 μl of media containing unmodified SIINFEKL (SEQ ID NO:1; positive control), the amino caproic acid-containing SIINFEKL-AHX-polyK (negative control), the C-terminus-extended SIINFEKL-polyK or the N-terminus-extended polyK-SIINFEKL (0.19 μg/μl). After 2 h of incubation at 37 °C, the cells were washed and stained with APC anti-H-2$K^b$ bound to SIINFEKL (SEQ ID NO: 1) or isotype control.

As expected, 98.5% of the SIINFEKL-pulsed splenocytes were positive for the presence of SIINFEKL on the MHC-I molecule on splenocyte membranes (FIG. 13A). Interestingly, the position of the polyK chain in the sequence of the peptide significantly changed the proportion of cells stained. In fact, 94.5% of the splenocytes pulsed with the N-terminus-extended peptide cross-presented SIINFEKL. In contrast, when the splenocytes were pulsed with the C-terminus-extended SIINFEKL-polyK, the stained population decreased to 27.1%. When pulsed with the negative control SIINFEKL-AHX-polyK, only 1.36% of the splenocytes cross-presented the SIINFEKL peptide. Based on these findings, we chose the N-terminus-extended version (polyK-SIINFEKL) for further studies.

Figure 13B:
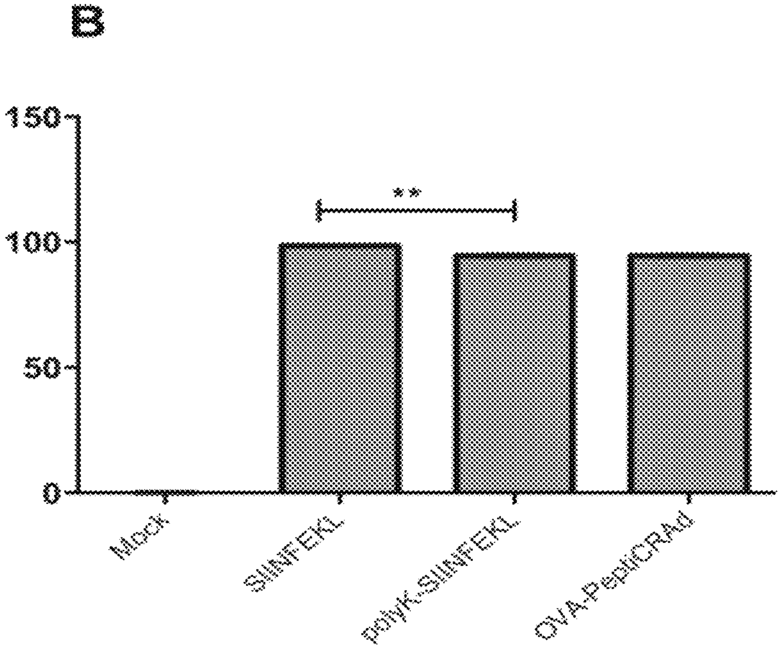
FIG. 13B illustrates that, similar to FIG. 13A, fresh murine splenocytes were infected with of OVA-PeptiCRAd (100 vp/cell+37.5 μg of peptide) and 37.5 μg of SIINFEKL (SEQ ID NO: 1; positive control) or polyK-SIINFEKL. After 2 h of incubation, the samples were washed and analyzed by flow cytometry. The data are shown as the mean±SEM (n=2). Significance was assessed using one-way ANOVA with Bonferroni's multiple comparison test; * P<0.05,  P<0.01, * P<0.001.

Next, we investigated whether the adsorption of the modified SIINFEKL onto the viral capsid could affect its cross-presentation. As in the previous experiment, we incubated mouse splenocytes with the peptide SIINFEKL or polyK-SIINFEKL or with OVA-PeptiCRAd. We found that the N-terminus-extended polyK-SIINFEKL complexed with an OAd, forming PeptiCRAd, allowed for efficient MHC-I-restricted presentation of the SIINFEKL peptide (FIG. 13B).

PeptiCRAd Shows Unaltered Infectivity and Intact Oncolytic Activity Compared with Unmodified Viruses.

Figure 14A:
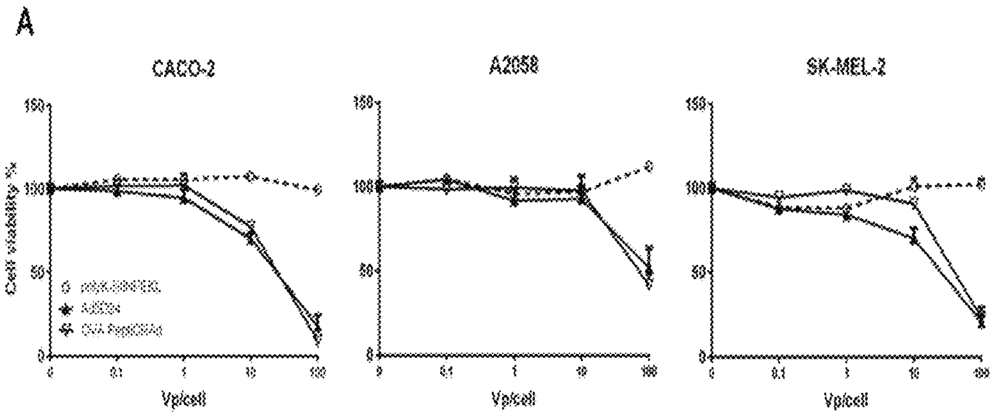
FIG. 14A shows that PeptiCRAd retains intact oncolytic activity and displays increased infectivity in cell lines with low CAR expression. Cells were seeded at a density of $1\times10^4$ cells per well and infected with OVA-PeptiCRAd or naked Ad5D24 using different vp/cell ratios (0.1, 1, 10 and 100). The peptide polyK-SIINFEKL (dashed line, circles) was included as a control. The cell viability was then determined by MTS assay. The data are shown as the mean±SEM (n=3).

OAds can selectively infect tumor cells and lyse them via the OAd replication cycle. Thus, we investigated whether coating the viruses with modified peptides would affect their biological properties. We chose to study a human colorectal adenocarcinoma cell line (CACO-2) expressing low levels of coxsackie and adenovirus receptor (CAR) and two human melanoma cell lines (SK-MEL-2 and A2058) expressing higher levels of CAR. An in vitro viability assay comparing OVA-PeptiCRAd with the unmodified virus Ad5D24 was first performed (FIG. 14A), and the results showed no significant differences with regard to oncolytic activity. As expected, the most infectious condition (100 vp/cell) correlated with the lowest viability in all cell lines. In addition, we showed that the peptide polyK-SIINFEKL had no toxic effect on cells.

Figure 14B:
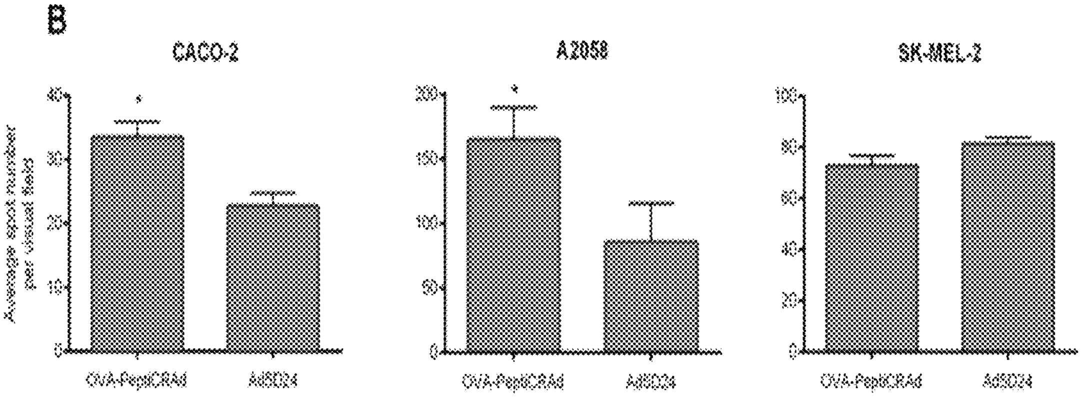
FIG. 14B shows a study of viral infectivity by ICC. A total of $2\times10^5$ cells per well were seeded in a 24-well plate and infected with 100 μl of viral dilution (10 vp/cell) containing either OVA-PeptiCRAd or Ad5D24 (control) on the following day. After two days of incubation, anti-hexon ICC was performed, and five non-overlapping images were acquired using a digital microscope. The average number of spots per visual field is presented. The data from a representative experiment are shown as the mean f SEM (n=2-3). Significance was assessed using the unpaired t-test with Welch's correction; * P<0.05,  P<0.01, * P<0.001.

Next, we evaluated the infectivity of PeptiCRAd by immunocytochemistry (ICC) assays using the same cell lines in vitro (FIG. 14B). Whereas we did not observe any difference in the SK-MEL-2 cell line, in the CACO-2 and A2058 cell lines, PeptiCRAd showed a significant increase (P<0.01) in infectivity compared with the naked adenovirus. This increase was likely due to the different charges of PeptiCRAd and the naked adenovirus (36).

Studies of the Anti-Tumor Efficacy and Immunology of a PeptiCRAd Cancer Vaccine in a Murine Model of Melanoma.

To thoroughly study the anti-tumor efficacy of PeptiCRAd and the anti-tumor immunity that it promotes, we first used a murine model of melanoma over-expressing chicken OVA (B16-OVA) (35). Specifically, B16-OVA was implanted in the flanks of mice, after which the established tumors were treated. The experiment was performed using an OAd bearing the D24 deletion in E1A (Ad5D24) (37) and then repeated with a CpG-rich adenovirus (Ad5D24-CpG) (39) to further boost immunity (FIG. 15). The study groups included mice treated with OVA-PeptiCRAd, with non-complexed Ad5D24-CpG and SIINFEKL (Ad5D24-CpG+

SIINFEKL), with OAd (Ad5D24-CpG) or peptide (SIINFEKL) alone or with saline solution (mock).

Figure 15A:
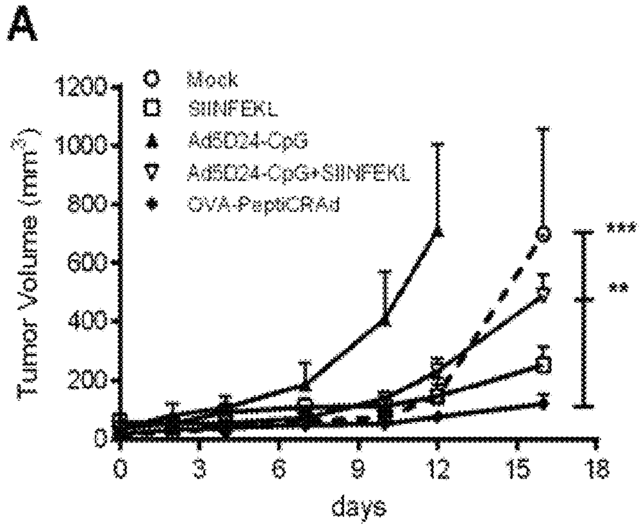
FIG. 15A shows anti-tumor efficacy of PeptiCRAd and immunological analysis of antigen-specific $CD8^+$ T cells and DCs. C57BL/6 mice (n=6) received $3\times10^5$ B16-OVA cells in both flanks. Treatment was initiated 9 days later and included saline solution (mock), peptide alone (SIINFEKL; SEQ ID NO: 1), virus alone (Ad5D24-CpG), a mixture of virus and peptide (Ad5D24-CpG+SIINFEKL) and virus-peptide complex (OVA-PeptiCRAd). The mice were treated three times (on days 0, 2 and 7). Tumor size was then measured and is presented as the mean±SEM as a function of time. Statistical analysis was performed using two-way ANOVA with Bonferroni's multiple comparison test. * P<0.05,  P<0.01, * P<0.001. Tumors, spleens and inguinal lymph nodes were collected from mice (n=3-4) at two time points: the $7^{th}$ day (early) and the $16^{th}$ day (late). The proportion of SIINFEKL-specific $CD8^+$ T cells was then determined by gating out $CD19^+$ cells. The percentage of $CD8^+OVA^+$ T cells is presented as the mean±SEM.

PeptiCRAd treatment significantly reduced tumor growth compared with mock treatment or the mixture of OAd and SIINFEKL ($P<0.01$). At the end of the experiment, the average volume of the tumors in the OVA-PeptiCRAd-treated mice was lower than in all other groups (120.4±31.6 $mm^3$ vs. 697.7±350 $mm^3$ in mock, 255±61.5 $mm^3$ in SIINFEKL, and 713.7±292.6 $mm^3$ in Ad5D24-CpG, 489.7±73.2 $mm^3$ in Ad5D24-CpG+SIINFEKL; FIG. 15A).

Figure 15B:
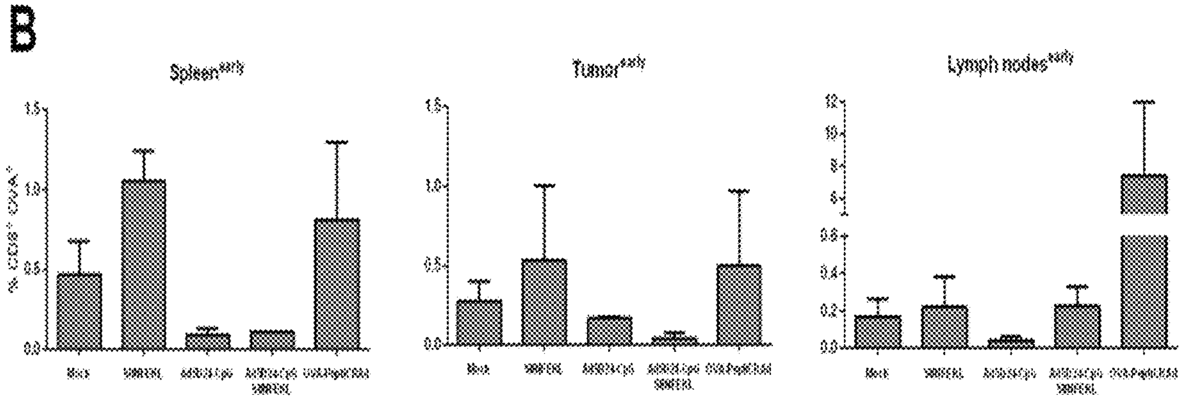
FIG. 15B shows average percentage of double-positive $CD8^+OVA^+$ T cells from the $7^{th}$ day (early) collection.
Figure 15C:
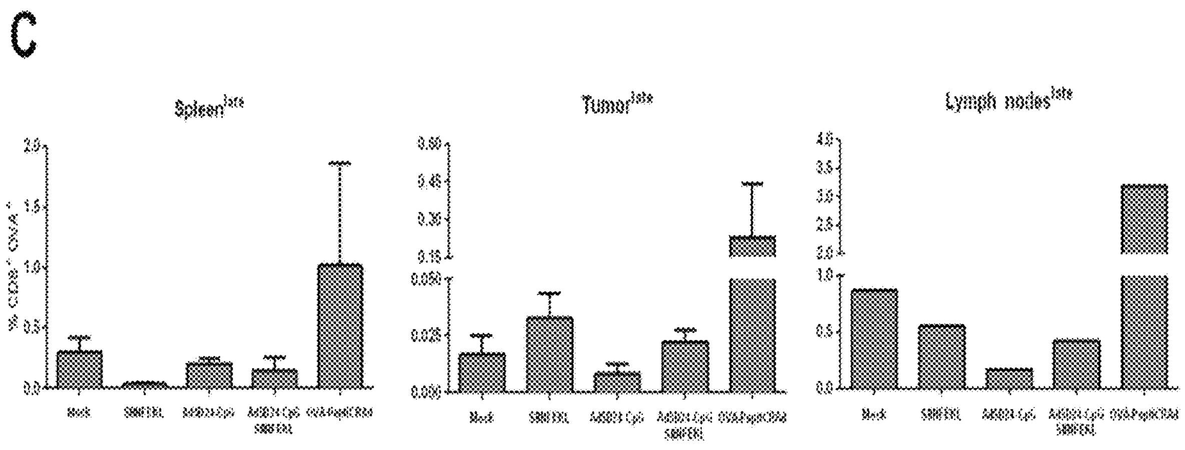
FIG. 15C shows average percentage of double-positive $CD8^+OVA^+$ T cells from the $16^{th}$ day (late) collection.
Figure 15D:
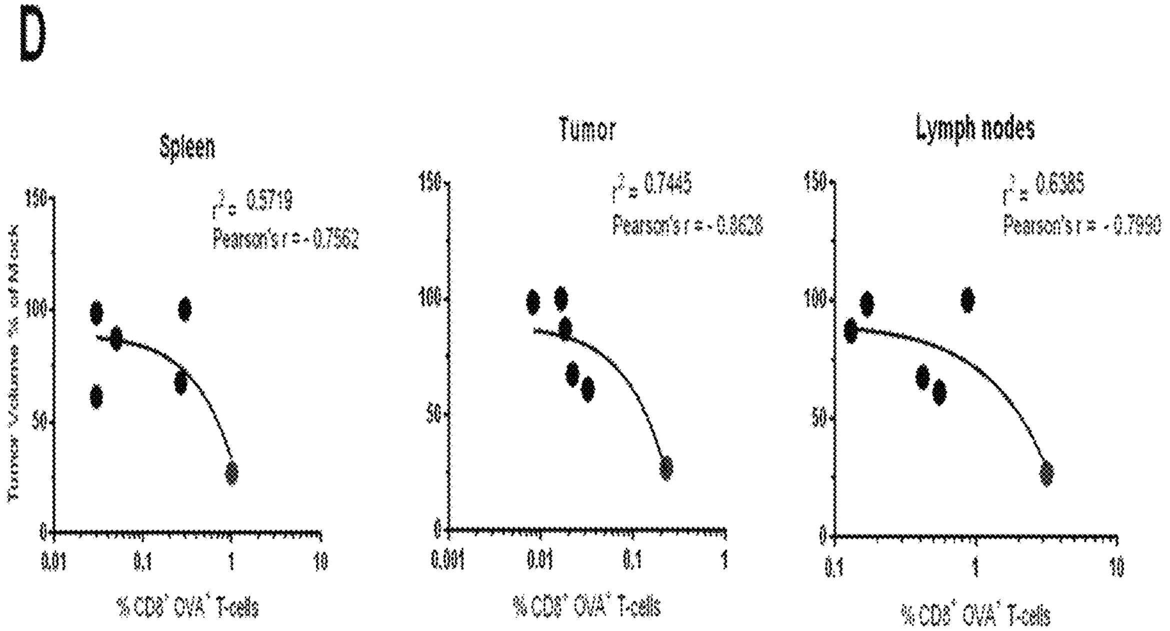
FIG. 15D shows average tumor size at the end of the experiment (linear y axis) plotted against the average percentage of double-positive $CD8^+OVA^+$ T cells ($\log_{10}$ x axis). The Pearson's r and $r^2$ values were also calculated and graphed for each set of samples.

At two different time points (days 7 and 16 for the early and late time points, respectively), the mice were sacrificed, and spleens, tumors and draining lymph nodes were collected for immunological analysis. This analysis revealed the presence of a large population of SIINFEKL-specific $CD8^+$ T cells ($CD8^+OVA^+$ T cells) in the inguinal draining lymph nodes in the group of mice treated with PeptiCRAd (7.4% at day 7 and 3.2% at day 16). The same analysis showed no drastic difference in tumors at the early time point, whereas a substantial increase was observed at the late time point (0.23% in OVA-PeptiCRAd vs. 0.02% in mock, 0.03% in SIINFEKL, 0.01% in Ad5D24-CpG and 0.02% in Ad5D24-CpG+SIINFEKL at day 16; FIGS. 15B and C).

We then studied the correlation between the sizes of the tumors and the population of OVA-specific T cells ($CD8^+$ $OVA^+$ T cells) in the spleen, lymph nodes and tumors. We calculated the Pearson's r value to estimate the nature of the correlation (negative value, negative correlation; positive value, positive correlation) and observed a negative correlation between the tumor volume and the extent of the anti-OVA response (FIG. 15D), indicating that the groups of animals with smaller tumors corresponded to the groups of animals with a more robust population of $CD8^+OVA^+$ T cells. Afterwards, the $r^2$ value was calculated for each set of samples to evaluate the strength of this correlation (spleen, $r^2=0.5719$; lymph nodes, $r^2=0.6385$; tumors, $r^2=0.7445$). Interestingly, in the correlation analyses, the PeptiCRAd group (red dots in FIG. 15D) consistently showed the smallest tumor volume and the greatest immunological response.

Figure 15E:
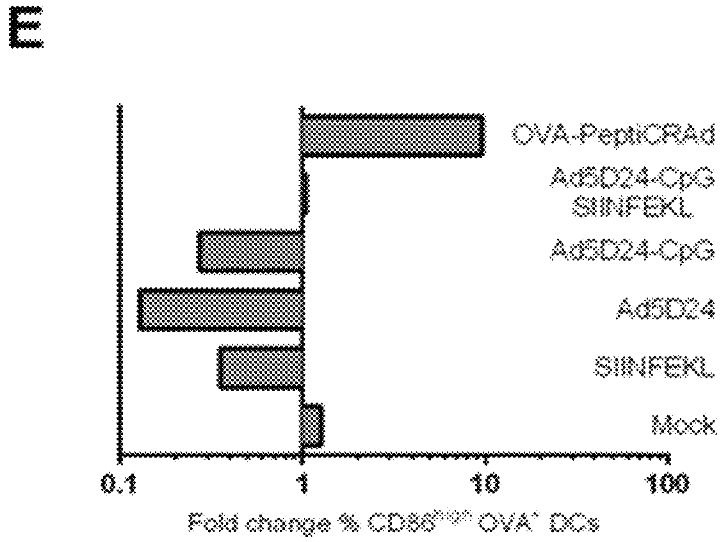
FIG. 15E shows the determined fold change in DCs showing a mature profile and cross-presenting SIINFEKL on their MHC-I molecules. Mature DCs were defined as $CD19^-CD3^-CD11c^+CD86^{high}$ cells. APC anti-mouse H-2$K^b$ bound to SIINFEKL was used to track the cross-presentation of SIINFEKL on MHC-I in the selected pool of DCs.

Finally, to deepen our understanding of the mechanisms of PeptiCRAd, we evaluated the proportion of mature DCs ($CD19{:}CD3^-CD11c^+CD86^{high}$ cells) presenting the SIINFEKL peptide on MHC-I in the spleens of the mice. At the late time point, the proportion of mature SIINFEKL-presenting DCs was significantly higher ($P<0.05$) in the mice treated with OVA-PeptiCRAd than in the mice treated with the non-complexed Ad5D24-CpG+SIINFEKL. When both time points are considered, PeptiCRAd was the only treatment that induced an increase in mature SIINFEKL-presenting DCs, as shown by the 9.67-fold increase in the $CD86^{high}OVA^+$ DC population (FIG. 15E).

These results suggest that expansion of the mature and epitope-specific DC pool could be the basis for the higher anti-tumor efficacy of PeptiCRAd.

Multivalent PeptiCRAd Shows Enhanced Anti-Tumor Activity Toward Distant, Untreated Melanomas.

One of the main advantages of using oncolytic vaccines is that the immune response elicited facilitates targeting not only the primary tumors but also disseminated metastasis. For this reason, we investigated the anti-tumor efficacy of PeptiCRAd toward untreated contralateral tumors in a murine model of melanoma. In the same set of experiments, we also studied whether targeting two tumor antigens (via multivalent PeptiCRAds), rather than a single one, would increase the overall efficacy. Therefore, we chose two tumor-specific MHC-I-restricted epitopes to coat the oncolytic virus Ad5D24-CpG: SVYDFFVWL (SEQ ID NO: 5) (TRP-$2_{180-188}$; restricted to the murine MHC-I molecule H-$2K^b$) and KVPRNQDWL (SEQ ID NO: 6) (human $gp100_{25-33}$, or hgp100; restricted to the murine MHC-I molecule H-$2D^b$ (40)). For these experiments, we employed the highly aggressive melanoma B16-F10, which expresses both tumor antigens (41). The peptides were modified with a polyK chain at their N-terminus to favor their adsorption onto the viral capsid, as before for SIINFEKL (SEQ ID NO: 1).

Figure 16A:
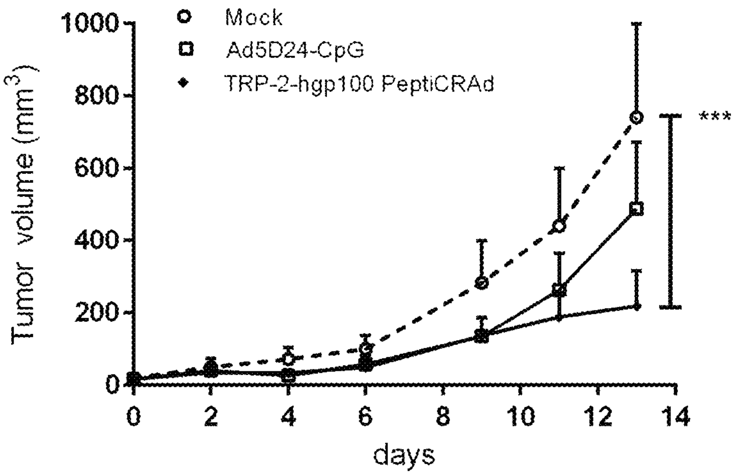
FIG. 16A shows that targeting two tumor antigens with PeptiCRAd reduces the growth of both treated and distant, untreated tumors. One primary tumor was engrafted in C57BL/6 mice on the right flank using $1\times10^5$ B16-F10 melanoma cells. Treatment started at day 10. At day 16, the mice received $3\times10^5$ B16-F10 cells on their left flank. The Figure reports the growth of the primary (right) tumor, and the data are presented as the mean±SEM (n=5). Significance was determined using two-way ANOVA with Bonferroni's multiple comparison test; * P<0.05,  P<0.01, * P<0.001.
Figure 16B:
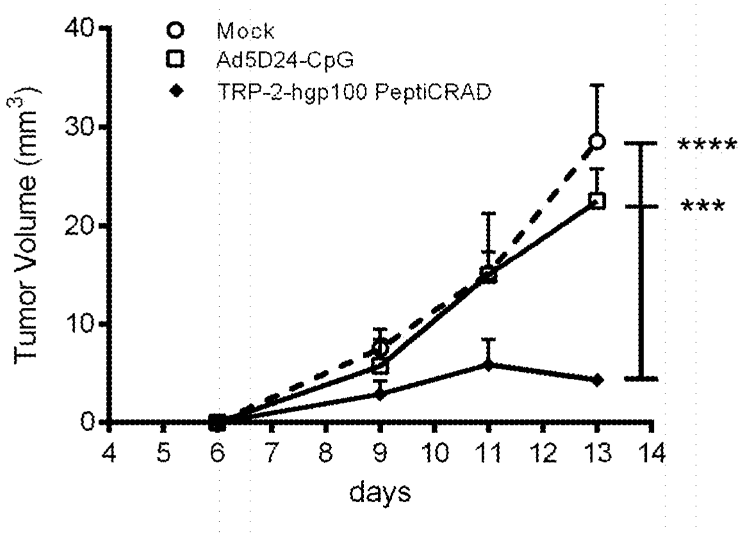
FIG. 16B reports the size of the secondary (left) tumors at the end of the experiment on a $\log_2$ scale. Significance was assessed using the Mann-Whitney U-test; * P<0.05,  P<0.01, * P<0.001.

We first implanted $1\times10^5$ B16-F10 cells into the right flank of C57BL/6 mice. After 10 days, treatments were initiated as follows: i) saline solution (mock), ii) naked oncolytic virus (Ad5D24-CpG), and iii) double-coated TRP-2-hgp100-PeptiCRAd. The treatments were administered intratumorally every second day, as shown in the schematic in FIG. 6A. Two days after the last round of injections, $3\times10^5$ B16-F10 cells were injected into the left flank of the mice, and the growth of melanomas followed. The mice treated with the double-coated PeptiCRAd showed significantly reduced tumor growth ($P<0.001$) compared with the control (at day 11; FIG. 16A). Analysis of secondary and untreated tumors revealed an advantage of the double-coated PeptiCRAd over all other groups. In particular, at the end of the experiment, the secondary tumors in this group were significantly smaller compared with those in the controls receiving saline solution or only Ad5D24-CpG ($P<0.01$; FIG. 16B).

Figure 16C:
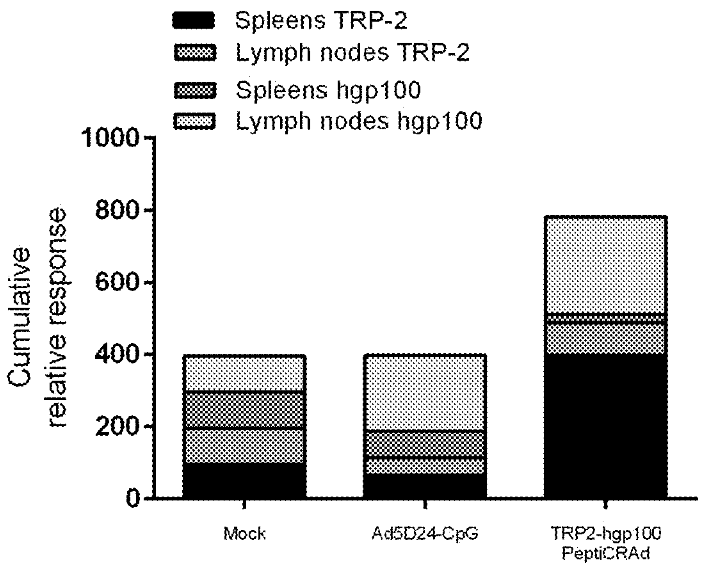
FIG. 16C illustrates the determined level of TRP-2- and hgp100-specific $CD8^+$ T cells in harvested spleens and inguinal lymph nodes by MHC-I pentamer staining. The percentage of epitope-specific $CD8^+$ T cells found in each organ was normalized against mock and is presented as the cumulative relative response for each experimental group.

To better clarify the mechanisms underpinning these results, we performed a flow cytometry analysis to study the specific T-cell responses to both epitopes. In mice treated with TRP-2-hgp100 PeptiCRAd, we observed a larger cumulative population of epitope-specific $CD8^+$ T cells (FIG. 16C) than in all other groups.

Taken together, these results demonstrate that the PeptiCRAd approach is effective against a less immunogenic and more aggressive melanoma model. In addition, targeting multiple antigens results in a strong effect on both treated and untreated tumors. Hence, it is possible to generate multivalent PeptiCRAds, and they can give us the possibility to target different tumor antigens hence overcoming the some immunological escape of the tumor.

PeptiCRAd Displays Enhanced Efficacy and Anti-Tumor Immunity in Humanized Mice Bearing Human Tumors.

Finally, we wanted to assess the efficacy of PeptiCRAd in a model that could provide information on the feasibility of its translation to the clinical setting. Therefore, we chose a more sophisticated humanized mouse model. To this end, triple-knockout mice (NOD.Cg-$Prkdc^{scid}$-$IL2rg^{tmlWjl}$/SzJ, or NSG) were first engrafted with the human melanoma cell line SK-MEL-2. When the tumor reached a palpable size, partially matched human peripheral blood mononuclear cells (PBMCs) from a healthy donor were engrafted into the same mice. One day later, the mice were treated with PeptiCRAd, uncoated virus or saline solution. For this experiment, we chose a peptide derived from melanoma-associated antigen A1 (MAGE-$A1_{96-104}$; SLFRAVITK; SEQ ID NO: 4) and modified it to allow for interaction with the viral capsid (polyK-SLFRAVITK). In this experiment, as we were studying a completely human immune system, we selected an OAd expressing human GM-CSF, which we have previously shown to have enhanced activity in an immunocompetent system, including in cancer patients (8).

Figure 17A:
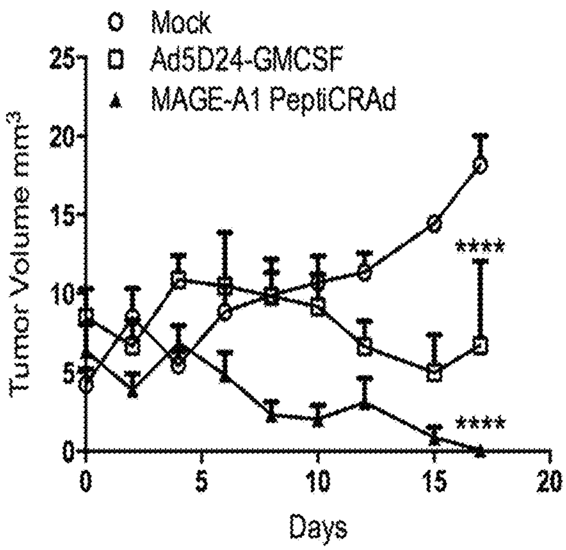
FIG. 17A shows efficacy of PeptiCRAd in humanized mice bearing human melanomas. Triple-knockout NGS mice received $2\times10^6$ human melanoma cells (SK-MEL-2) on each flank. When the tumors reached an average diameter of 4-5 mm, a group of mice (n=3) received human PBMCs from an HLA-A-matched healthy donor, whereas another group of mice (n=2) did not receive PBMCs. The mice were then treated (at days 0, 2 and 4) with one of the following: i) saline solution (mock), ii) Ad5D24-GM-CSF, and iii) MAGE-A1 PeptiCRAd. The tumor volume of the humanized mice is presented as the mean SEM. Significance was assessed using two-way ANOVA with Bonferroni's multiple comparison test; * P<0.05,  P<0.01, * P<0.001, **** P<0.0001.
Figure 17B:
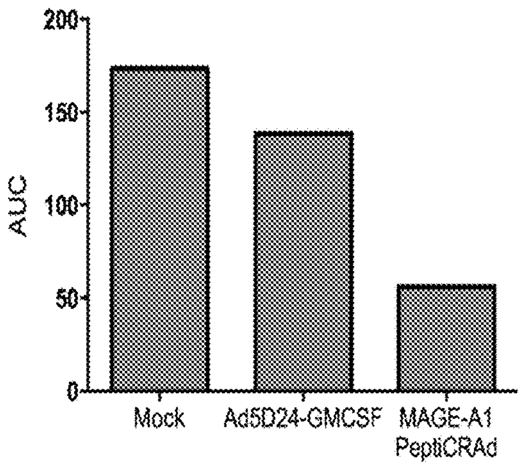
FIG. 17B presents, for each group of humanized mice, the area under the curve (AUC) relative to the size of the tumor.
Figure 17C:
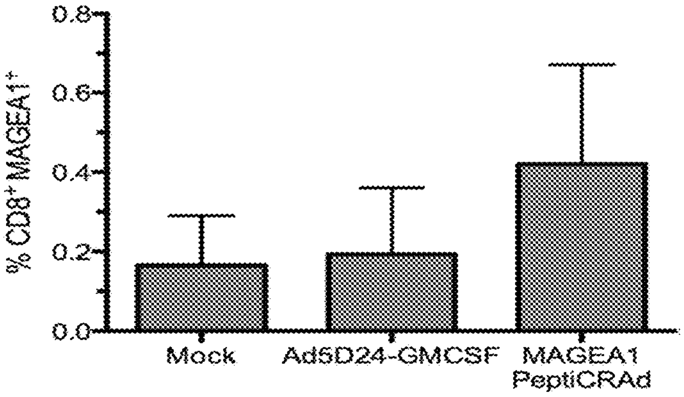
FIG. 17C reports the tumor volume of non-humanized mice, reported as the mean±SEM (**** P<0.0001).

We found that MAGE-A1 PeptiCRAd showed increased efficacy compared with the control treatments, as shown by the rapid reduction in the tumor volume (FIGS. 17A and B). Finally, we investigated whether a stronger immunological response could explain the increased anti-tumor efficacy of PeptiCRAd in this model. To this end, we studied the presence of MAGE-$A1_{96-104}$-specific $CD8^+$ T cells by pentamer staining (FIG. 17C), and we found the largest population of human MAGE-specific T cells ($CD8^+$MAGE-$A1^+$) in the spleens of mice treated with PeptiCRAd.

These data confirm our previous findings that PeptiCRAd stimulates the tumor-specific immune response by taking advantage of the natural immunogenicity of oncolytic viruses, hence improving the efficacy of cancer immunovirotherapy.

Analysis of MHC-I Specific Polypeptides on any Disease and Coating of the Adenoviral Capsid and Uses Thereof Any MHC-I specific polypeptide(s) is(are) identified by comparing MHC-I-restricted polypeptides represented by DCs and infected disease cells of a subject. One or more polypeptides presented by both cell groups are selected for coating an adenoviral vector.

Any adenoviral vector is selected and coated according to any method described in Method 2.

The coated vectors are used for treating the disease of a patient.

High-Throughput Protocol to Expand Antigen-Specific T Cells from Human Peripheral Blood Mononuclear Cells We determined the antigen specificities of a T-cell repertoire in vitro to screen for therapy-induced T-cell infection immunity. Here, we expanded antigen-specific T cells from donor human peripheral blood mononuclear cells (PBMCs) followed by peptide stimulation and detection of antigen-specific effector cytokine formation by IFN-gamma ELISpot.

We stimulated PBMCs with:

i) PeptiCRAd technology (non-replicating adenovirus, serotype 5, Ad5 complexed with polyK peptides),
ii) virus alone (Ad5),
iii) polyK peptides alone, and
iv) peptides without polyK tails.

This triggered the in vitro development of T cells that can recognize several infectious disease antigens. Four different infectious diseases representing a broad range of infectious diseases (both viral and bacterial infections) were investigated: COVID-19 (SARS-CoV-2, Coronaviridae), Hepatitis C (Hepatitis C virus (HCV), Flaviviridae), Tuberculosis (*Mycobacterium tuberculosis*, Mycobacteriaceae), Influenza (Influenza A, Orthomyxoviridae) (The exemplary peptides used are shown in Table 1). The presence and frequency of infectious disease antigen-specific T cells were assessed by IFN-gamma ELISpot in vitro based on the protocol described earlier (Cimen Bozkus et al. 2021, 42) (FIG. 18).

Analysis of antigen-reactive PBMCs using ELISpot assay demonstrated a profound increase in numbers of SARS-CoV-2-specific T cells when priming with Ad5 complexed with polyK peptides, PeptiCRAd, in comparison to Ad5 alone, polyK peptides alone or peptides without polyK tails (FIG. 2-4).

Figure 11:
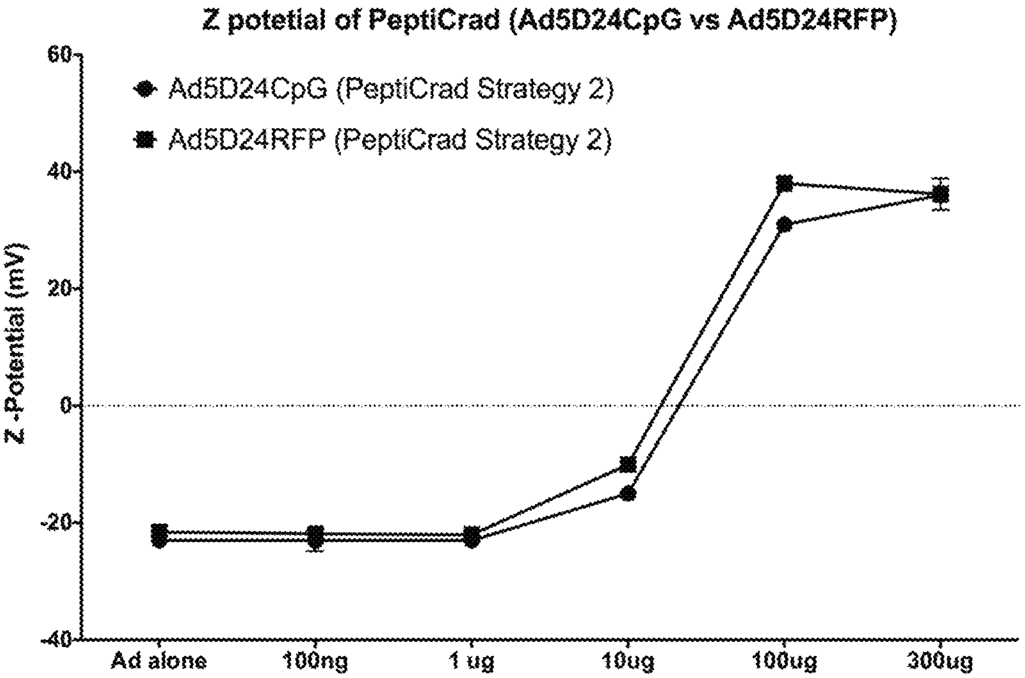
FIG. 11 shows the consistency of the peptide coating technique. The figure shows the net charge of two different oncolytic adenoviruses coated with modified peptide (6K-SIINFEKL; SEQ ID NO:1). The two viruses used in this example are Ad5D24-CpG (oncolytic adenovirus genetically modified to have its genome rich in CpG islands) and Ad5D24-RFP which is an oncolytic adenovirus encoding for the Red fluorescent protein for facilitating the imagining in vitro and in vivo; (RFP refers to Red Fluorescent Protein).

Similar observations were made for the HCV experiments (FIGS. 5-7), Influenza A experiments (FIGS. 8-9) and *Mycobacterium tuberculosis* experiments (FIGS. 10-11), indeed, specific T cell count was triggered by Ad5 complexed with polyK peptides, PeptiCRAd. PeptiCRAd priming strategy was found to be superior in the development of various infectious disease antigen-specific T cells in vitro over Ad5 alone, polyK peptides alone and peptides without polyK tails.

These findings show that PeptriCRAd can trigger the development of adaptive immune responses against various antigens representing a broad range of infectious diseases caused both by viruses and bacteria: COVID-19 (SARS-CoV-2), Hepatitis C (HCV), Tuberculosis (*Mycobacterium tuberculosis*), and Influenza (Influenza A virus).

TABLE 1

List of the peptides used in the T-cell-based immunogenicity protocol for evaluating human antigen-specific responses.

| Infectious disease | Pathogen | Peptide | Sequence |
|---|---|---|---|
| COVID-19 | SARS CoV-2 Virus (*Coronaviridae*) Viral infection | 6K-COVID_1 | KKKKKKLLLDRLNQL (SEQ ID NO: 8) |
| | | 6K-COVID_2 | KKKKKKFIAGLIAIV (SEQ ID NO: 9) |
| | | 9K-COVID_3 | KKKKKKKKKIAMAC LVGLMWLSYFIASFR LFAR (SEQ ID NO: 10) |
| | | 9K-COVID_4 | KKKKKKKKKQMAPIS AMVRMYIFFASFYYV WK (SEQ ID NO: 11) |
| | | COVID_1 | LLLDRLNQL (SEQ ID NO: 12) |
| | | COVID_2 | FIAGLIAIV (SEQ ID NO: 13) |
| | | COVID_3 | IAMACLVGLMWLSYF IASFRLFAR (SEQ ID NO: 14) |
| | | COVID_4 | QMAPISAMVRMYIFF ASFYYVWK (SEQ ID NO: 15) |
| Hepatitis C | HCV Virus (*Flaviviridae*) Viral infection | 6K-HCV_1 | KKKKKKATDALMTG Y (SEQ ID NO: 16) |
| | | 6K-HCV_2 | KKKKKKATDALMTG F (SEQ ID NO: 17) |
| | | 6K-HCV_3 | KKKKKKDLMGYIPAV (SEQ ID NO: 18) |
| | | 6K-HCV_4 | KKKKKKCINGVCWT V (SEQ ID NO: 19) |

TABLE 1-continued

List of the peptides used in the T-cell-based immunogenicity protocol for evaluating human antigen-specific responses.

| Infectious disease | Pathogen | Peptide | Sequence |
|---|---|---|---|
| | | HCV_1 | ATDALMTGY (SEQ ID NO: 20) |
| | | HCV_2 | ATDALMTGF (SEQ ID NO: 21) |
| | | HCV_3 | DLMGYIPAV (SEQ ID NO: 22) |
| | | HCV_4 | CINGVCWTV (SEQ ID NO: 23) |
| Influenza | InfluenzaVirus (*Orthomyxoviridae*) Viral infection | FLU_1 | CTELKLSDY (SEQ ID NO: 24) |
| | | FLU_2 | VSDGGPNLY (SEQ ID NO: 25) |
| | | FLU_3 | SIIPSGPLK (SEQ ID NO: 26) |
| | | FLU_4 | ASNENMETM (SEQ ID NO: 27) |
| | | 9K-FLU_1 | KKKKKKKKKCTELKLSDY (SEQ ID NO: 28) |
| | | 9K-FLU_2 | KKKKKKKKKVSDGGPNLY (SEQ ID NO: 29) |
| | | 6K-FLU_3 | KKKKKKSIIPSGPLK (SEQ ID NO: 30) |
| | | 6K-FLU_4 | KKKKKKASNENMETM(SEQ ID NO: 31) |
| Tuberculosis | Bacteria Mycobacterium tuberculosis (*Mycobacteriaceae*) Bacterial infection | 6K-TB_1 | KKKKKKKLIANNTRV (SEQ ID NO: 32) |
| | | 6K-TB_2 | KKKKKKGLPVEYLQV (SEQ ID NO: 33) |
| | | 6K-TB_3 | KKKKKKVLTDGNPPEV (SEQ ID NO: 34) |
| | | 6K-TB_4 | KKKKKKAMASTEGNV (SEQ ID NO: 35) |
| | | TB_1 | KLIANNTRV (SEQ ID NO: 36) |
| | | TB_2 | GLPVEYLQV (SEQ ID NO: 37) |
| | | TB_3 | VLTDGNPPEV (SEQ ID NO: 38) |
| | | TB_4 | AMASTEGNV (SEQ ID NO: 39) |

REFERENCES

1. Mocellin, S (2012). Peptides in melanoma therapy. Curr Pharm Des 18: 820-831.
2. Lipscomb, M F and Masten, B J. Dendritic Cells: Immune Regulators in Health and Disease. physrev.physiology-.org.
3. Degli-Esposti, M A and Smyth, M J (2005). Close encounters of different kinds: dendritic cells and N K cells take centre stage. Nat Rev Immunol 5: 112-124.
4. Trinchieri, G, Aden, D P and Knowles, B B (1976). Cell-mediated cytotoxicity to SV40-specific tumour-associated antigens. Nature 261: 312-314.
5. Steinman, R M, Hawiger, D and Nussenzweig, M C (2003). Tolerogenic dendritic cells. Annu. Rev. Immunol. 21: 685-711.
6. Wongthida, P, Diaz, R M, Galivo, F, Kottke, T, Thompson, J, Melcher, A, et al. (2011). VSV oncolytic virotherapy in the B16 model depends upon intact MyD88 signaling. Mol Ther 19: 150-158.
7. Prestwich, R J, Errington, F, Diaz, R M, Pandha, H S, Harrington, K J, Melcher, A A, et al. (2009). The case of oncolytic viruses versus the immune system: waiting on the judgment of Solomon. Hum Gene Ther 20: 1119-1132.
8. Cerullo, V, Pesonen, S, Diaconu, I, Escutenaire, S, Arstila, P T, Ugolini, M, et al. (2010). Oncolytic adenovirus coding for granulocyte macrophage colony-stimulating factor induces antitumoral immunity in cancer patients. Cancer Res 70: 4297-4309.
9. Heise, C, Hermiston, T, Johnson, L, Brooks, G, Sampson-Johannes, A, Williams, A, et al. (2000). An adenovirus E1A mutant that demonstrates potent and selective systemic anti-tumoral efficacy. Nat Med 6: 1134-1139.
10. Heise, C, Sampson-Johannes, A, Williams, A, McCormick, F, Hoff, von, D D and Kim, D H (1997). ONYX-015, an E1B gene-attenuated adenovirus, causes tumor-specific cytolysis and antitumoral efficacy that can be augmented by standard chemotherapeutic agents. Nat Med 3: 639-645.
11. Nowak, A K, Lake, R A, Marzo, A L, Scott, B, Heath, W R, Collins, E J, et al. (2003). Induction of tumor cell apoptosis in vivo increases tumor antigen cross-presentation, cross-priming rather than cross-tolerizing host tumor-specific CD8 T cells. J Immunol 170: 4905-4913.
12. Zitvogel, L, Apetoh, L, Ghiringhelli, F and Kroemer, G (2008). Immunological aspects of cancer chemotherapy. Nat Rev Immunol 8: 59-73.
13. van der Most, R G, Currie, A J, Robinson, B W S and Lake, R A (2008). Decoding dangerous death: how cytotoxic chemotherapy invokes inflammation, immunity or nothing at all. Cell Death Differ 15: 13-20.

14. Istrail, S, Florea, L, Halldórsson, B V, Kohlbacher, O, Schwartz, R S, Yap, V B, et al. (2004). Comparative immunopeptidomics of humans and their pathogens. Proc Natl Acad Sci USA 101: 13268-13272.
15. Cerullo, V, Pesonen, S, Diaconu, I, Escutenaire, S, Arstila, P T, Ugolini, M, et al. (2010). Oncolytic adenovirus coding for granulocyte macrophage colony-stimulating factor induces antitumoral immunity in cancer patients. Cancer Res 70: 4297-4309.
16. Cerullo, V, Seiler, M P, Mane, V, Brunetti-Pierri, N, Clarke, C, Bertin, T K, et al. (2007). Toll-like receptor 9 triggers an innate immune response to helper-dependent adenoviral vectors. Mol Ther 15: 378-385.
17. Suzuki, M, Cerullo, Bertin, T, Cela, Clarke, Guenther, M, et al. (2009). MyD88-dependent silencing of transgene expression during the innate and adaptive immune response to Helper-dependent adenovirus. Hum Gene Therdoi:10.1089/hum.2009.155.
18. Suzuki, M, Cela, R, Bertin, T K, Sule, G, Cerullo, V, Rodgers, J R, et al. (2011). NOD2 signaling contributes to the innate immune response against helper-dependent adenovirus vectors independently of MyD88 in vivo. Hum Gene Ther 22: 10 1082.
19. Muruve, D A, Pétrilli, V, Zaiss, A K, White, L R, Clark, S A, Ross, P J, et al. (2008). The inflammasome recognizes cytosolic microbial and host DNA and triggers an innate immune response. Nature 452: 103-107.
20. Tewalt, E F, Grant, J M, Granger, E L, Palmer, D C, Heuss, N D, Gregerson, D S, et al. (2009). Viral Sequestration of Antigen Subverts Cross Presentation to CD8+ T Cells. PLoS Pathog 5: e1000457.
21. Cerullo, V, Seiler, M P, Mane, V P, Brunetti-Pierri, N, Clarke, C, Bertin, T K, et al. (2007). Toll-like receptor 9 triggers an innate immune response to helper-dependent adenoviral vectors. Mol Ther 15: 378-385.
22. Suzuki, M, Cerullo, V, Bertin, T K, Cela, R, Clarke, C, Guenther, M, et al. (2010). MyD88-dependent silencing of transgene expression during the innate and adaptive immune response to helper-dependent adenovirus. Hum Gene Ther 21: 325-336.
23. Seiler, M P, Gottschalk, S, Cerullo, V, Ratnayake, M, Mane, V P, Clarke, C, et al. (2007). Dendritic cell function after gene transfer with adenovirus-calcium phosphate co-precipitates. Mol Ther 15: 386-392.
24. Suzuki, M, Cela, R, Bertin, T K, Sule, G, Cerullo, V, Rodgers, J R, et al. (2011). NOD2 Signaling Contributes to the Innate Immune Response Against Helper-Dependent Adenovirus Vectors Independently of MyD88 In Vivo. Hum Gene Therdoi:10.1089/hum.2011.002.
25. Fortier, M-H, Caron, E, Hardy, M-P, Voisin, G, Lemieux, S, Perreault, C, et al. (2008). The MHC class I peptide repertoire is molded by the transcriptome. Journal of Experimental Medicine 205: 595-610.
26. Fasbender, A, Zabner, J, Chillon, M, Moninger, T O, Puga, A P, Davidson, B L, et al. (1997). Complexes of adenovirus with polycationic polymers and cationic lipids increase the efficiency of gene transfer in vitro and in vivo. J Biol Chem 272: 6479-6489.
27. Croyle, M A, Yu, Q C and Wilson, J M (2000). Development of a rapid method for the PEGylation of adenoviruses with enhanced transduction and improved stability under harsh storage conditions. Hum Gene Ther 11: 1713-1722.
28. Wonganan, P and Croyle, M A (2010). PEGylated Adenoviruses: From Mice to Monkeys. Viruses 2: 468-502.
29. Toyoda, K, Ooboshi, H, Chu, Y, Fasbender, A1, Davidson, B L, Welsh, M J, et al. Cationic Polymer and Lipids Enhance Adenovirus-Mediated Gene Transfer to Rabbit Carotid Artery. stroke.ahajournals.org.
30. Cerullo, V, Diaconu, I, Romano, V, Hirvinen, M, Ugolini, M, Escutenaire, S, et al. (2012). An Oncolytic Adenovirus Enhanced for Toll-like Receptor 9 Stimulation Increases Antitumor Immune Responses and Tumor Clearance. Mol Ther 20, 2076.
31. Cerullo, V, Diaconu, I, Romano, V, Hirvinen, M, Ugolini, M, Escutenaire, S, et al. (2012). An Oncolytic Adenovirus Enhanced for Toll-like Receptor 9 Stimulation Increases Antitumor Immune Responses and Tumor Clearance. Mol Ther 20, 2076.
32. Dias, J D, Liikanen, I, Guse, K, Foloppe, J, Sloniecka, M, Diaconu, I, et al. (2010). Targeted chemotherapy for head and neck cancer with a chimeric oncolytic adenovirus coding for bifunctional suicide protein FCU1. Clin Cancer Res 16: 2540-2549.
33. Edukulla, R, Woller, N, Mundt, B, Knocke, S, Gurlevik, E, Saborowski, M, et al. (2009). Antitumoral immune response by recruitment and expansion of dendritic cells in tumors infected with telomerase-dependent oncolytic viruses. Cancer Res 69: 1448-1458.
34. R. B. Dell, S. Holleran, R. Ramakrishnan, Sample size determination. *ILAR journal/National Research Council, Institute of Laboratory Animal Resources* 43, 207 (2002).
35. M. W. Moore, F. R. Carbone, M. J. Bevan, Introduction of soluble protein into the class I pathway of antigen processing and presentation. *Cell* 54, 777 (Sep. 9, 1988).
36. A. Fasbender et al., Complexes of adenovirus with polycationic polymers and cationic lipids increase the efficiency of gene transfer in vitro and in vivo. *The Journal of biological chemistry* 272, 6479 (Mar. 7, 1997).
37. C. Heise et al., An adenovirus E1A mutant that demonstrates potent and selective systemic anti-tumoral efficacy. *Nature medicine* 6, 1134 (October, 2000).
38. Y. Deng et al., Assembly of MHC class I molecules with biosynthesized endoplasmic reticulum-targeted peptides is inefficient in insect cells and can be enhanced by protease inhibitors. *J Immunol* 161, 1677 (Aug. 15, 1998).
39. V. Cerullo et al., An oncolytic adenovirus enhanced for toll-like receptor 9 stimulation increases antitumor immune responses and tumor clearance. *Molecular therapy: the journal of the American Society of Gene Therapy* 20, 2076 (November, 2012).
40. W. W. Overwijk et al., gp100/pmel 17 is a murine tumor rejection antigen: induction of "self"-reactive, tumoricidal T cells using high-affinity, altered peptide ligand. *The Journal of experimental medicine* 188, 277 (Jul. 20, 1998).
41. W. W. Overwijk, N. P. Restifo, B16 as a mouse model for human melanoma. *Current protocols in immunology/edited by John E. Coligan . . .* [*et al.*] Chapter 20, Unit 20 1 (May, 2001).
42. Cimen Bozkus, C., A. B. Blazquez, T. Enokida, and N. Bhardwaj. 2021. 'A T-cell-based immunogenicity protocol for evaluating human antigen-specific responses', STAR Protoc, 2: 100758.

What is claimed:

1. A method of stimulating an infection and peptide-specific immune response in a subject in need thereof, wherein the method comprises administering to the subject adenoviral vectors comprising infection-specific polypeptides which are capable of stimulating an infection-specific immune response in the subject and which have been attached covalently or noncovalently onto a viral capsid of the vector to the subject;

wherein the infection-specific polypeptides are selected from the group consisting of one or both of Major Histocompatibility Complex of class I (MHC-I)-specific polypeptides and dendritic cell-presented anti-infection specific polypeptides and Major Histocompatibility Complex of class II (MHC-II)-specific polypeptides and dendritic cell-presented anti-infection specific polypeptides, further wherein the polypeptides have not been genetically encoded by said adenoviral vector.

2. The method of claim 1, wherein the infection-specific immune response is an anti-infection immune response.

3. The method of claim 1, wherein the subject is a human.

4. The method of claim 1, wherein the administration of the adenoviral vectors is conducted through an intratumoral, intra-arterial, intravenous, intrapleural, intravesicular, intracavitary or peritoneal injection, or an oral administration.

5. The method of claim 1, wherein the polypeptides have been attached to the capsid by electrostatic linkage.

6. The method of claim 1, wherein the polypeptides attached onto the viral capsid are all different polypeptides selected from two or more types of different polypeptides.

7. The method of claim 1, wherein the serotype of the adenoviral vector backbone is serotype 5.

8. The method of claim 1, wherein the adenoviral vector is an oncolytic adenoviral vector.

9. The method of claim 1, wherein the adenoviral vector comprises the E1 gene deletion.

10. The method of claim 1, wherein the adenoviral vector comprises one or more transgenes.

11. The method of claim 1, wherein the adenoviral vector comprises a capsid modification.

12. The method of claim 1, wherein the adenoviral vector is Ad5/3 comprising an Ad5 nucleic acid backbone and an Ad3 fiber knob.

13. An adenoviral vector adapted to stimulate an infection and peptide-specific immune response in a subject, comprising infection-specific polypeptides which are capable of stimulating an infection-specific immune response in the subject and which have been attached covalently or noncovalently onto a viral capsid of the vector;

wherein the infection-specific polypeptides are selected from the group consisting of one or both of Major Histocompatibility Complex of class I (MHC-I)-specific polypeptides and dendritic cell-presented anti-infection specific polypeptides and Major Histocompatibility Complex of class II (MHC-II)-specific polypeptides and dendritic cell-presented anti-infection specific polypeptides, further wherein the polypeptides have not been genetically encoded by said adenoviral vector.

14. The adenoviral vector of claim 13, wherein the infection-specific immune response is an anti-infection immune response.

15. The adenoviral vector of claim 13, wherein the subject is a human.

16. The adenoviral vector of claim 13, wherein the polypeptides have been attached to the capsid by electrostatic linkage.

17. The adenoviral vector of claim 13, wherein the polypeptides attached onto the viral capsid are all different polypeptides selected from two or more types of different polypeptides.

18. The adenoviral vector of claim 13, wherein the serotype of the adenoviral vector backbone is serotype 5.

19. The adenoviral vector of claim 13, wherein the adenoviral vector is an oncolytic adenoviral vector.

20. The adenoviral vector of claim 13, wherein the adenoviral vector comprises the E1 gene deletion.

21. The adenoviral vector of claim 13, wherein the adenoviral vector comprises one or more transgenes.

22. The adenoviral vector of claim 13, wherein the adenoviral vector comprises a capsid modification.

23. The adenoviral vector of claim 13, wherein the adenoviral vector is Ad5/3 comprising an Ad5 nucleic acid backbone and an Ad3 fiber knob.

24. A pharmaceutical composition comprising the adenoviral vector of claim 13.

25. A method of treating an infection in a subject in need thereof, wherein the method comprises administration to the subject of adenoviral vectors comprising infection-specific polypeptides which are capable of stimulating an infection-specific immune response in the subject and which have been attached covalently or non-covalently onto a viral capsid of the vector;

wherein the infection-specific polypeptides are selected from the group consisting of one or both of Major Histocompatibility Complex of class I (MHC-I)-specific polypeptides and dendritic cell-presented anti-infection specific polypeptides and Major Histocompatibility Complex of class II (MHC-II)-specific polypeptides and dendritic cell-presented anti-infection specific polypeptides, further wherein the infection-specific polypeptides have not been genetically encoded by said adenoviral vector.

26. The method of claim 25, wherein the infection-specific immune response is an anti-infection immune response.

27. The method of claim 25, wherein the subject is a human.

28. The method of claim 25, wherein the administration of the adenoviral vectors is conducted through an intratumoral, intra-arterial, intravenous, intrapleural, intravesicular, intracavitary or peritoneal injection, or an oral administration.

29. The method of claim 25, wherein the infection-specific polypeptides have been attached to the capsid by electrostatic linkage.

30. The method of claim 25, wherein the infection-specific polypeptides attached onto the viral capsid are all different infection-specific polypeptides selected from two or more types of different infection-specific polypeptides.

31. The method of claim 25, wherein the serotype of the adenoviral vector backbone is serotype 5.

32. The method of claim 25, wherein the adenoviral vectors are an oncolytic adenoviral vector.

33. The method of claim 25, wherein the adenoviral vectors comprise the E1 gene deletion.

34. The method of claim 25, wherein the adenoviral vectors comprise one or more transgenes.

35. The method of claim 25, wherein the adenoviral vectors comprise a capsid modification.

36. The method of claim 25, wherein the adenoviral vectors are Ad5/3 vectors each comprising an Ad5 nucleic acid backbone and an Ad3 fiber knob.

* * * * *